(12) United States Patent
Barawkar et al.

(10) Patent No.: US 9,593,115 B2
(45) Date of Patent: Mar. 14, 2017

(54) SUBSTITUTED FUSED TRICYCLIC COMPOUNDS, COMPOSITIONS, AND MEDICINAL APPLICATIONS THEREOF

(71) Applicant: ADVINUS THERAPEUTICS LIMITED, Bangalore (IN)

(72) Inventors: Dinesh Barawkar, Pune (IN); Anish Bandyopadhyay, Pune (IN); Robert Zahler, Pennington, NJ (US); Robindro Sarangthem, Pune (IN); Yogesh Waman, Pune (IN); Rajesh Bonagiri, Pune (IN); Dilip Jadhav, Pune (IN); Partha Mukhopadhyay, Pune (IN)

(73) Assignee: ADVINUS Therapeutics Ltd.

( * ) Notice: Subject to any disclaimer, the term of this patent is extended or adjusted under 35 U.S.C. 154(b) by 0 days.

(21) Appl. No.: 14/430,012

(22) PCT Filed: Sep. 18, 2013

(86) PCT No.: PCT/IN2013/000564
§ 371 (c)(1),
(2) Date: Mar. 20, 2015

(87) PCT Pub. No.: WO2014/045305
PCT Pub. Date: Mar. 27, 2014

(65) Prior Publication Data
US 2015/0239886 A1      Aug. 27, 2015

(30) Foreign Application Priority Data

Sep. 21, 2012   (IN) .......................... 3940/CHE/2012

(51) Int. Cl.
| C07D 471/14 | (2006.01) |
| A61K 31/5025 | (2006.01) |
| A61K 45/06 | (2006.01) |
| C07D 487/14 | (2006.01) |

(52) U.S. Cl.
CPC ........ *C07D 471/14* (2013.01); *A61K 31/5025* (2013.01); *A61K 45/06* (2013.01); *C07D 487/14* (2013.01)

(58) Field of Classification Search
CPC .................................................. C07D 403/00
See application file for complete search history.

(56) References Cited

U.S. PATENT DOCUMENTS

| 2003/0078277 A1 | 4/2003 | Hibi |
| 2010/0105661 A1 | 4/2010 | Shirakami et al. |

FOREIGN PATENT DOCUMENTS

| EP | 2420502 A1 | 2/2012 |
| WO | 9965908 A1 | 12/1999 |
| WO | 9965909 A1 | 12/1999 |
| WO | 0142246 A1 | 6/2001 |
| WO | 0200661 A1 | 1/2002 |
| WO | 03068157 A2 | 8/2003 |
| WO | 2004047843 A1 | 6/2004 |
| WO | 2004058749 A1 | 7/2004 |
| WO | 2004099204 A1 | 11/2004 |
| WO | 2004099205 A1 | 11/2004 |

(Continued)

OTHER PUBLICATIONS

Vippagunta et al. (2001).*
Wolff et al. (1995).*
Didenko et al., 2009, Russian Journal of Organic Chemistry 45(2), 211-214. "Transformations of 3-alkyl-4-(methoxyphenyl)-1H-pyrazole-5-diazonium salts".
Bogza et al., 2004, Chemistry of Heterocyclic Compounds 40(11), 1506-1507. "Novel method for synthesis of polynuclear heterocyclic systems with a pyridazine ring".
Stockmann et al., 2008, Tetrahedron 64(49), 11180-11184. "Preparation of novel pyridine-fused tris-heterocycles; pyrido[4,3-e]pyrrolo-/pyrido[4,3-e]furano[2,3-c]pyridazines and pyrido[3,4-b]pyrollo[3,2-d]pyrrole".

(Continued)

*Primary Examiner* — Paul V Ward
(74) *Attorney, Agent, or Firm* — Zareefa B. Flener; Flener IP Law

(57) ABSTRACT

The present invention relates to substituted fused tricyclic compounds of formula (I), their tautomers, polymorphs, stereoisomers, prodrugs, solvates, co-crystals, pharmaceutically acceptable salts, pharmaceutical compositions containing them and methods of treating conditions and diseases that are mediated by JAK activity.

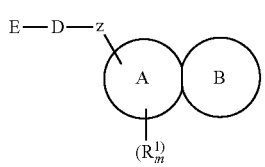

The compounds of the present invention are useful in the treatment, prevention or suppression of diseases and disorders mediated by JAK activity. Such conditions include, but not limited to, arthritis, Alzheimer's disease, autoimmune thyroid disorders, cancer, diabetes, leukemia, T-cell prolymphocytic leukemia, lymphoma, myleoproliferation disorders, lupus, multiple myeloma, multiple sclerosis, osteoarthritis, sepsis, psoriatic arthritis, prostate cancer, T-cell autoimmune disease, inflammatory diseases, chronic and acute allograft transplant rejection, bone marrow transplant, stroke, asthma, chronic obstructive pulmonary disease, allergy, bronchitis, viral diseases, or Type I diabetes, complications from diabetes, rheumatoid arthritis, asthma, Crohn's disease, dry eye, uveitis, inflammatory bowel disease, organ transplant rejection, psoriasis and ulcerative colitis. The present disclosure also relates to process for the preparation of such compounds, and to pharmaceutical compositions containing them.

6 Claims, No Drawings

(56) References Cited

FOREIGN PATENT DOCUMENTS

| WO | 2005005393 A2 | 1/2005 |
|---|---|---|
| WO | 2005009389 A2 | 2/2005 |
| WO | 2005037843 A1 | 4/2005 |
| WO | 2005060972 A2 | 7/2005 |
| WO | 2005095400 A1 | 10/2005 |
| WO | 2005105788 A1 | 11/2005 |
| WO | 2005124342 A2 | 12/2005 |
| WO | 2006096270 A1 | 9/2006 |
| WO | 2007007919 A2 | 1/2007 |
| WO | 2007070514 A1 | 6/2007 |
| WO | 2007077949 A1 | 7/2007 |
| WO | 2007084557 A2 | 7/2007 |
| WO | 2007117494 A1 | 10/2007 |
| WO | 2007140222 A2 | 12/2007 |
| WO | 2009054941 A1 | 4/2009 |
| WO | 2009071701 A1 | 6/2009 |
| WO | 2009155156 A1 | 12/2009 |
| WO | 2010039939 A1 | 4/2010 |
| WO | 2010051781 A1 | 5/2010 |
| WO | 2010085684 A1 | 7/2010 |
| WO | 2011003155 A1 | 1/2011 |
| WO | 2011003418 A1 | 1/2011 |
| WO | 2011068881 A1 | 6/2011 |
| WO | 2011143646 A1 | 11/2011 |

OTHER PUBLICATIONS

Catlett-Falcone et al., 1999, Immunity 10, 105-115. "Constitutive Activation of Stat3 Signaling Confers Resistance to Apoptosis in Human U266 Myeloma Cells".

Changelian, 2003, Science 302, 875-878. "Prevention of Organ Allograft Rejection by a Specific Janus Kinase 3 Inhibitor".

Constantinescu et al., 2007, Trends in Biochemical Sciences 333, 122-131. "Mining for JAK-STAT mutations in cancer".

Demoulin et al., 1996, Mol. Cell. Biol. 16, 4710-4716. "A single tyrosine of the interleukin-9 (IL-9) receptor is required for STAT activation, antiapoptotic activity, and growth regulation by IL-9".

Jurlander et al., 1997, Blood 89, 4146-4152. "Characterization of Interleukin-10 Receptor Expression on B-Cell Chronic Lymphocytic Leukemia Cells".

Kaneko et al., 1997, Clin. Exp. Immunol. 109, 185-193. "Rescue by cytokines of apoptotic cell death induced by IL-2 deprivation of human antigen-specific T cell clones".

Karaghiosoff et al., 2000, Immunity 13, 549-560. "Partial impairment of cytokine responses in Tyk2-deficient mice".

Kisseleva et al., 2002, Gene 285, 1-24. "Signaling through the JAK/STAT pathway, recent advances and future challenges".

Krueger et al., 2007, N. Engl. J. Med. 356, 580-592. "A Human Interleukin-12/23 Monoclonal Antibody for the Treatment of Psoriasis".

Kudlacz et al., 2004 Am. J. Transplant 4, 51-57. "The Novel JAK-3 Inhibitor CP-690550 Is a Potent Immunosuppressive Agent in Various Murine Models".

Levy D. and Loomis C., 2007, N. Engl. J. Med. 357, 1655-1658. "STAT3 Signaling and the Hyper-IgE Syndrome".

Levy et al., 2005, Nat. Rev. Mol. Cell. Biol. 3, 651-662. "STATs: transcriptional control and biological impact".

Li et al., 2001, The Journal of Immunology, 166(5), 3491-3498. "Oncostatin M-Induced Matrix Metalloproteinase and Tissue Inhibitor of Metalloproteinase-3 Genes Expression in Chondrocytes Requires Janus Kinase/STAT Signaling Pathway".

Malaviya et al., 1999, Biochem. Biophys. Res. Commun. 257, 807-813. "Genetic and Biochemical Evidence for a Critical Role of Janus Kinase (JAK)-3 in Mast Cell-Mediated Type I Hypersensitivity Reactions".

Malaviya et al., 1999, J. Biol. Chem. 274, 27028-27038. "Targeting Janus kinase 3 in mast cells prevents immediate hypersensitivity reactions and anaphylaxis".

Mannon et al., 2004, N. Engl. J. Med. 351, 2069-2079. "Anti-interleukin-12 antibody for active Crohn's disease".

Muller-Ladner et al., 2000, J. Immunol. 164, 3894-3901. "Activation of the IL-4 STAT Pathway in Rheumatoid Synovium".

Mullighan et al., 2009, Proc. Natl. Acad. Sci. USA 103, 9414-9418. "JAK mutations in high-risk childhood acute lymphoblastic leukemia".

Nakamura et al., 1996, J. Biol. Chem. 271, 19483-19488. "An Epidermal Growth Factor Receptor/Jak2 Tyrosine Kinase Domain Chimera Induces Tyrosine Phosphorylation of Stat5 and Transduces a Growth Signal in Hematopoietic Cells".

Nielsen et al., 1997, Proc. Natl. Acad. Sci. USA 94, 6764-6769. "Constitutive activation of a slowly migrating isoform of Stat3 in mycosis fungoides: Tyrphostin AG490 inhibits Stat3 activation and growth of mycosis fungoides tumor cell lines".

O'Shea et al., 2002, Cell, 109 (suppl.): S121-S131. "Cytokine signaling in 2002: new surprises in the Jak/Stat pathway".

O'Sullivan et al., 2007, Mol Immunol. 44(10), 2497-2506. "Cytokine receptor signaling through the Jak-Stat-Socs pathway in disease".

Reich et al., 2009, Nat. Rev. Drug Discov. 8, 355-356. "Ustekinumab".

Rodig et al., 1998, Cell, 93, 373-383. "Disruption of the Jak1 gene demonstrates obligatory and nonredundant roles of the Jaks in cytokine-induced biologic responses".

Schneinecker et al., 2009, Nat. Rev. Drug Discov. 8, 273-274. "Tocilizumab".

Shimoda et al., 2000. Immunity 13, 561-571. "Tyk2 plays a restricted role in IFN alpha signaling, although it is required for IL-12-mediated T cell function".

Sudbeck et al., 1999, Clin. Cancer Res. 5, 1569-1582. "Structure-based design of specific inhibitors of Janus kinase 3 as apoptosis-inducing antileukemic agents".

Suzuki et al., 2000, Blood 96, 2172-2180. "Role of common cytokine receptor γ chain (γc)- and Jak3-dependent signaling in the proliferation and survival of murine mast cells".

Tam et al., 2007, British Journal of Cancer 97, 378-383. "Expression levels of the JAK/STAT pathway in the transition from hormone-sensitive to hormone-refractory prostate cancer".

Trieu et al., 2000, Biochem Biophys. Res. Commun. 267, 22-25. "A Specific Inhibitor of Janus Kinase-3 Increases Survival in a Transgenic Mouse Model of Amyotrophic Lateral Sclerosis".

Velazquez et al., 1992. Cell 70, 313-322. "A protein tyrosine kinase in the interferon αβ signaling pathway".

Watford, W. T. and O'Shea, J. J., 2006, Immunity 25, 695-697. "Human Tyk2 Kinase Deficiency: Another Primary Immunodeficiency Syndrome".

Wilks A. F., 1989, Proc. Natl. Acad. Sci. U.S.A. 86, 1603-1607. "Two putative protein-tyrosine kinases identified by application of the polymerase chain reaction".

Xiang et al., 2008, Blood 111, 4809-4812. "Identification of somatic JAK1 mutations in patients with acute myeloid leukemia".

Alkorta et al., 2005, Journal of Physical Organic Chemistry 18(8), 719-724. "Theoretical estimation of the annular tautomerism of indazoles".

Kirken, 2001, Transpl. Proc. 33, 3268-3270. "Targeting Jak3 for immune suppression and allograft acceptance".

Yu et al., 1997, J. Immunol. 159, 5206-5210. "Constitutive activation of the Janus kinase-STAT pathway in T lymphoma overexpressing the Lck protein tyrosine kinase".

\* cited by examiner

SUBSTITUTED FUSED TRICYCLIC COMPOUNDS, COMPOSITIONS, AND MEDICINAL APPLICATIONS THEREOF

FIELD OF THE INVENTION

The present invention relates to substituted fused tricyclic compounds, their tautomers, polymorphs, stereoisomers, prodrugs, solvates, co-crystals, pharmaceutically acceptable salts, pharmaceutical compositions containing them and methods of treating conditions and diseases that are mediated by Janus family kinases (JAK) activity.

BACKGROUND OF THE INVENTION

Protein phosphorylation catalyzed by protein kinases is one of the most common modes of regulation of protein function. By adding phosphate groups to substrate proteins, protein kinases alter the activity, localization and overall function of many proteins and influence almost all cellular processes. At least 30% of the human proteome is estimated to be phosphorylated by protein kinases. Protein phosphorylation is particularly prominent in signal transduction. Protein kinases are implicated in a variety of diseases including inflammation, cancer, neurodegenerative disorders, diabetes, infectious diseases, and so on. The human genome is estimated to encode 518 protein kinases. Based on the residue they phosphorylate protein kinases are classified into 2 major groups: 1) protein tyrosine kinases or PTKs (~90 members) and 2) protein serine/threonine kinases (~378 members). The rest are 'atypical' kinases. The kinase domain of all typical protein kinases is highly conserved and consists of two lobes (N-lobe and C-lobe) that surround the nucleotide binding site.

Among the PTKs, a small subfamily known as Janus family kinases (JAKs) consists of four members namely JAK1, JAK2, JAK3, and Tyk2. They are cytoplasmic protein tyrosine kinases that play essential and specific roles in immune cell development and function by participating in the cytokine receptor signal transduction. Binding of cytokines activates the JAKs which in turn phosphorylate and activate a set of transcription factors known as STAT (signal transducers and activators of transcription) proteins. The STAT proteins form homo- or heterodimers and translocate to the nucleus where they induce transcription of genes. The central role of the JAK/STAT pathways in relaying the signals from many cytokine receptors, and the involvement of several cytokines in a range of pathologies such as diseases of the immune system and cancer, makes them attractive targets for drug discovery.

Among the JAKs, JAK3 has particularly selective functions. Unlike the other members of the JAK family, which show wide tissue distribution, JAK3 expression is restricted to the cells of hematopoietic lineage. Unlike the other members of the JAK family which associate with multiple cytokine receptors, JAK3 associates uniquely with γc-chain, the common signaling subunit of receptor complexes for six cytokines namely interleukin (IL)-2, IL-4, IL-7, IL-9, IL-15 and IL-21. These ILs play a pivotal role in the lymphoid development and function. JAK3 is inducible in T and 13 cells and expressed at high levels in NK cells and normally in thymocytes, platelets, mast cells. JAK3, through its association with the IL-2 receptor, is critical for lymphocyte survival, differentiation, and function. In humans, mutations in either JAK3 or γc-chain are associated with rare and inherited disorder known as severe combined immunodeficiency (SCID) indicating their critical role in the development and function of lymphocytes. These patients do not have deficits outside the immune system and hematopoietic stem cell transplants are curative, suggesting very discrete functions for JAK3.

The SCID phenotype was also observed in JAK3 knockout mice. JAK3 deficiency in humans results in the lack of T cells and NK cell development; B cells are present but their function is not normal. Unlike humans, JAK3 knockout mice show the lack of B cells and have relatively small numbers of T cells. The reason for this difference in the role of JAK3 in B cell development between mice and humans is not clear but it could be due to species-specific cytokine usage. However, similar to humans, JAK3 knockout mice did not display any effect on the development of myeloid or erythroid cells confirming the restriction of JAK3 function to lymphocyte development.

Though initially it was believed that the primary function of JAK3 is regulation of function of T and B cells through cytokine dependent pathway, recent studies using JAK3 knockout mice and JAK3 specific inhibitors suggest that JAK3 can transduce signals in non-cytokine-dependent manner in mast cells and that JAK3 plays a key role in mast cell mediated inflammatory responses. The enzymatic activity of JAK3 is increased by IgE receptor cross-linking in mast cells.

Other JAK family members Tyk2, JAK1 and JAK2 have functions within and outside immune cells. Mutations of Tyk2 cause autosomal recessive hyper IgE syndrome and JAK2 gain-of-function mutations (V617F) underlie a subset of disorders collectively referred to as myeloproliferative diseases. In some contexts, both JAK1 and JAK3 play dual and equal roles in receptor phosphorylation events indicating potential synergistic effects due to suppressing both JAK3 and JAK1 signaling.

JAK family members have been implicated in additional conditions including myeloproliferative disorders (O'Sullivan et al, 2007, *Mol Immunol.* 44(10), 2497-506), where mutations in JAK2 have been identified. This indicates that inhibitors of JAK in particular JAK2 may also be of use in the treatment of myeloproliferative disorders. Additionally, the JAK family, in particular JAK1, JAK2 and JAK3, has been linked to cancers, in particular leukaemias e.g. acute myeloid leukaemia (O'Sullivan et al, 2007, *Mol Immunol.* 44(10), 2497-506; Xiang et al, 2008, "Identification of somatic JAK1 mutations in patients with acute myeloid leukemia" Blood First Edition Paper, prepublished online Dec. 26, 2007; DOI 10.1 182/blood-2007-05-090308) and acute lymphoblastic leukaemia (Mullighan et al, 2009) or solid tumours e.g. uterine leiomyosarcoma (Constantinescu et al, 2007, Trends in Biochemical Sciences 33(3), 122-131), prostate cancer (Tarn et al, 2007, *British Journal of Cancer,* 97, 378-383). These results indicate that inhibitors of JAK, in particular of JAK1 and/or JAK2, may also have utility in the treatment of cancers (leukaemias and solid tumours e.g. uterine leiomyosarcoma, prostate cancer).

JAK1 is a novel target in the immuno-inflammatory disease area. JAK1 heterodimerizes with the other JAKs to transduce cytokine-driven pro-inflammatory signaling. Therefore, inhibition of JAK1 and/or other JAKs is expected to be of therapeutic benefit for a range of inflammatory conditions as well as for other diseases driven by JAK-mediated signal transduction.

Vandeghinste et al. (WO 2005/124342) discovered JAK1 as a target whose inhibition might have therapeutic relevance for several diseases including OA. Knockout of the JAK1 gene in mice demonstrated that JAK1 plays essential and non-redundant roles during development: JAK1−/− mice died within 24 h after birth and lymphocyte development was severely impaired. Moreover, JAK1−/− cells were not, or less, reactive to cytokines that use class II cytokine receptors, cytokine receptors that use the gamma-c subunit for signaling and the family of cytokine receptors that use the gp130 subunit for signaling (Rodig et al, 1998, *Cell*, 93, 373-383). Various groups have implicated JAK-STAT signaling in chondrocyte biology (Li et al, 2001, *The Journal of Immunology*, 166, 5, 3491-3498).

JAK1 was initially identified in a screen for novel kinases (Wilks A. F., 1989, *Proc. Natl. Acad. Sci. U.S.A.* 86, 1603-1607). Genetic and biochemical studies have shown that JAK1 is functionally and physically associated with the type I interferon (e.g., IFNalpha), type II interferon (e.g., IFNgamma), IL-2 and IL-6 cytokine receptor complexes (Kisseleva et al., 2002, gene 285, 1-24; Levy et al., 2005, *Nat. Rev. Mol. Cell. Biol.* 3, 651-662; O'Shea et al., 2002, *Cell*, 109 (suppl.): S121-S131). JAK1 knockout mice die perinatally due to defects in LIF receptor signaling (Kisseleva et al., 2002, gene 285, 1-24; O'Shea et al., 2002, *Cell*, 109 (suppl.): S121-S131). Characterization of tissues derived from JAK1 knockout mice demonstrated critical roles for this kinase in the IFN, IL-10, IL-2/IL-4, and IL-6 pathways. A humanized monoclonal antibody targeting the IL-6 pathway (Tocilizumab) was recently approved by the European Commission for the treatment of moderate-to-severe rheumatoid arthritis (Scheinecker et al., 2009, *Nat. Rev. Drug Discov.* 8, 273-274).

TYK2 is a potential target for immuno-inflammatory diseases, being validated by human genetics and mouse knock-out studies (Levy D. and Loomis C. (2007)).

TYK2 associates with the type I interferon (e.g., IFNalpha), IL-6, IL-10, IL-12 and IL-23 cytokine receptor complexes (Kisseleva et al., 2002, gene 285, 1-24; Watford, W. T. & O'Shea, J. J., 2006, Immunity 25, 695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and 11-23 cytokines (Ustekinumab) was recently approved by the European Commission for the treatment of moderate-to-severe plaque psoriasis (Krueger et al., 2007, N. Engl. J. Med. 356, 580-92; Reich et al., 2009, *Nat. Rev. Drug Discov.* 8, 355-356). In addition, an antibody targeting the IL-12 and IL-23 pathways underwent clinical trials for treating Crohn's Disease (Mannon et al., 2004, N. Engl. J. Med. 351, 2069-79).

The role of TYK2 in the biological response to cytokines was first characterized using a mutant human cell line that was resistant to the effects of Type I interferons (IFNs) and the demonstration that IFNa responsiveness could be restored by genetic complementation of TYK2 (Velazquez et al, 1992. *Cell* 70, 313-322). Further in vitro studies implicated TYK2 in the signaling pathways of multiple other cytokines involved in both innate and adaptive immunity. Analysis of TYK-2 mice however revealed less profound immunological defects than were anticipated (Karaghiosoff et al, 2000. Immunity 13, 549-560; Shimoda et al, 2000. *Immunity* 13, 561-671). Surprisingly, TYK2 deficient mice display merely reduced responsiveness to IFNα/β and signal normally to interleukin 6 (IL-6) and interleukin 10 (IL-10), both of which activate TYK2 in vitro. In contrast, TYK2 was shown to be essential for IL-12 signaling with the absence of TYK2 resulting in defective STAT4 activation and the failure of T cells from these mice to differentiate into IFNγ-producing Th1 cells. Consistent with the involvement of TYK2 in mediating the biological effects of Type I IFNs and IL-12, TYK2−/− mice were more susceptible to viral and bacterial infections.

US 20100105661, WO 2007077949, WO 2007007919, WO 199965909, WO 200142246, WO 200200661, WO 2005060972 discloses JAK3 inhibitors. US 20030078277, WO 2005009389, WO 2005105788, WO2011068881, EP2420502, discloses tricyclic derivatives where as WO2011068881, EP2420502, WO0142246, WO03068157, WO9965908, WO2004047843, WO2004058749, WO2004099204, WO2004099205, WO2005037843, WO200505393, WO2005095400, WO2006096270, WO2007007919, WO2007070514, WO2007084557, WO2007117494, WO2007140222, WO2009054941, WO2009071701, WO2009155156, WO2010039939, WO2010051781, WO2010085684, WO2011003418, WO201103155 discloses bicyclic derivatives.

In aggregate, because of its restricted distribution and function within the hematopoietic cells, JAK3 has been viewed as an attractive therapeutic target for the development novel class of immunosuppressive drugs. JAK3 inhibitors would be useful in treating many autoimmune and inflammatory diseases such as, but not limited to rheumatoid arthritis, psoriasis, psoriatic arthritis, transplantation rejection, graft-versus-host disease, multiple sclerosis, inflammatory bowel disease, systemic lupus erythematosus, allergic diseases and asthma, and Type-1 diabetes. Since JAK3-SCID patients do not exhibit pathology outside the immune system, in principle, a selective JAK3 inhibitor should have very limited and specific effects. Many of the currently used immunosuppressive drugs such as anti-metabolites, corticosteroids, and the inhibitors of calcineurin and mTOR target widely expressed molecules and hence are associated with adverse effects causing morbidity and mortality as the treatment is chronic. Similarly biologic anti-inflammatory agents such as TNF-alpha blockers are also associated with adverse events such as increase in the rate of serious infections, including tuberculosis and other opportunistic infections, injection site/infusion-related reactions, increased risk of lymphoma, the development of autoantibodies and a higher rate of congestive heart failure (CHF) in patients who already are known to have an increased risk of CHF. As a result, potent and selective JAK3 inhibitors are expected to have significant advantages over current regimens.

SUMMARY OF THE INVENTION

The present invention provides compounds of formula (I), their tautomers, polymorphs, stereoisomers, prodrugs, solvates, co-crystals, pharmaceutically acceptable salts, pharmaceutical compositions containing them and methods of treating conditions and diseases that are mediated by JAK (Janus family kinases) activity,

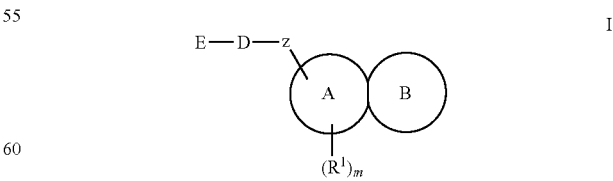

wherein,

A represents a five, six or seven membered ring which is saturated, unsaturated or partially unsaturated optionally having upto three heteroatoms selected from O, N or S;

B represents a fused heterocycle selected from:

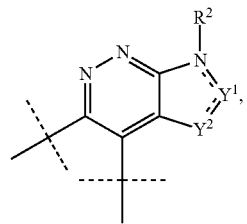 (IIa)

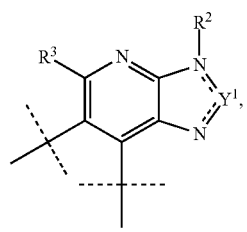 (IIb)

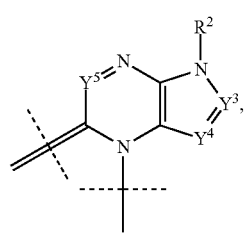 (IIc)

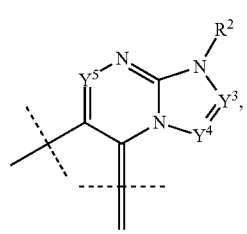 (IId)

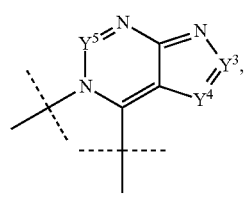 (IIe)

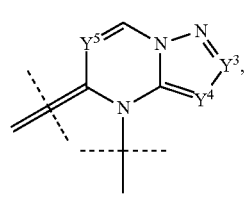 (IIf)

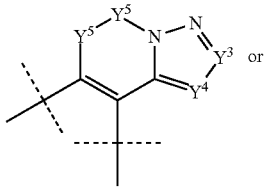 (IIg) or

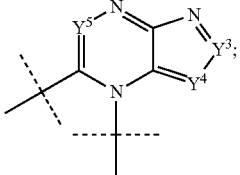 (IIh);

╌╌╌ represents a single bond or a double bond provided that $R^2$ is absent when the bond between N to which it is attached and $Y^1$ represents a double bond;

$Y^1$, $Y^3$, $Y^4$ and $Y^5$ independently represents N or $CR^4$;

$Y^2$ represents $NR^{4'}$ or $C R^4R^{4'}$ provided that $R^{4'}$ is absent when the bond between $Y^1$ and $Y^2$ represents a double bond;

$R^1$ is selected from hydrogen, alkyl, alkenyl, alkynyl, alkoxy, acyl, acylamino, acyloxy, $-(CR^aR^b)_nC(O)R^5$, $-(CR^aR^b)_nNR^6R^7$, aminocarbonyl, alkoxycarbonylamino, alkylsulfonylamino, aminocarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy $-SO_3H$, alkylthio, aminosulfonyl, alkylsulfonyl, or nitro;

$R^2$ is selected from hydrogen, alkyl, cycloalkyl, aryl, heterocyclyl or heteroaryl;

$R^3$ is selected from hydrogen, hydroxyalkyl, amino, monoalkylamino, dialkylamino, halogen, perhaloalkyl, cyano, nitro, alkoxyalkyl, carboxy, carboxyalkyl, acyl, aminocarbonyl, alkyl, alkenyl, alkynyl, hydroxyalkyl, carboxyalkyl, haloalkyl and haloalkyloxy;

$R^4$ and $R^{4'}$ are independently selected from the group consisting of hydrogen, halogen, hydroxyl, cyano, alkyl, alkenyl, alkynyl, haloalkyl, hydroxyalkyl, carboxyalkyl, cycloalkyl, cycloalkenyl, cycloalkylalkyl, aryl, arylalkyl, heterocyclyl, heterocyclylalkyl, heteroaryl and heteroarylalkyl;

wherein alkyl, alkenyl, alkynyl, cycloalkyl, cycloalkylalkyl, arylalkyl, aryl, heteroaryl, heteroarylalkyl, heterocyclyl, and heterocyclylalkyl are, independently unsubstituted or substituted with upto four substituents independently selected from alkyl, alkenyl, alkynyl, alkoxy, acyl, acyloxy, acylamino, amino, halogen, hydroxy, hydroxyalkyl, keto, thiocarbonyl, carboxy, alkylcarboxy, carboxyalkyl, $-SO_3H$, aminocarbonyl, aminocarbonylamino, alkoxycarbonylamino, hydroxyamino, alkoxyamino, nitro, azido, cyano, cycloalkyl, cycloalkylalkyl, aryl, arylalkyl, heterocyclyl, heterocyclylalkyl, heteroaryl and heteroarylalkyl cycloalkenyl, cycloalkylamino, arylamino, heterocyclylamino, heteroarylamino, cycloalkyloxy, aryloxy, heterocyclyloxy or heteroaryloxy;

Z is a bond or is selected from cycloalkylene, cycloalkylenealkyl, cycloalkenylene, cycloalkyleneoxo, cycloalkyleneamino, arylene, arylenealkyl, arylenethio, arylenoxy, aryleneamino, arylenealkoxycarbonylamino, arylenesulfonyl, arylenesulfonylamino, heterocyclylene, heterocyclylenealkyl, heterocyclyleneoxy, heterocyclylenealkyloxy, heterocyclyleneamino, heterocyclylenethio, heterocyclylenealkylamino heteroarylene, heteroarylenealkyl, heteroaryleneoxy, heteroaryleneamino, spirocyclyl, $(C_{1-6})$alkylene, $(C_{1-6})$alkenylene or $(C_{1-6})$alkynylene wherein one or more than one methylene groups from alkylene, alkenylene or alkynylene are optionally replaced by hetero atoms or groups such as —O—, —S(O)p, —N($R^5$)—, or —C(O);

D is a bond or is selected from cycloalkylene, cycloalkenylene, cycloalkylenecarbonyl, cycloalkylenealkoxy, cycloalkyleneamino, arylene, arylenecarbonyl, arylenealkoxycarbonyl, arylenealkoxycarbonylamino, aryleneaminocarbonyl, heterocyclylene, heterocyclylenealkyl, heterocyclylenecarbonyl, heterocyclylenealkylamino, heteroarylene, heteroarylenecarbonyl, heteroarylenealkylamino, ($C_{1-6}$)alkylene, ($C_{1-6}$)alkenylene or ($C_{1-6}$)alkynylene wherein one or more than one methylene groups from alkylene, alkenylene or alkynylene are optionally replaced by hetero atoms or groups such as —O—, —S(O) p-, —N($R^5$)—, —C(O) or —C(=NR")— wherein R" is H, alkyl, cyano, hydroxy, hydroxyalkyl, haloalkyl or perhaloalkyl;

E is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —($CR^aR^b$)$_n$$OR^5$, —$SR^5$, —($CR^aR^b$)$_n$$COOR^5$, —($CR^aR^b$)$_n$$NR^6R^7$, —($CR^aR^b$)$_n$C(O)$NR^6R^7$, —($CR^aR^b$)$_n$$NR^5$C(O)$NR^6R^7$, thiocarbonyl, S(O)$_2$$NR^6R^7$, —$NR^5$S(O)$_2$$R^5$, —S(O)$_p$$R^5$, —$SO_3H$, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;

$R^5$ is selected from hydrogen, —($CR^aR^b$)$_n$$OR^8$, halogen, haloalkyl, —($CR^aR^b$)$_n$C(O)$R^8$, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, $OR^8$, —OC(O)$R^8$, —($CR^aR^b$)$_n$C(O)$NR^6R^7$, —$NR^8$C(O)$R^8$, —$SR^8$, —S(O)$_p$$R^8$, —S(O)$_2$$NR^6R^7$ or —$NR^8$S(O)$_2$$R^8$;

$R^6$ and $R^7$ are independently selected from hydrogen, —($CR^aR^b$)$_n$$OR^5$, haloalkyl, —($CR^aR^b$)$_n$C(O)$R^5$, alkyl, alkenyl, alkynyl, aryl, arylalkyl, heteroaryl, heteroarylalkyl, cycloalkyl, cycloalkylalkyl, heterocyclyl and heterocyclylalkyl, or $R^6$ and $R^7$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —($CR^aR^b$)$_n$$OR^5$, —$SR^5$, —($CR^aR^b$)$_n$$NR^6R^7$, oxo, alkylsulfonyl, —($CR^aR^b$)$_n$ $COOR^5$, —($CR^aR^b$)$_n$C(O)$NR^6R^7$, cycloalkyl, cycloalkylalkyl, aryl, arylalkyl, heterocyclyl, heterocyclylalkyl, heteroaryl, and heteroarylalkyl;

Z, D and E may be optionally substituted with one or more substituents independently selected from cyano, nitro, keto, oxo, halogen, haloalkyl, perhaloalkyl, hydroxyamino, —($CR^aR^b$)$_n$$OR^5$, —($CR^aR^b$)$_n$C(O)$R^5$, —OC(O)$R^5$, —$SR^5$, —($CR^aR^b$)$_n$$COOR^5$, —($CR^aR^b$)$_n$$NR^6R^7$, —($CR^aR^b$)$_n$C(O)$NR^6R^7$, —($CR^aR^b$)$_n$$NR^5$C(O)$NR^6R^7$, —$NR^5$C(O)$R^5$, thiocarbonyl, —S(O)$_2$$NR^6R^7$, —$NR^5$S(O)$_2$$R^5$, —S(O)$_p$$R^5$, —$SO_3H$, —OP(O)($R^9$)$_q$, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)$R^5$, —($CR^aR^b$)$_n$C(O)$NR^6R^7$, —$NR^5$C(O)$R^5$, —$SR^5$, —S(O)$_p$$R^5$, —S(O)$_2$$NR^6R^7$ or —$NR^5$S(O)$_2$$R^5$;

$R^8$ is selected from hydrogen, alkyl, alkoxy, haloalkyl, aryl, arylalkyl, heteroaryl, heteroarylalkyl, cycloalkyl, cycloalkylalkyl, heterocyclyl or heterocyclylalkyl;

wherein alkyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy or carboxyalkyl;

$R^9$ is selected from the group consisting of hydroxy and alkoxy;

$R^a$ and $R^b$ are independently selected from the group consisting of hydrogen, —$OR^5$, halogen, haloalkyl, perhaloalkyl and alkyl;

n is 0-6;

m is 0, 1 or 2;

p is 0, 1 or 2; and q is 1 or 2;

with the proviso that in (IIc) when $Y^5$ is $CR^4$, then $Y^3$ and $Y^4$ cannot be $CR^4$.

DETAILED DESCRIPTION OF THE INVENTION

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably, 1, 2, 3, 4, 5 or 6 carbon atoms. This term is exemplified by groups such as methyl, ethyl, n-propyl, iso-propyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —CH($CH_3$)$CH_2$—) and the like.

The term "substituted alkyl" or "substituted alkylene" refers to: 1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where R$^b$ is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2; or 2) an alkyl group or alkylene group as defined above that is interrupted by 1, 2, 3, 4, 5, 6, 7, 8, 9 or 10 atoms independently selected from oxygen, sulphur and NR$^d$, where R$^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, CF$_3$, amino, substituted amino, cyano, or —S(O)$_p$R$^c$, in which R$^c$ is alkyl, aryl, or heteroaryl and p is 0, 1, or 2; or 3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, SO$_3$H, aryl, aryloxy, heteroaryl, aminocarbonylamino, heteroaryloxy, heterocyclyl, heterocyclyloxy, hydroxyamino, alkoxyamino, nitro; —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —CH$_2$C≡CH), homopropargyl (or but-1-yn-4-yl, —CH$_2$CH$_2$C≡CH) and the like.

The term "alkynylene" refers to a diradical of a branched or an unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$ where R$^c$ is alkyl, aryl, or heteroaryl and p is 0, 1 or 2.

The term "cycloalkyl" refers to unless otherwise mentioned, carbocyclic groups of from 3 to 20 carbon atoms having a single cyclic ring or multiple condensed rings or spirocyclic rings or bridged rings which may be saturated or partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo[2.2.1]heptane, bicyclo[2.2.2] octane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, —C(O)R and —S(O)$_p$R$^b$, where R is hydrogen, hydroxyl, alkoxy, alkyl and cyclocalkyl, heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group R'"—O—, where R'" is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O)NR'R' where each R' is independently hydrogen, alkyl, aryl, heteroaryl, heterocyclyl or both R' groups are joined to form a heterocyclic group (e. g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "acylamino" refers to the group NR"C(O)R" where each R" is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —S(O)$_p$R$^c$, where R$^c$ is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

"Aryloxyalkyl" refers to the group alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoalkyl" refers to an amino group that is attached to $(C_{1-6})$alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3, 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —SO$_3$H, aryl, aryloxy, heteroaryl, aminosulfonyl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where R$^b$ is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —S(O)$_p$ R$^c$ where R$^c$ is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and $—S(O)_pR^c$, where $R^c$ is alkyl, aryl, or heteroaryl and p is 0, 1 or 2.

The term "carboxyalkyl" refers to the groups -alkylene-C(O)OH.

The term "alkylcarboxyalkyl" refers to the groups -alkylene-C(O)OR$^d$ where R$^d$ is alkyl, cycloalkyl, where alkyl, cycloalkyl are as defined herein, and may be optionally further substituted by alkyl, halogen, $CF_3$, amino, substituted amino, cyano, or $—S(O)_pR^c$, in which R$^c$ is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulphur within at least one ring. Such heteroaryl groups can have a single ring (e.g. pyridyl or furyl) or multiple condensed rings (e.g. indolizinyl, benzothiazolyl, or benzothienyl). Examples of heteroaryls include, but are not limited to, [1,2,4] oxadiazole, [1,3,4] oxadiazole, [1,2,4] thiadiazole, [1,3,4] thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above.

Unless otherwise constrained the heteroaryl or heterarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, $—SO_3H$, aryl, aryloxy, heteroaryl, aminocarbonylamino, heteroaryloxy, heterocyclyl, heterocyclyloxy, hydroxyamino, alkoxyamino, nitro, $—S(O)_2NR^aR^a$, $—NR^aS(O)_2R^a$ and $—S(O)_pR^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where R$^b$ is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino; substituted amino, cyano, and $—S(O)_nR^c$, where R$^c$ is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings or spirocyclic rings, or bridged rings unless otherwise mentioned, having from 1 to 40 carbon atoms and from 1 to 10 hetero atoms, preferably 1, 2, 3 or 4 heteroatoms, selected from nitrogen, sulphur, phosphorus, or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cyclocalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and $—S(O)_pR^b$, where R$^b$ is hydrogen, alkyl; aryl, heterocyclyl and heteroaryl; and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and $—S(O)R^c$, where R$^c$ is alkyl, aryl, or heteroaryl; and n is 0, 1 or 2.

The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" refers to a group —S(O)$_2$R.

The term "substituted sulfone" refers to a group —S(O)$_2$R, in which R is alkyl, aryl, or heteroaryl.

The compounds of the present invention may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, unless otherwise indicated, all physical forms are equivalent for the uses contemplated herein and are intended to be within the scope of the present invention.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (M−) is associated with the positive charge of the N atom. M− may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. M− is preferably an anion selected from chloride, bromide, iodide, sulphate, nitrate, acetate, maleate, oxalate, succinate or trifluoroacetate. More preferably M− is chloride, bromide, trifluoroacetate or methanesulphonate.

"Co-crystal" refers to a crystalline material comprising two or more compounds at ambient temperature (20 to 25[deg.] C., preferably 20[deg.] C.), of which at least two are held together by weak interaction, wherein at least one of the compounds is a co-crystal former. Weak interaction is being defined as an interaction which is neither ionic nor covalent and includes for example: hydrogen bonds, van der Waals forces, and interactions.

"Pharmaceutical composition" refers to one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

"Drug or pharmaceutically active agent" includes a drug or pharmaceutical agent that will elicit the biological or medical response of a tissue, system, animal or human that is being sought, for instance, by a researcher or clinician.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

"Therapeutically effective amount" is an amount of a compound of Formula (I)/(Ia) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The present invention provides compounds of formula (I), their tautomers, polymorphs, stereoisomers, prodrugs, solvates, co-crystals, pharmaceutically acceptable salts, pharmaceutical compositions containing them and methods of treating conditions and diseases that are mediated by JAK activity,

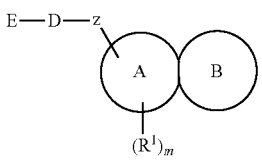

(I)

wherein,

A represents a five, six or seven membered ring which is saturated, unsaturated or partially unsaturated optionally having upto three heteroatoms selected from O, N or S;

B represents a fused heterocycle selected from:

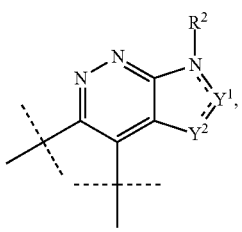

(IIa)

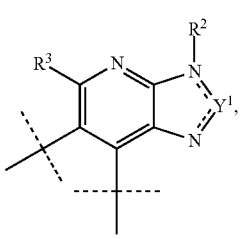

(IIb)

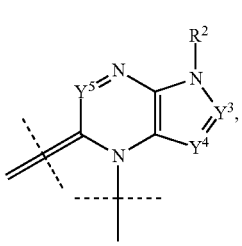

(IIc)

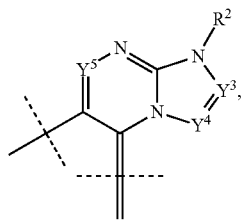

(IId)

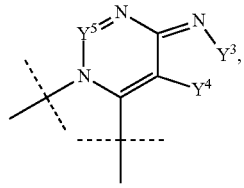

(IIe)

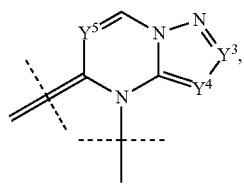

(IIf)

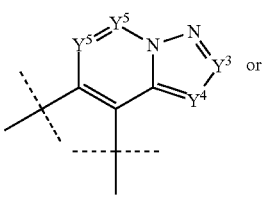

(IIg) or

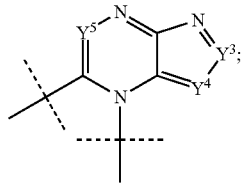

(IIh)

===== represents a single bond or a double bond provided that $R^2$ is absent when the bond between N to which it is attached and $Y^1$ represents a double bond;

$Y^1$, $Y^3$, $Y^4$ and $Y^5$ independently represents N or $CR^4$;

$Y^2$ represents $NR^{4'}$ or $C\ R^4R^{4'}$ provided that $R^{4'}$ is absent when the bond between $Y^1$ and $Y^2$ represents a double bond;

$R^1$ is selected from hydrogen, alkyl, alkenyl, alkynyl, alkoxy, acyl, acylamino, acyloxy, $—(CR^aR^b)_nC(O)R^5$, $—(CR^aR^b)_nNR^6R^7$, aminocarbonyl, alkoxycarbonylamino, alkylsulfonylamino, aminocarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —$SO_3H$, alkylthio, aminosulfonyl, alkylsulfonyl, or nitro;

$R^2$ is selected from hydrogen, alkyl, cycloalkyl, aryl, heterocyclyl or heteroaryl;

$R^3$ is selected from the group consisting of hydrogen, hydroxyalkyl, amino, monoalkylamino, dialkylamino, halogen, perhaloalkyl, cyano, nitro, alkoxyalkyl, carboxy, carboxyalkyl, acyl, aminocarbonyl, alkyl, alkenyl, alkynyl, hydroxyalkyl, carboxyalkyl, haloalkyl and haloalkyloxy;

$R^4$ and $R^{4'}$ are independently selected from the group consisting of hydrogen, halogen, hydroxyl, cyano, alkyl, alkenyl, alkynyl, haloalkyl, hydroxyalkyl, carboxyalkyl, cycloalkyl, cycloalkenyl, cycloalkylalkyl, aryl, arylalkyl, heterocyclyl, heterocyclylalkyl, heteroaryl and heteroarylalkyl;

wherein alkyl, alkenyl, alkynyl, cycloalkyl, cycloalkylalkyl, arylalkyl, aryl, heteroaryl, heteroarylalkyl, heterocyclyl, and heterocyclylalkyl are independently unsubstituted or substituted with upto four substituents independently selected from alkyl, alkenyl, alkynyl, alkoxy, acyl, acyloxy, acylamino, amino, halogen, hydroxy, hydroxyalkyl, keto, thiocarbonyl, carboxy, alkylcarboxy, carboxyalkyl, —$SO_3H$, aminocarbonyl, aminocarbonylamino, alkoxycarbonylamino, hydroxyamino, alkoxyamino, nitro, azido, cyano, cycloalkyl, cycloalkylalkyl, aryl, arylalkyl, heterocyclyl, heterocyclylalkyl, heteroaryl and heteroarylalkyl cycloalkenyl, cycloalkylamino, arylamino, heterocyclylamino, heteroarylamino, cycloalkyloxy, aryloxy, heterocyclyloxy or heteroaryloxy;

Z is a bond or is selected from cycloalkylene, cycloalkylenealkyl, cycloalkenylene, cycloalkyleneoxo, cycloalkyleneamino, arylene, arylenealkyl, arylenethio, aryleneoxy, aryleneamino, arylenealkoxycarbonylamino, arylenesulfonyl, arylenesulfonylamino, heterocyclylene, heterocyclylenealkyl, heterocyclyleneoxy, heterocyclylenealkyloxy, heterocyclyleneamino, heterocyclylenethio, heterocyclylenealkylamino heteroarylene, heteroarylenealkyl, heteroaryleneoxy, heteroaryleneamino, spirocyclyl, $(C_{1-6})$alkylene, $(C_{1-6})$alkenylene or $(C_{1-6})$alkynylene wherein one or more than one methylene groups from alkylene, alkenylene or alkynylene are optionally replaced by hetero atoms or groups such as —O—, —S(O)p, —$N(R^5)$—, or —C(O);

D is a bond or is selected from cycloalkylene, cycloalkenylene, cycloalkylenecarbonyl, cycloalkylenealkoxy, cycloalkyleneamino, arylene, arylenecarbonyl, arylenealkoxycarbonyl, arylenealkoxycarbonylamino, aryleneaminocarbonyl, heterocyclylene, heterocyclylenealkyl, heterocyclylenecarbonyl, heterocyclylenealkylamino, heteroarylene, heteroarylenecarbonyl, heteroarylenealkylamino, $(C_{1-6})$alkylene, $(C_{1-6})$alkenylene or $(C_{1-6})$alkynylene wherein one or more than one methylene groups from alkylene, alkenylene or alkynylene are optionally replaced by hetero atoms or groups such as —O—, —S(O)p-, —$N(R^5)$—, —C(O) or —C(=NR″)— wherein R″ is H, alkyl, cyano, hydroxy, hydroxyalkyl, haloalkyl or perhaloalkyl;

E is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —$(CR^aR^b)_nOR^5$, —$SR^5$, —$(CR^aR^b)_nCOOR^5$, —$(CR^aR^b)_nNR^6R^7$, —$(CR^aR^b)_nC(O)NR^6R^7$, —$(CR^aR^b)_nNR^5C(O)NR^6R^7$, thiocarbonyl, $S(O)_2NR^6R^7$, —$NR^5S(O)_2R^5$, —$S(O)_pR^5$, —$SO_3H$, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;

$R^5$ is selected from the group consisting of hydrogen, —$(CR^aR^b)_nOR^8$, halogen, haloalkyl, —$(CR^aR^b)_nC(O)R^8$, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, $OR^8$, —$OC(O)R^8$, —$(CR^aR^b)_nC(O)NR^6R^7$, —$NR^8C(O)R^8$, —$SR^8$, —$S(O)_pR^8$, —$S(O)_2NR^6R^7$ or —$NR^8S(O)_2R^8$;

$R^6$ and $R^7$ are independently selected from the group consisting of hydrogen, —$(CR^aR^b)_nOR^5$, haloalkyl, —$(CR^aR^b)_nC(O)R^5$, alkyl, alkenyl, alkynyl, aryl, arylalkyl, heteroaryl, heteroarylalkyl, cycloalkyl, cycloalkylalkyl, heterocyclyl and heterocyclylalkyl, or $R^6$ and $R^7$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —$(CR^aR^b)_nOR^5$, —$SR^5$, —$(CR^aR^b)_nNR^6R^7$; oxo, alkylsulfonyl, —$(CR^aR^b)_nCOOR^5$, —$(CR^aR^b)_nC(O)NR^6R^7$, cycloalkyl, cycloalkylalkyl, aryl, arylalkyl, heterocyclyl, heterocyclylalkyl, heteroaryl, or heteroarylalkyl;

Z, D and E may be optionally substituted with one or more substituents independently selected from cyano, nitro, keto, oxo, halogen, haloalkyl, perhaloalkyl, hydroxyamino, —$(CR^aR^b)_nOR^5$, —$(CR^aR^b)_nC(O)R^5$, —$OC(O)R^5$, —$SR^5$, —$(CR^aR^b)_nCOOR^5$, —$(CR^aR^b)_nNR^6R^7$, —$(CR^aR^b)_nC(O)NR^6R^7$, —$(CR^aR^b)_nNR^5C(O)NR^6R^7$, —$NR^5C(O)R^5$, thiocarbonyl, —$S(O)_2NR^6R^7$, —$NR^5S(O)_2R^5$, —$S(O)_pR^5$, —$SO_3H$, —$OP(O)(R^9)_q$, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —$OC(O)R^5$, —$(CR^aR^b)_nC(O)NR^6R^7$, —$NR^5C(O)R^5$, —$SR^5$, —$S(O)_pR^5$, —$S(O)_2NR^6R^7$ or —$NR^5S(O)_2R^5$;

$R^8$ is selected from the group consisting of hydrogen, alkyl, alkoxy, haloalkyl, aryl, arylalkyl, heteroaryl, heteroarylalkyl, cycloalkyl, cycloalkylalkyl, heterocyclyl and heterocyclylalkyl;

wherein alkyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy or carboxyalkyl;

$R^9$ is selected from the group consisting of hydroxy and alkoxy;

$R^a$ and $R^b$ are independently selected from the group consisting of hydrogen, —$OR^5$, halogen, haloalkyl, perhaloalkyl and alkyl;

n is 0-6;

m is 0, 1 or 2;

p is 0, 1 or 2; and q is 1 or 2;

with the proviso that in (IIc) when $Y^5$ is $CR^4$, then $Y^3$ and $Y^4$ cannot be $CR^4$.

According to another embodiment, the present disclosure relates to compounds of formula (I) or its tautomers, polymorphs, stereoisomers, prodrugs, solvate, co-crystals or a pharmaceutically acceptable salts thereof, wherein, A represents a six membered ring which is saturated, unsaturated or partially unsaturated optionally having upto three heteroatoms selected from O, N or S;

B represents a fused heterocycle selected from:

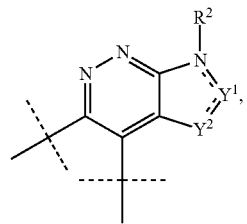 (IIa)

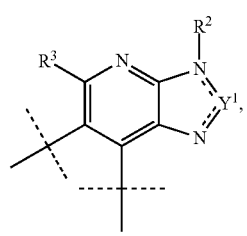 (IIb)

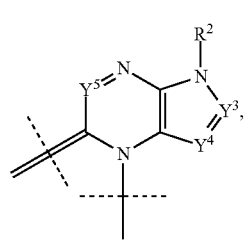 (IIc)

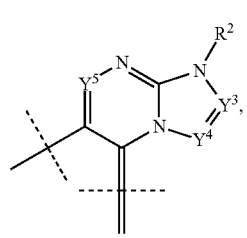 (IId)

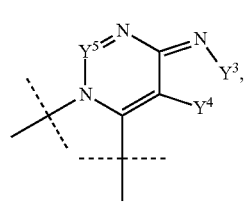 (IIe)

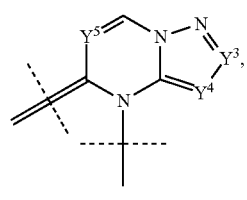 (IIf)

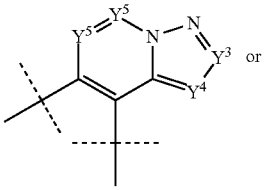 (IIg) or

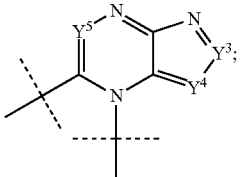 (IIh);

==== represents a single bond or a double bond provided that $R^2$ is absent when the bond between N to which it is attached and $Y^1$ represents a double bond;

$Y^1$, $Y^3$, $Y^4$ and $Y^5$ independently represents N or $CR^4$;

$Y^2$ represents $NR^{4'}$ or $CR^4R^{4'}$ provided that $R^{4'}$ is absent when the bond between $Y^1$ and $Y^2$ represents a double bond;

$R^1$ is selected from hydrogen, alkyl, alkoxy, acyl, acylamino, acyloxy, —$(CR^aR^b)_nC(O)R^5$, —$(CR^aR^b)_nNR^6R^7$, azido, cyano, halogen, hydroxy, hydroxyalkyl, haloalkyl, perhaloalkyl, thiocarbonyl, carboxy, or nitro;

$R^2$ is selected from hydrogen, alkyl, cycloalkyl, aryl, heterocyclyl or heteroaryl;

$R^3$ is selected from the group consisting of hydrogen, hydroxyalkyl, amino, monoalkylamino, dialkylamino, halogen, perhaloalkyl, cyano, nitro, alkoxyalkyl, carboxy, carboxyalkyl, acyl, aminocarbonyl, alkyl, alkenyl, alkynyl, hydroxyalkyl, carboxyalkyl, haloalkyl and haloalkyloxy;

$R^4$ and $R^{4'}$ are independently selected from the group consisting of hydrogen, halogen, hydroxyl, cyano, alkyl, alkenyl, alkynyl, haloalkyl, hydroxyalkyl, carboxyalkyl, cycloalkyl, cycloalkenyl, cycloalkylalkyl, aryl, arylalkyl, heterocyclyl, heterocyclylalkyl, heteroaryl and heteroarylalkyl;

Z is a bond or is selected from cycloalkylene, cycloalkylenealkyl, cycloalkenylene, cycloalkyleneoxo, cycloalkyleneamino, arylene, arylenealkyl, arylenethio, aryleneoxy, aryleneamino, arylenealkoxycarbonylamino, arylenesulfonyl, arylenesulfonylamino, heterocyclylene, heterocyclylenealkyl, heterocyclyleneoxy, heterocyclylenealkyloxy, heterocyclyleneamino, heterocyclylenethio, heterocyclylenealkylamino heteroarylene, heteroarylenealkyl, heteroaryleneoxy, heteroaryleneamino, spirocyclyl, $(C_{1-6})$alkylene, $(C_{1-6})$alkenylene or $(C_{1-6})$alkynylene wherein one or more than one methylene groups from alkylene, alkenylene or alkynylene are optionally replaced by hetero atoms or groups such as —O—, —S(O)p, —N($R^5$)—, or —C(O);

D is a bond or is selected from cycloalkylene, cycloalkenylene, cycloalkylenecarbonyl, cycloalkylenealkoxy, cycloalkyleneamino, arylene, arylenecarbonyl, arylenealkoxycarbonyl, arylenealkoxycarbonylamino, aryleneaminocarbonyl, heterocyclylene, heterocyclylenealkyl, heterocyclylenecarbonyl, heterocyclylenealkylamino, heteroarylene, heteroarylenecarbonyl, heteroarylenealkylamino, $(C_{1-6})$alkylene, $(C_{1-6})$alkenylene or $(C_{1-6})$alkynylene wherein one or more than one methylene groups from alkylene, alkenylene or alkynylene are optionally replaced by hetero atoms or groups such as —O—, —S(O)p-, —N($R^5$)—, —C(O) or —C(=NR'')— wherein R'' is H, alkyl, cyano, hydroxy, hydroxyalkyl, haloalkyl or perhaloalkyl;

E is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —$(CR^aR^b)_nOR^5$, —$SR^5$, —$(CR^aR^b)_nCOOR^5$, —$(CR^aR^b)_nNR^6R^7$, —$(CR^aR^b)_nC(O)$ NR⁶R⁷, —(CRᵃRᵇ)ₙNR⁵C(O)NR⁶R⁷, thiocarbonyl, S(O)₂NR⁶R⁷, —NR⁵S(O)₂R⁵, —S(O)ₚR⁵, —SO₃H, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;

R⁵ is selected from the group consisting of hydrogen, —(CRᵃRᵇ)ₙOR⁸, halogen, haloalkyl, —(CRᵃRᵇ)ₙC(O)R⁸, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR⁸, —OC(O)R⁸, —(CRᵃRᵇ)ₙC(O)NR⁶R⁷, —NR⁸C(O)R⁸, —SR⁸, —S(O)ₚR⁸, —S(O)₂NR⁶R⁷ or —NR⁸S(O)₂R⁸;

R⁶ and R⁷ are independently selected from the group consisting of hydrogen, —(CRᵃRᵇ)ₙOR⁵, haloalkyl, —(CRᵃRᵇ)ₙC(O)R⁵, alkyl, alkenyl, alkynyl, aryl, arylalkyl, heteroaryl, heteroarylalkyl, cycloalkyl, cycloalkylalkyl, heterocyclyl and heterocyclylalkyl, or R⁶ and R⁷ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CRᵃRᵇ)ₙOR⁵, —SR⁵, —(CRᵃRᵇ)ₙNR⁶R⁷, oxo, alkylsulfonyl, —(CRᵃRᵇ)ₙCOOR⁵, —(CRᵃRᵇ)ₙC(O)NR⁶R⁷, cycloalkyl, cycloalkylalkyl, aryl, arylalkyl, heterocyclyl, heterocyclylalkyl, heteroaryl, or heteroarylalkyl;

Z, D and E may be optionally substituted with one or more substituents independently selected from cyano, nitro, keto, oxo, halogen, haloalkyl, perhaloalkyl, hydroxyamino, —(CRᵃRᵇ)ₙOR⁵, —(CRᵃRᵇ)ₙC(O)R⁵, —OC(O)R⁵, —SR⁵, —(CRᵃRᵇ)ₙCOOR⁵, —(CRᵃRᵇ)ₙNR⁶R⁷, —(CRᵃRᵇ)ₙC(O)NR⁶R⁷, —(CRᵃRᵇ)ₙNR⁵C(O)NR⁶R⁷, —NR⁵C(O)R⁵, thiocarbonyl, —S(O)₂NR⁶R⁷, —NR⁵S(O)₂R⁵, —S(O)ₚR⁵, —SO₃H, —OP(O)(R⁹)_q, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R⁵, —(CRᵃRᵇ)ₙC(O)NR⁶R⁷, —NR⁵C(O)R⁵, —SR⁵, —S(O)ₚR⁵, —S(O)₂NR⁶R⁷ or —NR⁵S(O)₂R⁵;

R⁸ is selected from the group consisting of hydrogen, alkyl, alkoxy, haloalkyl, aryl, arylalkyl, heteroaryl, heteroarylalkyl, cycloalkyl, cycloalkylalkyl, heterocyclyl and heterocyclylalkyl;

wherein alkyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy or carboxyalkyl;

R⁹ is selected from the group consisting of hydroxy and alkoxy;

Rᵃ and Rᵇ are independently selected from the group consisting of hydrogen, —OR⁵, halogen, haloalkyl, perhaloalkyl and alkyl;

n is 0-6;

m is 0, 1 or 2;

p is 0, 1 or 2; and q is 1 or 2;

with the proviso that in (IIc) when Y⁵ is CR⁴, then Y³ and Y⁴ cannot be CR⁴.

According to another embodiment, the present disclosure relates to compounds of formula (I) or its tautomers, polymorphs, stereoisomers, prodrugs, solvate, co-crystals or a pharmaceutically acceptable salts thereof, wherein, A represents a six membered ring which is saturated, unsaturated or partially unsaturated optionally having upto three heteroatoms selected from O, N or S;

B represents a fused heterocycle selected from:

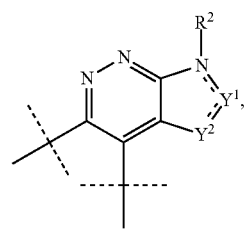

(IIa)

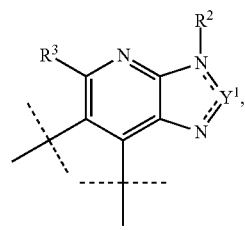

(IIb)

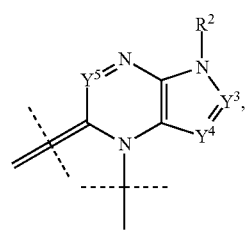

(IIc)

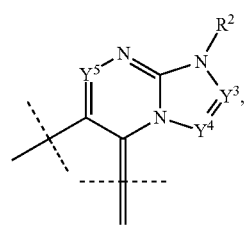

(IId)

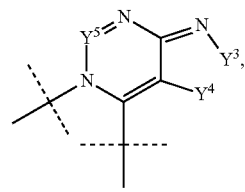

(IIe)

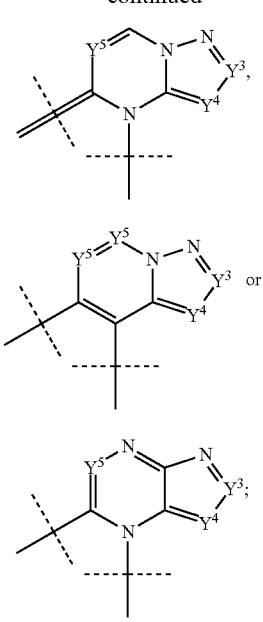

represents a single bond or a double bond provided that R² is absent when the bond between N to which it is attached and Y¹ represents a double bond;

Y¹, Y³, Y⁴ and Y⁵ independently represents N or CR⁴;

Y² represents NR⁴' or C R⁴R⁴' provided that R⁴' is absent when the bond between Y¹ and Y² represents a double bond;

R¹ is selected from hydrogen, alkyl, alkoxy, acyl, acylamino, acyloxy, —(CRᵃRᵇ)ₙC(O)R⁵, —(CRᵃRᵇ)ₙNR⁶R⁷, azido, cyano, halogen, hydroxy, hydroxyalkyl, haloalkyl, perhaloalkyl, thiocarbonyl, carboxy, or nitro;

R² is selected from hydrogen, alkyl;

R³ is selected from the group consisting of hydrogen, amino, halogen, perhaloalkyl, cyano, nitro, carboxy, alkyl;

R⁴ and R⁴' are independently selected from the group consisting of hydrogen, halogen, hydroxyl, cyano, alkyl;

Z is selected from cycloalkylene, cycloalkylenealkyl, cycloalkenylene, arylene, heterocyclylene, heteroarylene, wherein one or more than one methylene groups from alkylene, alkenylene or alkynylene are optionally replaced by hetero atoms or groups such as —O—, —S(O)p, —N(R⁵)—, or —C(O);

D is a bond or is selected from cycloalkylene, cycloalkenylene, arylene, heterocyclylene, heteroarylene, (C₁₋₆)alkylene, (C₁₋₆)alkenylene or (C₁₋₆)alkynylene wherein one or more than one methylene groups from alkylene, alkenylene or alkynylene are optionally replaced by hetero atoms or groups such as —O—, —S(O)p-, —N(R⁵)—, —C(O) or —C(=NR")— wherein R" is H, alkyl, cyano, hydroxy, hydroxyalkyl, haloalkyl or perhaloalkyl;

E is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —(CRᵃRᵇ)ₙOR⁵, —SR⁵, —(CRᵃRᵇ)ₙCOOR⁵, —(CRᵃRᵇ)ₙNR⁶R⁷, —(CRᵃRᵇ)ₙC(O)NR⁶R⁷, —(CRᵃRᵇ)ₙNR⁵C(O)NR⁶R⁷, thiocarbonyl, S(O)₂NR⁶R⁷, —NR⁵S(O)₂R⁵, —S(O)ₚR⁵, —SO₃H, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;

R⁵ is selected from the group consisting of hydrogen, —(CRᵃRᵇ)ₙOR⁸, halogen, haloalkyl, (CRᵃRᵇ)₁C(O)R⁸, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR⁸, —OC(O)R⁸, —(CRᵃRᵇ)ₙC(O)NR⁶R⁷, —NR⁸C(O)R⁸, —SR⁸, —S(O)ₚR⁸, —S(O)₂NR⁶R⁷ or —NR⁸S(O)₂R⁸;

R⁶ and R⁷ are independently selected from the group consisting of hydrogen, —(CRᵃRᵇ)ₙOR⁵, haloalkyl, —(CRᵃRᵇ)ₙC(O)R⁵, alkyl, alkenyl, alkynyl, aryl, arylalkyl, heteroaryl, heteroarylalkyl, cycloalkyl, cycloalkylalkyl, heterocyclyl and heterocyclylalkyl, or R⁶ and R⁷ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CRᵃRᵇ)ₙOR⁵, —SR⁵, —(CRᵃRᵇ)ₙNR⁶R⁷, oxo, alkylsulfonyl, —(CRᵃRᵇ)ₙCOOR⁵, —(CRᵃRᵇ)ₙC(O)NR⁶R⁷, cycloalkyl, cycloalkylalkyl, aryl, arylalkyl, heterocyclyl, heterocyclylalkyl, heteroaryl, or heteroarylalkyl;

Z, D and E may be optionally substituted with one or more substituents independently selected from cyano, nitro, keto, oxo, halogen, haloalkyl, perhaloalkyl, hydroxyamino, —(CRᵃRᵇ)ₙOR⁵, —(CRᵃRᵇ)ₙC(O)R⁵, —OC(O)R⁵, —SR⁵, —(CRᵃRᵇ)ₙCOOR⁵, —(CRᵃRᵇ)ₙNR⁶R⁷, —(CRᵃRᵇ)ₙC(O)NR⁶R⁷, —(CRᵃRᵇ)ₙNR⁵C(O)NR⁶R⁷, —NR⁵C(O)R⁵, thiocarbonyl, —S(O)₂NR⁶R⁷, —NR⁵S(O)₂R⁵, —S(O)ₚR⁵, —SO₃H, —OP(O)(R⁹)q, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R⁵, —(CRᵃRᵇ)ₙC(O)NR⁶R⁷, —NR⁵C(O)R⁵, —SR⁵, —S(O)ₚR⁵, —S(O)₂NR⁶R⁷ or —NR⁵S(O)₂R⁵;

R⁸ is selected from the group consisting of hydrogen, alkyl, alkoxy, haloalkyl, aryl, arylalkyl, heteroaryl, heteroarylalkyl, cycloalkyl, cycloalkylalkyl, heterocyclyl and heterocyclylalkyl;

wherein alkyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy or carboxyalkyl;

R⁹ is selected from the group consisting of hydroxy and alkoxy;

Rᵃ and Rᵇ are independently selected from the group consisting of hydrogen, —OR⁵, halogen, haloalkyl, perhaloalkyl and alkyl;

n is 0-6;

m is 0, 1 or 2;

p is 0, 1 or 2; and q is 1 or 2;

with the proviso that in (IIc) when Y⁵ is CR⁴, then Y³ and Y⁴ cannot be CR⁴.

According to another embodiment, the present disclosure relates to compounds of formula (I) or its tautomers, polymorphs, stereoisomers, prodrugs, solvate, co-crystals or a pharmaceutically acceptable salts thereof, wherein, A represents a six membered ring which is saturated, unsaturated or partially unsaturated optionally having upto three heteroatoms selected from O, N or S;

B represents a fused heterocycle selected from:

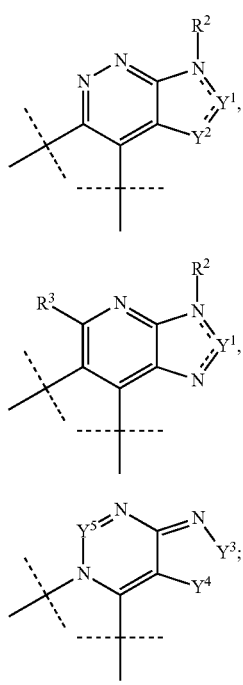

---- represents a single bond or a double bond provided that $R^2$ is absent when the bond between N to which it is attached and $Y^1$ represents a double bond;

$Y^1$, $Y^3$, $Y^4$ and $Y^5$ independently represents N or $CR^4$;

$Y^2$ represents $NR^{4'}$ or C $R^4R^{4'}$ provided that $R^{4'}$ is absent when the bond between $Y^1$ and $Y^2$ represents a double bond;

$R^1$ is selected from hydrogen, alkyl, alkoxy, acyl, acylamino, acyloxy, —$(CR^aR^b)_nC(O)R^5$, —$(CR^aR^b)_nNR^6R^7$, azido, cyano, halogen, hydroxy, hydroxyalkyl, haloalkyl, perhaloalkyl, thiocarbonyl, carboxy, or nitro;

$R^2$ is selected from hydrogen, alkyl;

$R^3$ is selected from the group consisting of hydrogen, amino, halogen, perhaloalkyl, cyano, nitro, carboxy, alkyl;

$R^4$ and $R^{4'}$ are independently selected from the group consisting of hydrogen, halogen, hydroxyl, cyano, alkyl, Z is selected from cycloalkylene, cycloalkenylene, arylene, heterocyclylene, heteroarylene, wherein one or more than one methylene groups from alkylene, alkenylene or alkynylene are optionally replaced by hetero atoms or groups such as —O—, —S(O)p, —N($R^5$)—, or —C(O);

D is a bond or is selected from cycloalkylene, cycloalkenylene, arylene, heterocyclylene, heteroarylene, $(C_{1-6})$alkylene, $(C_{1-6})$alkenylene or $(C_{1-6})$alkynylene wherein one or more than one methylene groups from alkylene, alkenylene or alkynylene are optionally replaced by hetero atoms or groups such as —O—, —S(O)p-, —N($R^5$)—, —C(O) or —C(=NR")— wherein R" is H, alkyl, cyano, hydroxy, hydroxyalkyl, haloalkyl or perhaloalkyl; E is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —$(CR^aR^b)_nOR^5$, —$SR^5$, —$(CR^aR^b)_nCOOR^5$, —$(CR^aR^b)_nNR^6R^7$, —$(CR^aR^b)_nC(O)NR^6R^7$, —$(CR^aR^b)_nNR^5C(O)NR^6R^7$, thiocarbonyl, $S(O)_2NR^6R^7$, —$NR^5S(O)_2R^5$, —$S(O)_pR^5$, —$SO_3H$, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;

$R^5$ is selected from the group consisting of hydrogen, —$(CR^aR^b)_nOR^8$, halogen, haloalkyl, —$(CR^aR^b)_nC(O)R^8$, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, $OR^8$, —$OC(O)R^8$, —$(CR^aR^b)_nC(O)NR^6R^7$, —$NR^8C(O)R^8$, —$SR^8$, —$S(O)_pR^8$, —$S(O)_2NR^6R^7$ or —$NR^8S(O)_2R^8$;

$R^6$ and $R^7$ are independently selected from the group consisting of hydrogen, —$(CR^aR^b)_nOR^5$, haloalkyl, —$(CR^aR^b)_nC(O)R^5$, alkyl, alkenyl, alkynyl, aryl, arylalkyl, heteroaryl, heteroarylalkyl, cycloalkyl, cycloalkylalkyl, heterocyclyl and heterocyclylalkyl, or $R^6$ and $R^7$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —$(CR^aR^b)_nOR^5$, —$SR^5$, —$(CR^aR^b)_nNR^6R^7$, oxo, alkylsulfonyl, —$(CR^aR^b)_nCOOR^5$, —$(CR^aR^b)_nC(O)NR^6R^7$, cycloalkyl, cycloalkylalkyl, aryl, arylalkyl, heterocyclyl, heterocyclylalkyl, heteroaryl, or heteroarylalkyl;

Z, D and E may be optionally substituted with one or more substituents independently selected from cyano, nitro, keto, oxo, halogen, haloalkyl, perhaloalkyl, hydroxyamino, —$(CR^aR^b)_nOR^5$, —$(CR^aR^b)_nC(O)R^5$, —$OC(O)R^5$, —$SR^5$, —$(CR^aR^b)_nCOOR^5$, —$(CR^aR^b)_nNR^6R^7$, —$(CR^aR^b)_nC(O)NR^6R^7$, —$(CR^aR^b)_nNR^5C(O)NR^6R^7$, —$NR^5C(O)R^5$, thiocarbonyl, —$S(O)_2NR^6R^7$, —$NR^5S(O)_2R^5$, —$S(O)_pR^5$, —$SO_3H$, —$OP(O)(R^9)_q$, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —$OC(O)R^5$, —$(CR^aR^b)_nC(O)NR^6R^7$, —$NR^5C(O)R^5$, —$SR^5$, —$S(O)_pR^5$, —$S(O)_2NR^6R^7$ or —$NR^5S(O)_2R^5$;

$R^8$ is selected from the group consisting of hydrogen, alkyl, alkoxy, haloalkyl, aryl, arylalkyl, heteroaryl, heteroarylalkyl, cycloalkyl, cycloalkylalkyl, heterocyclyl and heterocyclylalkyl;

wherein alkyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy or carboxyalkyl;

$R^9$ is selected from the group consisting of hydroxy and alkoxy;

$R^a$ and $R^b$ are independently selected from the group consisting of hydrogen, $-OR^5$, halogen, haloalkyl, perhaloalkyl and alkyl;

n is 0-6;

m is 0, 1 or 2;

p is 0, 1 or 2; and q is 1 or 2;

The present disclosure further relates to the process of preparation of compounds of formula (I) or its tautomers, polymorphs, stereoisomers, prodrugs, solvate, co-crystals or pharmaceutically acceptable salts thereof.

The compounds of formula (I) may be prepared as outlined in the Schemes 1 and 2 below:

Scheme 1:

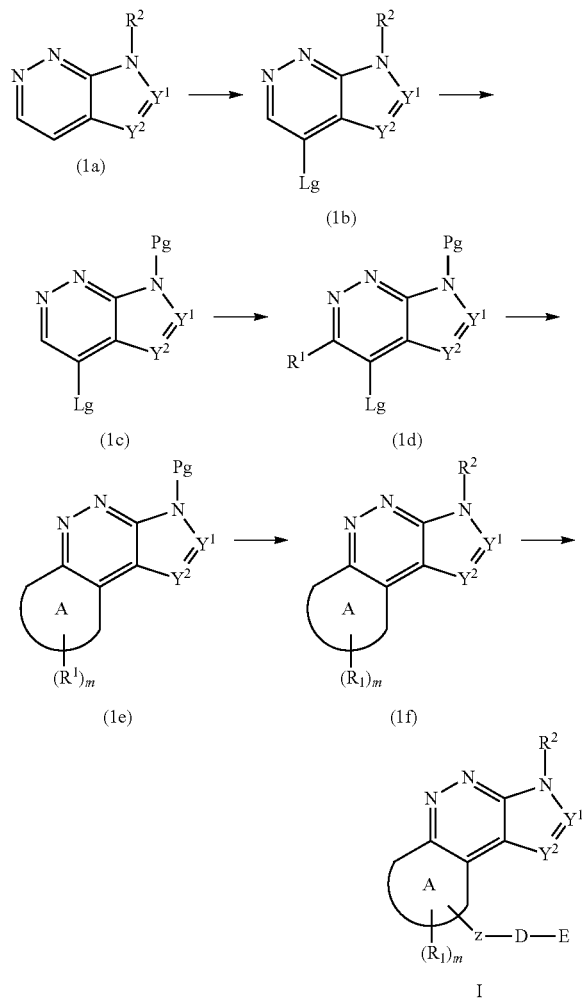

converted to compounds of formula (1d) wherein $R^1$ is selected from $-C(O)H$, $-C(O)OCH_3$, $-C(O)CH=CH_2$, or $-OH$. Compound of formula (1d) may be cyclised to obtained compounds of formula (1e), wherein all symbols are defined herein above, which on deprotection reaction may provide compounds of formula (1f) wherein all symbols are defined herein above. Compounds of formula (1f) may be converted to compounds of formula (I) wherein all symbols are defined herein above.

Scheme-2

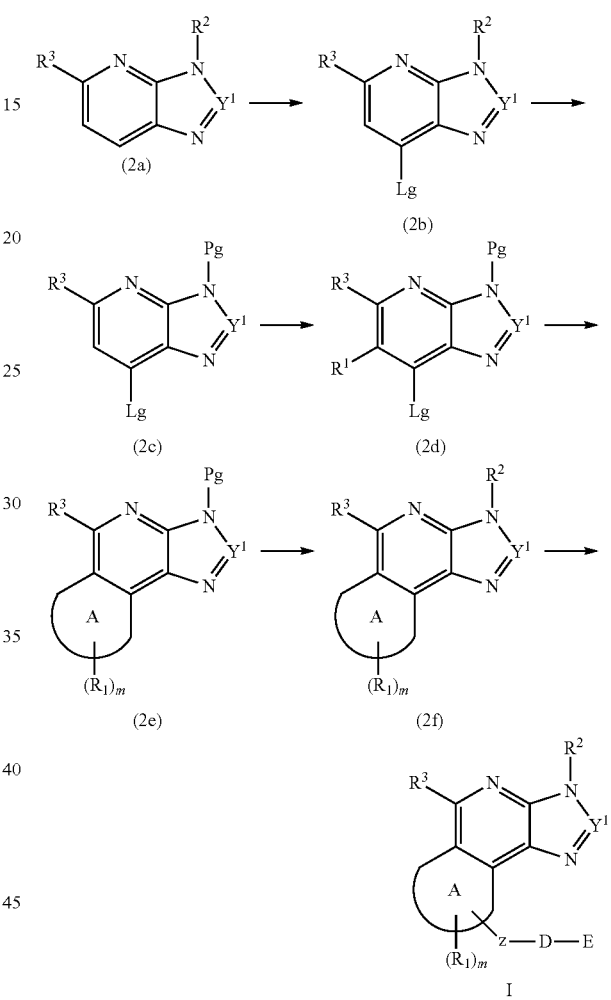

As exemplified in scheme 2 above, compound of formula (2a), wherein $R^2$, $R^3$ and $Y^1$ are defined herein above, which is available commercially or can be prepared by well known methods in the art, may be converted to compounds of formula (2b) wherein Lg is a leaving group selected from halogen, triflate, tosylate or mesylate, preferably halogen and more preferably chlorine. Compounds of formula (2b) may be protected to obtain compounds of formula (2c) by methods well known in the art, wherein Pg is a protecting group such as p-toluene sulphonyl (Ts), methane sulphonyl (Ms), triisopropylsilyl (TIPS), p-methoxy benzyl (PMB), 2-(trimethylsilyl)ethoxymethyl (SEM), methoxymethyl (MOM) and the like. Compound of formula (2c) may be converted to compounds of formula (2d) wherein $R^1$ is selected from $-C(O)H$, $-C(O)OCH_3$, $-C(O)CH=CH_2$, or $-OH$. Compound of formula (2d) may be cyclised to obtained compounds of formula (2e), wherein all symbols are defined herein above, which on deprotection reaction may provide compounds of formula (2f) wherein all sym- As exemplified in scheme 1 above, compound of formula (1a), wherein $R^2$, $Y^1$ and $Y^2$ are defined herein above, which is available commercially or can be prepared by well known methods in the art, may be converted to compounds of formula (1b) wherein Lg is a leaving group selected from halogen, triflate, tosylate or mesylate, preferably halogen and more preferably chlorine. Compounds of formula (1b) may be protected to obtain compounds of formula (1c) by methods well known in the art, wherein Pg is a protecting group such as p-toluene sulphonyl (Ts), methane sulphonyl (Ms), triisopropylsilyl (TIPS), p-methoxy benzyl (PMB), 2-(trimethylsilyl)ethoxymethyl (SEM), Methoxymethyl (MOM) and the like. Compound of formula (1c) may be bols are defined herein above. Compounds of formula (2f) may be converted to compounds of formula (I) wherein all symbols are defined herein above.

Scheme 3:

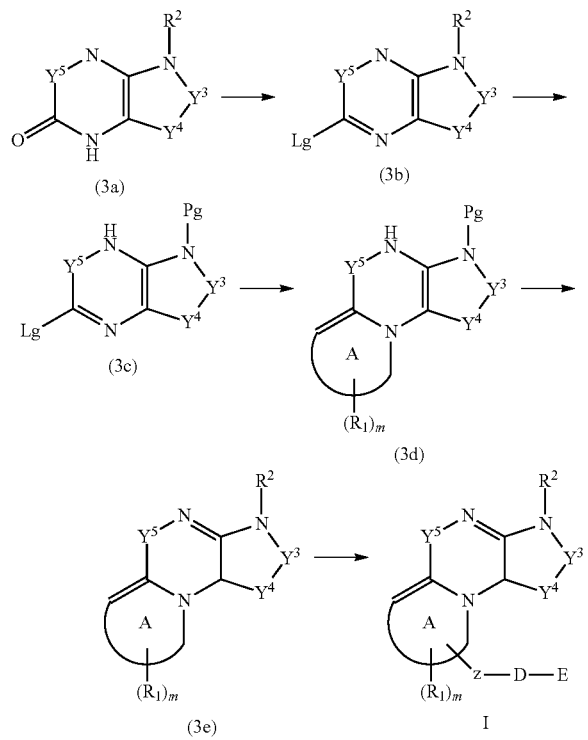

As exemplified in scheme 3 above, compound of formula (3a), wherein $R^2$, $Y^3$, $Y^4$ and $Y^5$ are defined herein above, which is available commercially or can be prepared by well known methods in the art, may be converted to compounds of formula (3b) wherein Lg is a leaving group selected from halogen, triflate, tosylate or mesylate, preferably halogen and more preferably chlorine. Compounds of formula (3b) may be protected to obtain compounds of formula (3c) by methods well known in the art, wherein Pg is a protecting group such as p-toluene sulphonyl (Ts), methane sulphonyl (Ms), triisopropylsilyl (TIPS), p-methoxy benzyl (PMB), 2-(trimethylsilyl)ethoxymethyl (SEM), methoxymethyl (MOM) and the like. Compound of formula (3c) may be converted to compounds of formula (3d) wherein $R^1$ is selected from —C(O)H, —C(O)OCH$_3$, —C(O)CH=CH$_2$, or —OH. Compound of formula (3d) may be cyclised to obtained compounds of formula (3e), wherein all symbols are defined herein above, which on deprotection reaction may provide compounds of formula (3f) wherein all symbols are defined herein above. Compounds of formula (3f) may be converted to compounds of formula (I) wherein all symbols are defined herein above.

Scheme 4:

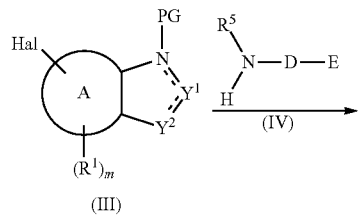

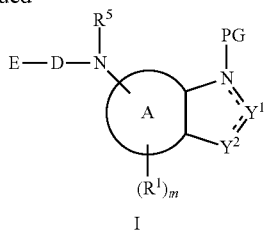

As exemplified in scheme 1 above, compounds of formula (III) wherein Pg is a protecting group such as p-toluene sulphonyl (Ts), methane sulphonyl (Ms), triisopropylsilyl (TIPS), p-methoxy benzyl (PMB), 2-(trimethylsilyl)ethoxymethyl (SEM), methoxymethyl (MOM) and the like and all other symbols are defined herein above, is reacted with an amine of formula (IV) wherein all symbols are defined herein above to provide compounds of formula (I) wherein all symbols are defined herein above.

Scheme 5:

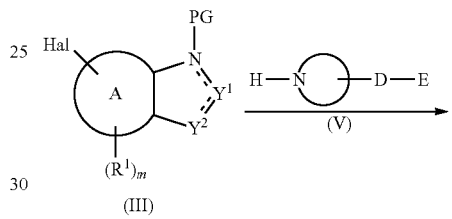

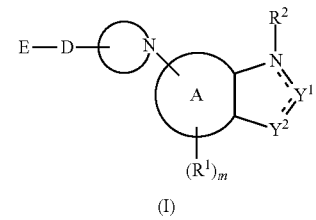

As exemplified in scheme 2 above, compounds of formula (III) wherein Pg is a protecting group such as p-toluene sulphonyl (Ts), methane sulphonyl (Ms), triisopropylsilyl (TIPS), p-methoxy benzyl (PMB), 2-(trimethylsilyl)ethoxymethyl (SEM), methoxymethyl (MOM) and the like and all other symbols are defined herein above, is reacted with an amine of formula (V) wherein all symbols are defined herein above to provide compounds of formula (I) wherein all symbols are defined herein above.

The present disclosure further relates to the process of preparation of compounds of formula (I) or its tautomers, polymorphs, stereoisomers, prodrugs, solvate, co-crystals or pharmaceutically acceptable salts thereof.

It will be appreciated that the compounds of formula (I) may be prepared by derivatisation of formula (I) by transformations well known to those skilled in the art, e.g functional groups as $R^3$ may be transformed to different functional groups such as an ester function being converted to an acid, amide, hydroxyalkyl, keto, aldehyde as well as an ester. The said conversions may be carried out using reagents and conditions well documented in the literature.

Wherever desired or necessary, in any of the above mentioned processes, any of the compounds of formula (I) may be converted into a pharmaceutically acceptable salt or vice versa or converting one salt form into another pharmaceutically acceptable salt form.

According to another embodiment the present invention provides co-crystals comprising a compound of formula (I)

wherein compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula I with the co-crystal former under crystallization conditions and isolating co-crystals thereby formed.

According to another embodiment the present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

Yet another embodiment of the present invention is the use of a compound of the present invention or a pharmaceutically acceptable salt thereof for the manufacture of a medicament for the treatment or prophylaxis of diseases and disorders associated with JAK.

According to another embodiment compositions can be prepared by mixing one or more compounds described herein, or pharmaceutically acceptable salts or tautomers thereof, with pharmaceutically acceptable carriers or the like, to treat or ameliorate a variety of JAK related conditions. The pharmaceutical compositions of the present disclosure can be manufactured by methods well known in the art such as conventional granulating, mixing, dissolving, encapsulating, lyophilizing, emulsifying or levigating processes, among others. The compositions can be in the form of, for example, granules, powders, tablets, capsule syrup, suppositories, injections, emulsions, elixirs, suspensions or solutions. The instant compositions can be formulated for various routes of administration, for example, by oral administration, transmucosal administration, rectal administration, topical administration or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described above, pharmaceutically acceptable excipients and carries are generally known to those skilled in the art and are thus included in the instant invention. Such excipients and carriers are described, for example, in "Remington's Pharmaceutical Sciences" Mack Pub. Co., New Jersey (1991).

The formulations of the invention can be designed for to be short-acting, fast-releasing, long-acting, and, sustained-releasing. Thus, the pharmaceutical formulations can also be formulated for controlled release or for slow release.

The pharmaceutical compositions of the present disclosure can also comprise, for example, micelles or liposomes, or some other encapsulated form, or can be administered in an extended release form to provide a prolonged storage and/or delivery effect. Therefore, the pharmaceutical formulations can be compressed into pellets or cylinders and implanted intramuscularly or subcutaneously as depot injections or as implants such as stents. Such implants can employ known materials such as silicones and biodegradable polymers.

The pharmaceutical compositions may contain, for example, from about 0.1% by weight, to about 90% or more by weight, of the active material, depending on the method of administration. Where the compositions comprise dosage units, each unit can contain, for example, from about 0.1 to 500 mg or more of the active ingredient. The dosage as employed for adult human treatment can range, for example, from about 0.1 to 1000 mg per day, depending on the route and frequency of administration.

Specific dosages can be adjusted depending on conditions of the JAK related condition, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention. Generally, the total daily dose can typically range from about 1 mg/kg/day to about 500 mg/kg/day in single or in divided doses. Typically, dosages for humans can range from about 5 mg to about 100 mg per day, in a single or multiple doses.

A therapeutically effective dose or amount can vary depending upon the route of administration and dosage form. Some compositions of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ can be determined by standard pharmaceutical procedures in animal cell cultures or experimental models.

Also provided is an article of manufacture a pharmaceutical composition comprising a provided compound contained within a packaging material and a label or package insert which indicates that said pharmaceutical composition can be used for treating a JAK related condition, as described herein.

According to another embodiment, compounds of Formula (I) of the invention can be used alone or in combination with one or more additional therapeutic agent selected from the group consisting of cytokine suppressive anti-inflammatory drugs, antibodies to or antagonists of other human cytokines or growth factors, IL-1, IL-2, IL-3, IL-4, IL-5, IL-6, IL-7, IL-8, IL-12, IL-15, IL-16, IL-21, IL-23, interferons, EMAP-II, GM-CSF, FGF, PDGF, CTLA or their ligands including CD 154, Adalimumab, infliximab, golimumab, Certolizumab Pegol, Tocilizumab, CDP 571, soluble p55 or p75 TNF receptors, Etanercept, Lenercept, TNFa converting enzyme inhibitors, IL-1 inhibitors, Interleukin 11, IL-18 antagonists, IL-12 antagonists, IL-12 antibodies, soluble IL-12 receptors, IL-12 binding proteins, non-depleting anti-CD4 inhibitors FK506, rapamycin, mycophenolate mofetil, leflunomide, NSAIDs, ibuprofen, corticosteroids, phosphodiesterase inhibitors, adensosine agonists, anti-thrombotic agents, complement inhibitors, adrenergic agents, IL-Iβ converting enzyme inhibitors, T-cell signalling kinase inhibitors, metalloproteinase inhibitors, sulfasalazine, 6-mercaptopurines, derivatives p75TNFRIgG, sIL-1RI, sIL-1RII, sIL-6R, celecoxib, hydroxychloroquine sulfate, rofecoxib, infliximab, naproxen, valdecoxib, sulfasalazine, meloxicam, acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, anti-IL15, VX-740, Roflumilast, IC-485, CDC-801, S1P1 agonists, FTY720, PKC family inhibitors, Ruboxistaurin, AEB-071, Mesopram, methotrexate, leflunomide, corticosteroids, budenoside, dexamethasone, sulfasalazine, 5-aminosalicylic acid, olsalazine, IL-Iβ converting enzyme inhibitors, IL-lra, T cell signaling inhibitors, tyrosine kinase inhibitors, 6-mercaptopurines, IL-11, mesalamine, prednisone, azathioprine, mercaptopurine, infliximab, methylprednisolone sodium succinate, diphenoxylate/atrop sulfate, loperamide hydrochloride, omeprazole, folate, ciprofloxacin/dextrose-water, hydrocodone, bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone HCl/acetaminophen, promethazine hydrochloride, sodium phosphate, sulfamethoxazole/trimethoprim, polycarbophil, propoxyphene napsylate, hydrocortisone, multivitamins, balsalazide disodium, codeine phosphate/apap, colesevelam HCl, cyanocobalamin, folic acid, levofloxacin, natalizumab, interferon-gamma, methylprednisolone, azathioprine, cyclophosphamide, cyclosporine, methotrexate, 4-aminopyridine, tizanidine, interferon-ia, interferon Beta-1A, interferon-ib, interferon Beta-1B, interferon a-n3, interferon-a, interferon βIA-IF, Peginterferon a 2b, Copolymer 1, glatiramer acetate, hyperbaric oxygen, intravenous immunoglobulin, cladribine, cyclosporine, FK506, mycophenolate mofetil, leflunomide, NSAIDs, corticosteroids, prednisolone, phosphodiesterase inhibitors, adensosine agonists, antithrombotic agents, complement inhibitors, adrenergic agents, antiinflammatory cytokines, interferon-β, IFN ia, IFN ib, Copaxone, corticosteroids, caspase inhibitors, inhibitors of caspase-1, antibodies to CD40 ligand and CD80, alemtuzumab, dronabinol, daclizumab, mitoxantrone, xaliproden hydrochloride, fampridine, glatiramer acetate, natalizumab, sinnabidol, a-immunokine NNS03, ABR-215062, AnergiX.MS, chemokine receptor antagonists, BBR-2778, calagualine, CPI-1189, liposome encapsulated mitoxantrone, THC.CBD, cannabinoid agonists, MBP-8298, mesopram, MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists, interferon gamma antagonist, IL-4 agonists, Diclofenac, Misoprostol, naproxen, Meloxicam, indomethacin, Diclofenac, Methotrexate, Azathioprine, Minocycline, prednisone, etanercept, Rofecoxib, Sulfasalazine, naproxen, leflunomide, methylprednisolone acetate, indomethacin, hydroxychloroquine sulfate, prednisone, sulindac, betamethasone diprop augmented, infliximab, Methotrexate, folate, Triamcinolone acetonide, Diclofenac, dimethylsulfoxide, Piroxicam, Diclofenac Sodium, ketoprofen, Meloxicam, methylprednisolone, nabumetone, tolmetin Sodium, calcipotriene, cyclosporine, Diclofenac Sodium/Misoprostol, fluocinonide, glucosamine sulfate, Sodium gold thiomalate, hydrocodone bitartrate/Apap, Sodium risedronate, sulfadiazine, thioguanine, valdecoxib, alefacept, and efalizumab, Diclofenac, naproxen, ibuprofen, Piroxicam, indomethacin, COX2 Inhibitors, Rofecoxib, valdecoxib, hydroxychloroquine, Steroids, Prednisolone, budenoside, Dexamethasone, cytotoxics, Azathioprine, cyclophosphamide, mycophenolate mofetil, Inhibitors of PDE4, purine synthesis Inhibitor, Sulfasalazine, 5-aminosalicylic acid, olsalazine, azathioprine, CTLA-4-IgG, anti-B7 family antibodies, anti-PD-1 family antibodies, anti-cytokine antibodies, fonotolizumab, Antibody anti-IFNg, anti-receptor receptor antibodies, anti-IL-6 receptor Antibody, antibodies to B-cell Surface molecules, LJP 394, rituximab, anti-CD20 Antibody and B-lymphostat.

In one embodiment, the invention provides methods of treating or preventing a condition associated with JAK in a subject, such as a mammal, i.e., a human or non-human mammal, comprising administering an effective amount of one or more compounds described herein to the subject. The JAK associated condition can be related to JAK1, JAK2, JAK3, and/or Tyk2. Suitable non-human subjects that can be treated include domestic or wild animals, companion animals, such as dogs, cats and the like; livestock, including horses, cows and other ruminants, pigs, poultry, rabbits and the like; primates, for example monkeys, such as macaques including rhesus monkeys and cynomolgus monkeys, marmosets, tamarins and the like, apes, including chimpanzees and orangutans; and rodents, such as rats, mice, gerbils, guinea pigs and the like.

In one embodiment, the compound is administered in a pharmaceutically acceptable form, optionally in a pharmaceutically acceptable carrier.

JAK3 in particular has been implicated in a variety of biological processes. For example, the proliferation and survival of murine mast cells induced by IL-4 and IL-9 have been shown to be dependent on JAK3 and gamma chain-signaling. Suzuki et al., 2000, *Blood* 96, 2172-2180. JAK3 also plays a crucial role in IgE receptor-mediated mast cell degranulation responses (Malaviya et al., 1999, *Biochem. Biophys. Res. Commun.* 257, 807-813), and inhibition of JAK3 kinase has been shown to prevent type I hypersensitivity reactions, including anaphylaxis (Malaviya et al., 1999, *J. Biol. Chem.* 274, 27028-27038). JAK3 inhibition has also been shown to result in immune suppression for allograft rejection (Kirken, (2001), *Transpl. Proc.* 33, 3268-3270). JAK3 kinases have also been implicated in the mechanism involved in, early and late stages of rheumatoid arthritis (Muller-Ladner et al., 2000, *J. Immunal.* 164, 3894-3901); familial amyotrophic lateral sclerosis (Trieu et al., 2000, *Biochem Biophys. Res. Commun.* 267, 22-25); leukemia (Sudbeck et al., 1999, *Clin. Cancer Res.* 5, 1569-1582); mycosis fungoides, a form of T-cell lymphoma (Nielsen et al., 1997, *Prac. Natl. Acad. Sci. USA* 94, 6764-6769); and abnormal cell growth (Yu et al., 1997, *J. Immunol.* 159, 5206-5210; Catlett-Falcone et al., 1999, *Immunity* 10, 105-115).

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., 1996, *Mol. Cell. Biol.* 16, 4710-6; Jurlander et al., 1997, *Blood* 89, 4146-52; Kaneko et al., 1997, *Clin. Exp. Immun.* 109, 185-193; and Nakamura et al., 1996, *J. Biol. Chem.* 271, 19483-8). They are also known to be important to lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating conditions where the function of lymphocytes, macrophages, or mast cells is involved (Kudlacz et al., 2004 *Am. J. Transplant* 4, 51-57; Changelian 2003 *Science* 302, 875-878).

Conditions in which targeting of the JAK pathway or modulation of the JAK kinases, are contemplated to be therapeutically useful include, arthritis, asthma, autoimmune diseases, cancers or tumors, diabetes, certain eye diseases, disorders or conditions, inflammation, intestinal inflammations, allergies or conditions, neurodegenerative diseases, psoriasis, transplant rejection, and viral infection.

Accordingly, the described compounds, pharmaceutically acceptable salts and pharmaceutical compositions can be used to treat a variety of conditions such as the following.

In some embodiments, the methods and compositions of the present invention encompass the treatment of the connective tissue and joint disorders such as arthritis, rheumatoid arthritis, ankylosing spondylitis, fibromyalgia, spondyloarthopathies, gouty arthritis, lumbar spondylarthrosis, carpal tunnel syndrome, psoriatic arthritis, sclerodoma, canine hip dysplasia, systemic lupus erythematosus, juvenile arthritis, osteoarthritis, tendonitis and bursitis.

In other embodiments, the methods and compositions of the present invention encompass the treatment of neuroinflammation and neurodegenerative disorders such as Alzheimer's disease, multiple sclerosis (MS), Parkinson's disease, motor neuron disease, amyotrophic lateral sclerosis, Huntington's disease, cerebral ischemia, neurodegenerative disease caused by traumatic injury, the neurological complications of AIDS, spinal cord injury, and some peripheral, neuropathies and neurodegenerative disorders.

In other embodiments, the methods and compositions of the present invention encompass the treatment of autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be O-cell (humoral) based or T-cell based, including Cogan's syndrome, Wegener's granulomatosis, autoimmune alopecia, and thyroiditis.

In other embodiments, the methods and compositions of the present invention encompass the treatment of diabetes, including Type I diabetes, juvenile onset diabetes and complications from diabetes.

In other embodiments, the methods and compositions of the present invention encompass the treatment of respiratory disorders such as asthma, bronchitis, chronic obstructive pulmonary disease (COPD), airway hyper-responsiveness, bronchial asthma, allergic asthma, intrinsic asthma, extrinsic asthma, dust asthma, cystic fibrosis, pulmonary edema, pulmonary embolism, pneumonia, pulmonary sarcoidosis, silicosis, pulmonary fibrosis, respiratory failure, acute respiratory distress syndrome and emphysema.

In other embodiments, the methods and compositions of the present invention encompass the treatment of the surgical disorders such as pain and swelling following surgery, infection following surgery and inflammation following surgery.

In other embodiments, the methods and compositions of the present invention encompass the treatment of the gastrointestinal disorders such as inflammatory bowel disease, irritable bowel syndrome, Crohn's disease, gastritis, irritable bowel syndrome, diarrhea, constipation, dysentery, ulcerative colitis, gastric esophageal reflux, gastric ulcers, gastric varices, ulcers, heartburn, coeliac diseases, proctitis, eosinophilic gastroenteritis, and mastocytosis.

In other embodiments, the methods and compositions of the present invention encompass the treatment of pain, including but not limited to chronic pain, acute pain, joint pain, nociceptive pain, neuropathic pain, allodynia, hyperalgesia, burn pain, menstrual cramps, kidney stones, headache, migraine headache, sinus headaches, tension headaches, dental pain, myasthenia gravis, multiple sclerosis, sarcoidosis, Behcet's syndrome, myositis, polymyositis, gingivitis, hypersensitivity, swelling occurring after injury, closed head injury, endometriosis, vasculitis, sepsis, glutamate neurotoxicity or hypoxia; ischemic/reperfusion injury in stroke, myocardial ischemica, renal ischemia, heart attacks, stroke, cardiac hypertrophy, coronary artery disease, atherosclerosis and arteriosclerosis, organ hypoxia, and platelet aggregation, stroke, and the like.

Another embodiment provides a method of inhibiting a JAK enzyme, including JAK-1, JAK-2, JAK-3 and/or Tyk-2 that includes contacting the JAK enzyme with either a non-therapeutic amount or a therapeutically effective amount of one or more of the present compounds. Such methods can occur in vivo or in vitro. In vitro contact can involve a screening assay to determine the efficacy of the one or more compounds against a selected enzyme at various amounts or concentrations. In vivo contact with a therapeutically effective amount of the one or more compounds can involve treatment of a described condition or prophylaxis of organ transplant rejection in the animal in which the contact occurs. The effect of the one or more compounds on the JAK enzyme and/or host animal can also be determined or measured.

EXAMPLES

The invention is further illustrated by the following examples which in no way should be construed as being further limiting. One skilled in the art will readily appreciate that the specific methods and results described are merely illustrative.

Preparation 1: 3-Benzenesulfonyl-9-chloro-3H-3,4,5,6-tetraaza-cyclopenta[a]naphthalene (8)

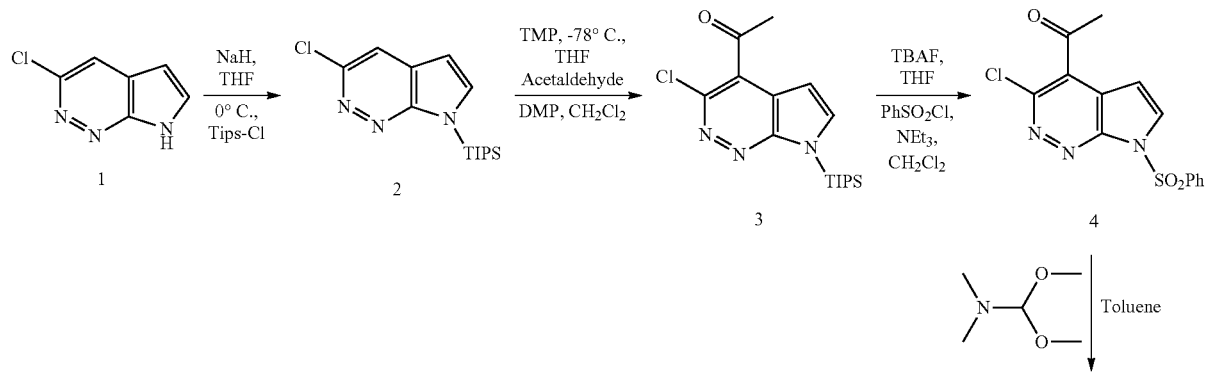

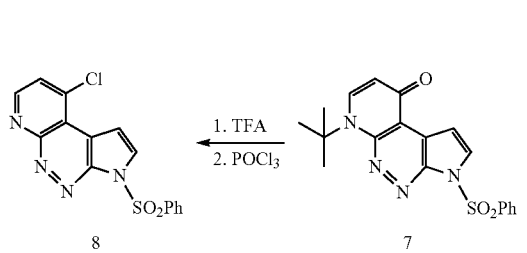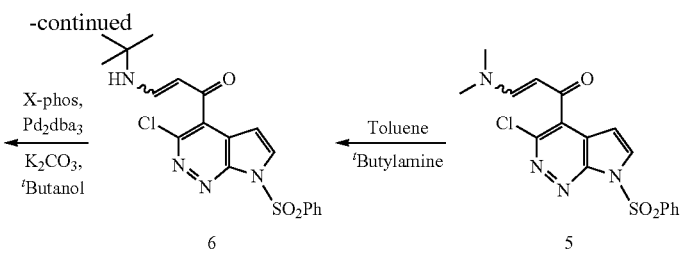

(3-chloropyrrolo[2,3-c]pyridazin-7-yl)-triisopropyl-silane (2)

NaH (1.56 gm, 39.1 mmol) was added portion wise to the solution of 3-chloro-7H-pyrrolo[2,3-c]pyridazine (4.0 gm, 26 mmol, prepared according to the known procedure described in WO 2011 143646) at 0° C. in dry THF (40 ml) and stirred for 10 min. To the reaction mixture, Triisopropylsilyl chloride (6.7 ml, 31.2 mmol) was added drop wise and stirred for 10 min. The reaction mixture was quenched with water and extracted with diethyl ether. The ether layer was washed with brine, dried over sodium sulphate and concentrated under vacuo. The crude material was purified on silica gel column to get the desire product, 7.8 gm as a white solid. $^1$HNMR (400 MHz, CDCl$_3$): ▯1.13 (d, J=7.6 Hz, 18H), 1.89-1.93 (m, 3H), 6.54 (d, J=3.2 Hz, 1H), 7.61 (d, J=3.2 Hz, 1H), 7.65 (s, 1H)

1-(3-chloro-7-triisopropylsilyl-pyrrolo[2,3-c]pyridazin-4-yl)ethanone (3)

Tetramethyl piperidine (6.8 ml, 38.7 mmol) was added to the solution of n-BuLi (24.2 ml, 38.7 mmol, 1.6M solution in THF) in THF (20 ml) at 0° C. and stirred for 30 min. The reaction mixture was cooled to −78° C. and a solution of (3-chloropyrrolo[2,3-c]pyridazin-7-yl)-triisopropyl-silane (6.0 gm, 19.4 mmol) in THF was added and stirred for 45 min. Acetaldehyde (1.3 ml, 23.2 mmol) was added drop wise to the reaction mixture and stirred for 30 min. The reaction mixture was quenched with water and extracted with ethyl acetate. The organic layer was washed with brine, dried over sodium sulphate and concentrated. The solid compound was isolated by washing with diethyl ether-pentane and used for the next reaction, 3.4 gm. The crude hydroxyl compound (3.4 gm, 9.6 mmol) was dissolved in CH$_2$Cl$_2$ (70 ml) and Dess-Martin periodinane reagent (8.1 gm, 19.2 mmol) was added and stirred for 16 hrs. The reaction mixture was quenched with water and extracted with ethyl acetate (150×3 ml). The combined organic layer was washed with brine, dried over sodium sulphate. The solvent was concentrated and crude product was purified on silica gel column to get desire compound, 2.4 gm as off white solid. $^1$HNMR (400 MHz, CDCl$_3$): ▯1.13, d, J=7.6 Hz, 18H), 1.89-1.93 (m, 3H), 2.79 (s, 3H), 6.73 (d, J=3.2 Hz, 1H), 7.70 (d, J=3.6 Hz, 1H)

1-[7-(benzenesulfonyl)-3-chloro-pyrrolo[2,3-c]pyridazin-4-yl]ethanone (4)

Tetrabutyl ammonium floride (10.2 ml, 1M solution in THF) was added to the THF solution of 1-(3-chloro-7-triisopropylsilyl-pyrrolo[2,3-c]pyridazin-4-yl)ethanone (2.4 gm, 6.8 mmol) at 0° C. and stirred for 15 min at room temperature. The reaction mixture was quenched with water and extracted with ethyl acetate (100×2 ml). The combined organic layer was washed with brine, dried over sodium sulphate and concentrated. The crude material was purified by silica gel column chromatography to get the pure compound, 1.2 gm. $^1$HNMR (400 MHz, CDCl$_3$): ▯2.80 (s, 3H), 6.68 (d, J=3.6 Hz, 1H), 7.90 (d, J=3.6 Hz, 1H), 11.62 (br s, 1H).

The above compound (1.2 gm, 6.1 mmol) was dissolved in dichloromethane (25 ml) and was added triethylamine (2.6 ml, 18.0 mmol), DMAP (100 mg, 0.82 mmol) and benzenesulfonyl chloride (0.86 ml, 6.7 mmol). The reaction mixture was stirred 16 h and quenched with NaHCO$_3$ solution and the dichloromethane layer was separated. The aqueous layer was back extracted with dichloromethane (50 ml). The combined organic layer was washed brine and dried over sodium sulphate. The organic layer was concentrated and the crude material was purified on silica gel column to get the desire compound, 1.7 gm. $^1$HNMR (400 MHz, CDCl$_3$): ▯2.74 (s, 3H), 6.75 (d, J=3.6 Hz, 1H), 7.53-7.57 (m, 2H), 7.64-7.68 (m, 1H), 8.09 (d, J=4 Hz, 1H), 8.28-8.30 (m, 2H).

1-(7-Benzenesulfonyl-3-chloro-7H-pyrrolo[2,3-c]pyridazin-4-yl)-3-dimethylamino-propenone (5)

A mixture of 1-[7-(benzenesulfonyl)-3-chloro-pyrrolo[2,3-c]pyridazin-4-yl]ethanone (1.7 gm, 5.0 mmol) and N,N-dimethyl formamide dimethylacetal (1.35 ml, 10.1 mmol) in toluene (20 ml) was heated at 100° C. for 20 h. The reaction mixture was concentrated and the crude material was purified on silica gel column (50-100% ethyl acetate in hexane) to get the desire compound, 1.4 gm as pale yellow solid. $^1$HNMR (400 MHz, CDCl$_3$): ▯▯0.92 (s, 3H), 3.22 (br s, 311), 5.35 (br s, 1H), 6.67 (br s, 1H), 7.51-7.55 (m, 2H), 7.63-7.66 (m, 1H), 7.97 (d, J=4.0 Hz, 1H), 8.27 (d, J=8 Hz, 2H).

1-(7-Benzenesulfonyl-3-chloro-7H-pyrrolo[2,3-c]pyridazin-4-yl)-3-tert-butylamino-propenone (6)

A mixture of 1-(7-Benzenesulfonyl-3-chloro-7H-pyrrolo[2,3-c]pyridazin-4-yl)-3-dimethylamino-propenone (800 mg, 2.0 mmol) and tert-butylamine (0.3 ml, 3.8 mmol) in toluene (20 ml) was heated at 110° C. for 24 h. The reaction mixture was concentrated and the crude material was purified on silica gel column (10-40% ethyl acetate in hexane) to get the desire compound, 250 gm as pale yellow solid. $^1$HNMR (400 MHz, CDCl$_3$): ▯1.39 (s, 9H), 5.35 (d, J 6.8 Hz, 1H), 6.76 (d, J=4.0 Hz, 1H), 7.19 (dd, J=7.2, 13.6 Hz, 1H), 7.52-7.55 (m, 2H), 7.63-7.66 (m, 1H), 7.97 (d, J=4 Hz, 1H), 8.29 (d, J=7.6 Hz, 2H), 10.70 (d, J=13.6 Hz, 1H).

3-Benzenesulfonyl-6-tert-butyl-3,6-dihydro-3,4,5,6-tetraaza-cyclopenta[a]naphthalen-9-one (7)

A solution of 1-(7-Benzenesulfonyl-3-chloro-7H-pyrrolo[2,3-c]pyridazin-4-yl)-3-tert-butylamino-propenone (300 gm, 0.71 mmol) in anhydrous tert-butanol (5 ml) was degassed with N$_2$ for 5 min and were added K$_2$CO$_3$ (197 gm, 1.43 mmol), X-phos (34 mg, 0.07 mmol) and Pd$_2$(dba)$_3$ (32 mg, 0.035 mmol). The reaction mixture was heated for 12 h at 85° C. The reaction mixture was cooled to room temperature and diluted with ethyl acetate and filtered through celite. The filtrate was washed with brine, dried over sodium sulphate and concentrated. The crude material was purified on silica gel column to get the desire compound, 200 gm as off white solid. ¹HNMR (400 MHz, CDCl₃): ☐ 1.97 (s, 9H), 6.35 (d, J=8.0 Hz, 1H), 7.51-7.55 (m, 2H), 7.60-7.61 (m, 1H), 7.87 (d, J=3.6 Hz, 1H), 8.09 (d, J=3.6 Hz, 1H), 8.13 (d, J=8.4 Hz, 1H), 8.28 (d, J=7.6 Hz, 2H).

3-Benzenesulfonyl-9-chloro-3H-3,4,5,6-tetraaza-cyclopenta[a]naphthalene (8)

A mixture 3-Benzenesulfonyl-6-tert-butyl-3,6-dihydro-3,4,5,6-tetraaza-cyclopenta[a]naphthalen-9-one (200 mg, 0.52 mmol) and TFA (2 ml) was heated for 1 hr at 60° C. The reaction mixture was concentrated and quenched with saturated NaHCO₃ solution. The resulting solid was filtered, washed with water, dried under vacuum to get the desire compound, 165 mg as off white solid. ¹HNMR (400 MHz, DMSOd₆): ☐ 6.21 (d, J=7.2 Hz, 1H), 7.59 (d, J=3.6 Hz, 1H), 7.64-7.68 (m, 2H), 7.74-7.78 (m, 1H), 8.12 (d, 0.1=7.2 Hz, 1H), 8.19 (d, J 7.6 Hz, 2H), 8.46 (d, 0.1=3.6 Hz, 1H), 12.86 (br s, 1H). The crude material (160 mg, 0.5 mmol) was heated with POCl₃ (2 ml) for 20 min at 110° C. The excess POCl₃ was removed under reduce pressure and the residue obtained was quenched with saturated NaHCO₃ solution, extracted with 5% methanol in dichloromethane (50×3 ml). The combined organic layer was dried over sodium sulphate and concentrated. The crude material was purified on silica gel to get 80 mg of desire compound. ¹HNMR (400 MHz, CDCl₃): ☐ 7.53-7.57 (m, 2H), 7.61-7.65 (m, 1H), 7.67 (d, J=3.6 Hz, 1H), 7.77 (d, 0.1=4.8 Hz, 1H), 8.23 (d, J=3.6 Hz, 1H), 8.39-8.42 (m, 2H), 9.13 (d, J=4.4 Hz, 1H).

R = 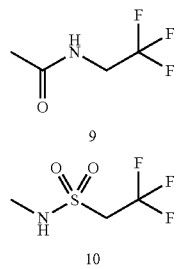

1-(3H-3,4,5,6-Tetraaza-cyclopenta[a]naphthalen-9-yl)-piperidine-3-carboxylic acid (2,2,2-trifluoro-ethyl)-amide (9)

A mixture of 3-Benzenesulfonyl-9-chloro-3H-3,4,5,6-tetraaza-cyclopenta[a]naphthalene 8 (10 mg, 0.035 mmol) and N-(2,2,2-trifluoroethyl)piperidine-3-carboxamide (38 mg, 0.18 mmol) was heated (neat) at 135° C. for 5 h. Reaction mixture was purified to afford the pure product. ¹HNMR (400 MHz, CD₃OD): ☐ 1.67-1.77 (m, 1H), 1.96-2.0 (m, 1H), 2.10-2.20 (m, 1H), 2.62-2.72 (m, 1H), 2.91-3.02 (m, 2H), 3.57-3.69 (m, 2H), 3.82-4.00 (m, 3H), 7.25 (br s, 1H), 7.35 (d, J=5.2 Hz, 1H), 8.0 (d, J=2.8 Hz, 1H), 8.99 (br s, 1H).

2,2,2-Trifluoro-ethanesulfonic acid[1-(3H-3,4,5,6-tetraaza-cyclopenta[a]naphthalen-9-yl)-piperidin-3-yl]-amide (10)

A mixture of 3-Benzenesulfonyl-9-chloro-3H-3,4,5,6-tetraaza-cyclopenta[a]naphthalene 8 (15 mg, 0.043 mmol) and 2,2,2-trifluoro-N-(3-piperidyl)ethanesulfonamide (55 mg, 0.22 mmol) was heated (neat) at 135° C. for 5 h. Reaction mixture was purified to afford the pure product. ¹HNMR (400 MHz, CD3OD): ☐ 1.46-1.62 (m, 1H), 1.96-206 (m, 2H), 2.22-2.32 (m, 1H), 2.56-2.74 (m, 2H), 3.50-3.60 (m, 1H), 3.72-3.80 (m, 1H), 3.84-3.94 (m, 1H), 4.15-4.23 (m, 2H), 7.29 (d, J=2.8 Hz, 1H), 7.35 (d, J=5.2 Hz, 1H), 8.01 (d, J=3.2 Hz, 1H), 8.89 (br s, 1H)

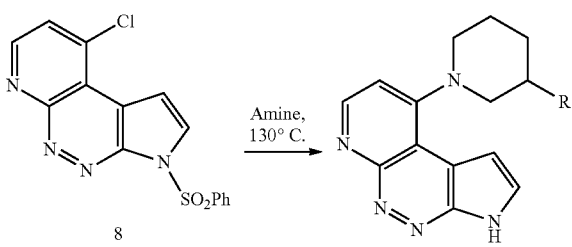

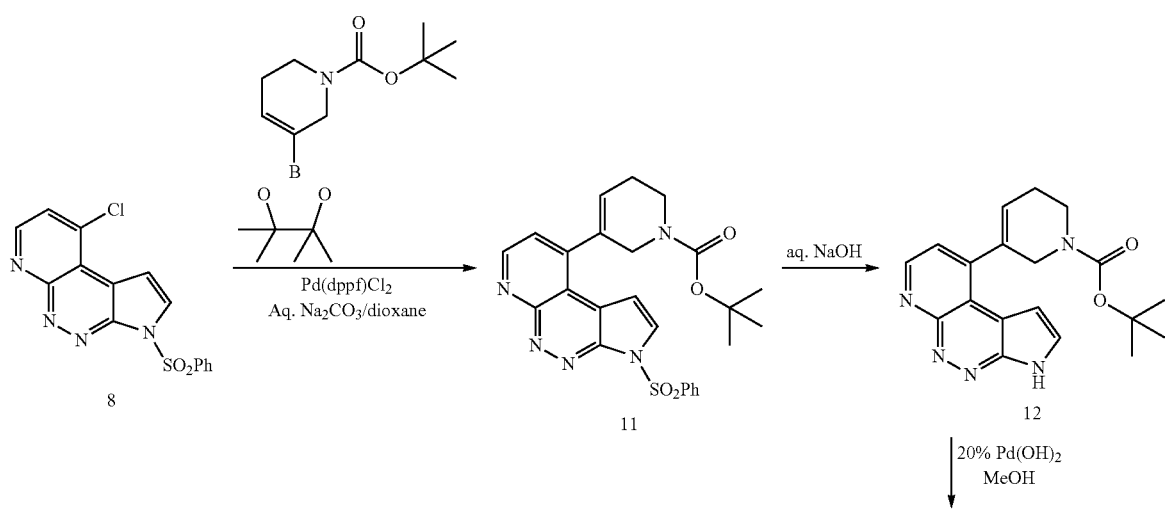

-continued

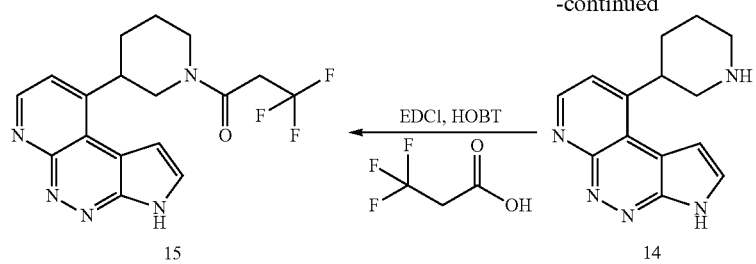 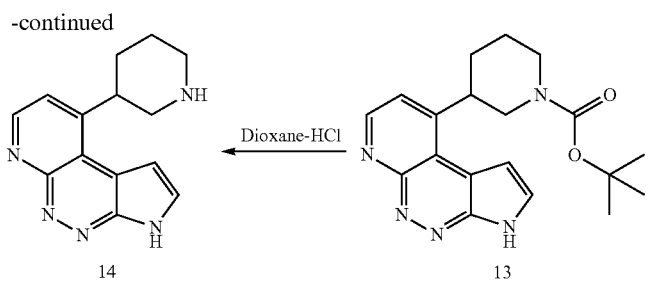

5-(3-Benzenesulfonyl-3H-3,4,5,6-tetraaza-cyclopenta[a]naphthalen-9-yl)-3,6-dihydro-2H-pyridine-1-carboxylic acid tert-butyl ester (11)

To a degassed solution of compound 8 (70 g, 0.203 mmol), tert-butyl 5-(3,3,4,4-tetramethylborolan-1-yl)-3,6-dihydro-2H-pyridine-1-carboxylate (126 mg, 0.406 mmol) in dioxane (4 mL) was added aq. $Na_2CO_3$ (2.5 M, 0.61 mmol, 0.25 mL) and $Pd(dppf)Cl_2$ (30 mg, 0.036 mmol) under nitrogen atmosphere. It was heated at 90° C. for 5 h. Water was added to it and extracted with ethyl acetate. Organic layer was dried over sodium sulphate filtered and concentrated under vacuum. Residue obtained was purified by column chromatography to get the desire compound. $^1$HNMR (400 MHz, $CDCl_3$): δ 1.59 (s, 9H), 2.40-2.45 (m, 2H), 3.94-4.29 (m, 4H), 5.99 (s, 1H), 7.01 (d, J 4 Hz, 1H), 7.48 (d, J=4 Hz, 1H), 7.51-7.55 (m, 2H), 7.62-7.64 (m, 1H), 8.08 (d, J=3.6 Hz, 1H), 8.40 (d, J 8 Hz, 2H), 9.18 (d, J 4.4 Hz, 1H).

5-(3H-3,4,5,6-Tetraaza-cyclopenta[a]naphthalen-9-yl)-3,6-dihydro-2H-pyridine-1-carboxylic acid tert-butylester (12)

To a solution of compound 11 (30 mg, 0.061 mmol) in Acetone (3 mL) and aqueous NaOH (7 mg, 0.175 mmol dissolved in 0.1 mL of water), was heated for 3 h at 60° C. The reacted mixture was concentrated, diluted with 5% MeOH/DCM, washed with brine and dried over sodium sulphate. Organic layer was concentrated and residue was purified by column chromatography to get the desire compound. $^1$HNMR (400 MHz, $CDCl_3$): δ 1.63 (s, 9H), 2.42-2.50 (m, 2H), 4.12-4.41 (m, 4H), 6.07 (s, 1H), 7.02 (d, J=3.2 Hz, 1H), 7.50 (d, J=4.4 Hz, 1H), 7.92 (br s, 1H), 9.17 (d, J=4 Hz, 1H), 12.19 (br s).

3,3,3-Trifluoro-1-[3-(3H-3,4,5,6-tetraaza-cyclopenta[a]naphthalen-9-yl)-piperidin-1-yl]-propan-1-one (15)

To a solution of compound 12 (30 mg, 0.061 mmol) in MeOH (3 mL) and 20% $Pd(OH)_2$ (10 mg) was added. It was degassed, purged with hydrogen and stirred under hydrogen atmosphere for 16 h and again another 5 mg $Pd(OH)_2$ was added and continued for further 5 h. Reaction mixture was filtered through celite pad and it was washed with 50% methanol in dichloromethane (250 mL). Organic layer was concentrated and residue was passed through very short silica get column (eluted with 1-5% MeOH in ethyl acetate) to remove the polar impurity. The solvent was concentrated and the crude residue (13) obtained was stirred with dioxane-HCl (0.5 ml, 4M solution) for 1 h. The reaction was concentrated, dried under vacuum and used directly for next reaction. The crude amine (14) was suspended in dichloromethane and 0.2 ml of triethylamine was added and cooled to ice-water temperature. A solution of 3,3,3-trifluoropropanoic acid (28 mg, 0.16 mmol) in dichloromethane, EDCI (35 mg, 0.193 mmol) and HOBT (27 mg, 0.193 mmol) were added to the reaction mixture. The reaction was stirred for 4 h at room temperature, quenched with water, extracted 5% MeOH in dichloromethane (50×2 ml). The combined organic layer was dried over sodium sulphate and concentrated. The crude material was purified to get the desire compound. $^1$HNMR (400 MHz, MeOH-$d_4$): δ 1.82-2.05 (m, 1H), 2.24-2.55 (m, 2H), 2.74-2.87 (m, 1H), 3.25-3.51 (m, 1H), 3.92-4.133 (m, 3H), 4.23-4.36 (m, 1H), 4.52-4.71 (m, 1H), 7.64-7.67 (m, 1H), 8.18-8.24 (m, 1H), 8.50-8.53 (m, 1H), 9.5 (br s, 1H).

The below list of examples, but not to be limited to these numbers, can also be synthesized by following the general synthesis described above:

3-Oxo-3-[3-(3H-3,4,5,6-tetraaza-cyclopenta[a]naphthalen-9-yl)-piperidin-1-yl]-propionitrile,
4,4,4-Trifluoro-1-[3-(3H-3,4,5,6-tetraaza-cyclopenta[a]naphthalen-9-yl)-piperidin-1-yl]-butan-1-one,
[3-(3H-3,4,5,6-Tetraaza-cyclopenta[a]naphthalen-9-yl)-piperidine-1-sulfonyl]-acetonitrile,
9-[1-(2,2,2-Trifluoro-ethanesulfonyl)-piperidin-3-yl]-3H-3,4,5,6-tetraaza-cyclopenta[a]naphthalene,
3-[4-Methyl-3-(3H-3,4,5,6-tetraaza-cyclopenta[a]naphthalen-9-yl)-piperidin-1-yl]-3-oxo-propionitrile,
3-Oxo-3-[3-(3H-3,4,5,6-tetraaza-cyclopenta[a]naphthalen-9-yl)-pyrrolidin-1-yl]-propionitrile,
3,3,3-Trifluoro-1-[3-(3H-3,4,5,6-tetraaza-cyclopenta[a]naphthalen-9-yl)-pyrrolidin-1-yl]-propan-1-one,
4,4,4-Trifluoro-1-[3-(3H-3,4,5,6-tetraaza-cyclopenta[a]naphthalen-9-yl)-pyrrolidin-1-yl]-butan-1-one,
[3-(3H-3,4,5,6-Tetraaza-cyclopenta[a]naphthalen-9-yl)-pyrrolidine-1-sulfonyl]-acetonitrile,
9-[1-(2,2,2-Trifluoro-ethanesulfonyl)-pyrrolidin-3-yl]-3H-3,4,5,6-tetraaza-cyclopenta[a]naphthalene,
9-(1-Methanesulfonyl-pyrrolidin-3-yl)-3H-3,4,5,6-tetraaza-cyclopenta[a]naphthalene,
3,3,3-Trifluoro-1-[3-(3H-3,4,5,6,8-pentaaza-cyclopenta[a]naphthalen-9-yl)-piperidin-1-yl]-propan-1-one,
3-Oxo-3-[3-(3H-3,4,5,6,8-pentaaza-cyclopenta[a]naphthalen-9-yl)-piperidin-1-yl]-propionitrile,
4,4,4-Trifluoro-1-[3-(3H-3,4,5,6,8-pentaaza-cyclopenta[a]naphthalen-9-yl)-piperidin-1-yl]-butan-1-one,
[3-(3H-3,4,5,6,8-Pentaaza-cyclopenta[a]naphthalen-9-yl)-piperidine-1-sulfonyl]-acetonitrile,
9-[1-(2,2,2-Trifluoro-ethanesulfonyl)-piperidin-3-yl]-3H-3,4,5,6,8-pentaaza-cyclopenta[a]naphthalene,
9-(1-Methanesulfonyl-piperidin-3-yl)-3H-3,4,5,6,8-pentaaza-cyclopenta[a]naphthalene,
3-Oxo-3-[3-(3H-3,4,5,6,8-pentaaza-cyclopenta[a]naphthalen-9-yl)-pyrrolidin-1-yl]-propionitrile, 3,3,3-Trifluoro-1-[3-(3H-3,4,5,6,8-pentaaza-cyclopenta[a]naphthalen-9-yl)-pyrrolidin-1-yl]-propan-1-one,
4,4,4-Trifluoro-1-[3-(3H-3,4,5,6,8-pentaaza-cyclopenta[a]naphthalen-9-yl)-pyrrolidin-1-yl]-butan-1-one,
[3-(3H-3,4,5,6,8-Pentaaza-cyclopenta[a]naphthalen-9-yl)-pyrrolidine-1-sulfonyl]-acetonitrile,
9-[1-(2,2,2-Trifluoro-ethanesulfonyl)-pyrrolidin-3-yl]-3H-3,4,5,6,8-pentaaza-cyclopenta[a]naphthalene,
9-(1-Methanesulfonyl-pyrrolidin-3-yl)-3H-3,4,5,6,8-pentaaza-cyclopenta[a]naphthalene,
3,3,3-Trifluoro-1-[3-(7-methyl-3H-3,4,5,6,8-pentaaza-cyclopenta[a]naphthalen-9-yl)-piperidin-1-yl]-propan-1-one,
3-[3-(7-Methyl-3H-3,4,5,6,8-pentaaza-cyclopenta[a]naphthalen-9-yl)-piperidin-1-yl]-3-oxo-propionitrile,
4,4,4-Trifluoro-1-[3-(7-methyl-3H-3,4,5,6,8-pentaaza-cyclopenta[a]naphthalen-9-yl)-piperidin-1-yl]-butan-1-one,
[3-(7-Methyl-3H-3,4,5,6,8-pentaaza-cyclopenta[a]naphthalen-9-yl)-piperidine-1-sulfonyl]-acetonitrile,
7-Methyl-9-[1-(2,2,2-trifluoro-ethanesulfonyl)-piperidin-3-yl]-3H-,4,5,6,8-pentaaza-cyclopenta[a]naphthalene,
3-[3-(7-Methyl-3H-3,4,5,6,8-pentaaza-cyclopenta[a]naphthalen-9-yl)-pyrrolidin-1-yl]-3-oxo-propionitrile,
3,3,3-Trifluoro-1-[3-(7-methyl-3H-3,4,5,6,8-pentaaza-cyclopenta[a]naphthalen-9-yl)-pyrrolidin-1-yl]-propan-1-one,
4,4,4-Trifluoro-1-[3-(7-methyl-3H-3,4,5,6,8-pentaaza-cyclopenta[a]naphthalen-9-yl)-pyrrolidin-1-yl]-butan-1-one,
[3-(7-Methyl-3H-3,4,5,6,8-pentaaza-cyclopenta[a]naphthalen-9-yl)-pyrrolidine-1-sulfonyl]-acetonitrile,
7-Methyl-9-[1-(2,2,2-trifluoro-ethanesulfonyl)-pyrrolidin-3-yl]-3H-,4,5,6,8-pentaaza-cyclopenta[a]naphthalene,
3,3,3-Trifluoro-1-[3-(3H-3,4,5,7,8-pentaaza-cyclopenta[a]naphthalen-9-yl)-piperidin-1-yl]-propan-1-one,
3-Oxo-3-[3-(3H-3,4,5,7,8-pentaaza-cyclopenta[a]naphthalen-9-yl)-piperidin-1-yl]-propionitrile,
4,4,4-Trifluoro-1-[3-(3H-3,4,5,7,8-pentaaza-cyclopenta[a]naphthalen-9-yl)-piperidin-1-yl]-butan-1-one,
[3-(3H-3,4,5,7,8-Pentaaza-cyclopenta[a]naphthalen-9-yl)-piperidine-1-sulfonyl]-acetonitrile,
9-[1-(2,2,2-Trifluoro-ethanesulfonyl)-piperidin-3-yl]-3H-3,4,5,7,8-pentaaza-cyclopenta[a]naphthalene,
9-(1-Methanesulfonyl-piperidin-3-yl)-3H-3,4,5,7,8-pentaaza-cyclopenta[a]naphthalene,
3,3,3-Trifluoro-1-[3-(3H-3,4,5,7,8-pentaaza-cyclopenta[a]naphthalen-9-yl)-pyrrolidin-1-yl]-propan-1-one,
3-Oxo-3-[3-(3H-3,4,5,7,8-pentaaza-cyclopenta[a]naphthalen-9-yl)-pyrrolidin-1-yl]-propionitrile,
4,4,4-Trifluoro-1-[3-(3H-3,4,5,7,8-pentaaza-cyclopenta[a]naphthalen-9-yl)-pyrrolidin-1-yl]-butan-1-one,
[3-(3H-3,4,5,7,8-Pentaaza-cyclopenta[a]naphthalen-9-yl)-pyrrolidine-1-sulfonyl]-acetonitrile,
9-[1-(2,2,2-Trifluoro-ethanesulfonyl)-pyrrolidin-3-yl]-3H-3,4,5,7,8-pentaaza-cyclopenta[a]naphthalene,
9-(1-Methanesulfonyl-pyrrolidin-3-yl)-3H-3,4,5,7,8-pentaaza-cyclopenta[a]naphthalene,
3-Oxo-3-[3-(3H-3,4,5,6,7-pentaaza-cyclopenta[a]naphthalen-9-yl)-piperidin-1-yl]-propionitrile,
3,3,3-Trifluoro-1-[3-(3H-3,4,5,6,7-pentaaza-cyclopenta[a]naphthalen-9-yl)-piperidin-1-yl]-propan-1-one,
4,4,4-Trifluoro-1-[3-(3H-3,4,5,6,7-pentaaza-cyclopenta[a]naphthalen-9-yl)-piperidin-1-yl]-butan-1-one,
[3-(3H-3,4,5,6,7-Pentaaza-cyclopenta[a]naphthalen-9-yl)-piperidine-1-sulfonyl]-acetonitrile,
9-[1-(2,2,2-Trifluoro-ethanesulfonyl)-piperidin-3-yl]-3H-3,4,5,6,7-pentaaza-cyclopenta[a]naphthalene,
9-(1-Methanesulfonyl-piperidin-3-yl)-3H-3,4,5,6,7-pentaaza-cyclopenta[a]naphthalene,
3,3,3-Trifluoro-1-[3-(3H-3,4,5,6,7-pentaaza-cyclopenta[a]naphthalen-9-yl)-pyrrolidin-1-yl]-propan-1-one,
3-Oxo-3-[3-(3H-3,4,5,6,7-pentaaza-cyclopenta[a]naphthalen-9-yl)-pyrrolidin-1-yl]-propionitrile,
4,4,4-Trifluoro-1-[3-(3H-3,4,5,6,7-pentaaza-cyclopenta[a]naphthalen-9-yl)-pyrrolidin-1-yl]-butan-1-one,
[3-(3H-3,4,5,6,7-Pentaaza-cyclopenta[a]naphthalen-9-yl)-pyrrolidine-1-sulfonyl]-acetonitrile,
9-[1-(2,2,2-Trifluoro-ethanesulfonyl)-pyrrolidin-3-yl]-3H-3,4,5,6,7-pentaaza-cyclopenta[a]naphthalene,
9-(1-Methanesulfonyl-pyrrolidin-3-yl)-3H-3,4,5,6,7-pentaaza-cyclopenta[a]naphthalene,
3,3,3-Trifluoro-1-[3-(3H-3,4,5,7-tetraaza-cyclopenta[a]naphthalen-9-yl)-piperidin-1-yl]-propan-1-one,
4,4,4-Trifluoro-1-[3-(3H-3,4,5,7-tetraaza-cyclopenta[a]naphthalen-9-yl)-piperidin-1-yl]-butan-1-one,
[3-(3H-3,4,5,7-Tetraaza-cyclopenta[a]naphthalen-9-yl)-piperidine-1-sulfonyl]-acetonitrile,
9-[1-Trifluoro-ethanesulfonyl)-piperidin-3-yl]-3H-3,4,5,7-tetraaza-cyclopenta[a]naphthalene,
9-(1-Methanesulfonyl-piperidin-3-yl)-3H-3,4,5,7-tetraaza-cyclopenta[a]naphthalene,
3,3,3-Trifluoro-1-[3-(3H-3,4,5,8-tetraaza-cyclopenta[a]naphthalen-9-yl)-piperidin-1-yl]-propan-1-one,
3-Oxo-3-[3-(3H-3,4,5,8-tetraaza-cyclopenta[a]naphthalen-9-yl)-piperidin-1-yl]-propionitrile,
4,4,4-Trifluoro-1-[3-(3H-3,4,5,8-tetraaza-cyclopenta[a]naphthalen-9-yl)-piperidin-1-yl]-butan-1-one,
9-[1-(2,2,2-Trifluoro-ethanesulfonyl)-piperidin-3-yl]-3H-3,4,5,8-tetraaza-cyclopenta[a]naphthalene,
[3-(3H-3,4,5,8-Tetraaza-cyclopenta[a]naphthalen-9-yl)-piperidine-1-sulfonyl]-acetonitrile,
9-(1-Methanesulfonyl-piperidin-3-yl)-3H-3,4,5,8-tetraaza-cyclopenta[a]naphthalene,
3-Oxo-3-[3-(3H-3,4,5,7-tetraaza-cyclopenta[a]naphthalen-9-yl)-pyrrolidin-1-yl]-propionitrile,
3,3,3-Trifluoro-1-[3-(3H-3,4,5,7-tetraaza-cyclopenta[a]naphthalen-9-yl)-pyrrolidin-1-yl]-propan-1-one,
4,4,4-Trifluoro-1-[3-(3H-3,4,5,7-tetraaza-cyclopenta[a]naphthalen-9-yl)-pyrrolidin-1-yl]-butan-1-one,
[3-(3H-3,4,5,7-Tetraaza-cyclopenta[a]naphthalen-9-yl)-pyrrolidine-1-sulfonyl]-acetonitrile,
9-[1-(2,2,2-Trifluoro-ethanesulfonyl)-pyrrolidin-3-yl]-3H-3,4,5,7-tetraaza-cyclopenta[a]naphthalene,
9-(1-Methanesulfonyl-pyrrolidin-3-yl)-3H-3,4,5,7-tetraaza-cyclopenta[a]naphthalene,
3,3,3-Trifluoro-1-[3-(3H-3,4,5,8-tetraaza-cyclopenta[a]naphthalen-9-yl)-pyrrolidin-1-yl]-propan-1-one,
3-Oxo-3-[3-(3H-3,4,5,8-tetraaza-cyclopenta[a]naphthalen-9-yl)-pyrrolidin-1-yl]-propionitrile,
4,4,4-Trifluoro-1-[3-(3H-3,4,5,8-tetraaza-cyclopenta[a]naphthalen-9-yl)-pyrrolidin-1-yl]-butan-1-one,
9-[1-(2,2,2-Trifluoro-ethanesulfonyl)-pyrrolidin-3-yl]-3H-3,4,5,8-tetraaza-cyclopenta[a]naphthalene,
[3-(3H-3,4,5,8-Tetraaza-cyclopenta[a]naphthalen-9-yl)-pyrrolidine-1-sulfonyl]-acetonitrile,
9-(1-Methanesulfonyl-pyrrolidin-3-yl)-3H-3,4,5,8-tetraaza-cyclopenta[a]naphthalene,
1-(3H-3,4,5,6-Tetraaza-cyclopenta[a]naphthalen-9-yl)-piperidine-3-carboxylic acid cyanomethyl-amide,
1-(3H-3,4,5,6-Tetraaza-cyclopenta[a]naphthalen-9-yl)-piperidine-3-carboxylic acid (3,3,3-trifluoro-propyl)-amide,
1-(3H-3,4,5,6-Tetraaza-cyclopenta[a]naphthalen-9-yl)-piperidine-3-carboxylic acid cyclopropylamide, 6-Methyl-1-(3H-3,4,5,6-tetraaza-cyclopenta[a]naphthalen-9-yl)-piperidine-3-carboxylic acid cyclopropylamide, 1-(3H-3,4,5,6-Tetraaza-cyclopenta[a]naphthalen-9-yl)-piperidine-3-carboxylic acid isopropylamide, 2-Cyano-N-[1-(3H-3,4,5,6-tetraaza-cyclopenta[a]naphthalen-9-yl)-piperidin-3-yl]-acetamide, 3,3,3-Trifluoro-N-[1-(3H-3,4,5,6-tetraaza-cyclopenta[a]naphthalen-9-yl)-piperidin-3-yl]-propionamide, 4,4,4-Trifluoro-N-[1-(3H-3,4,5,6-tetraaza-cyclopenta[a]naphthalen-9-yl)-piperidin-3-yl]-butyramide, 2-Nitrilo-ethanesulfonic acid [1-(3H-3,4,5,6-tetraaza-cyclopenta[a]naphthalen-9-yl)-piperidin-3-yl]-amide, 1-(3H-3,4,5,6-Tetraaza-cyclopenta[a]naphthalen-9-yl)-pyrrolidine-3-carboxylic acid cyanomethyl-amide, 1-(3H-3,4,5,6-Tetraaza-cyclopenta[a]naphthalen-9-yl)-pyrrolidine-3-carboxylic acid (2,2,2-trifluoro-ethyl)-amide, 1-(3H-3,4,5,6-Tetraaza-cyclopenta[a]naphthalen-9-yl)-pyrrolidine-3-carboxylic acid (3,3,3-trifluoro-propyl)-amide, 1-(3H-3,4,5,6-Tetraaza-cyclopenta[a]naphthalen-9-yl)-pyrrolidine-3-carboxylic acid cyclopropylamide, 1-(3H-3,4,5,6-Tetraaza-cyclopenta[a]naphthalen-9-yl)-pyrrolidine-3-carboxylic acid isopropylamide, 3,3,3-Trifluoro-N-[1-(3H-3,4,5,6-tetraaza-cyclopenta[a]naphthalen-9-yl)-pyrrolidin-3-yl]-propionamide, 4,4,4-Trifluoro-N-[1-(3H-3,4,5,6-tetraaza-cyclopenta[a]naphthalen-9-yl)-pyrrolidin-3-yl]-butyramide, Cyclopropanecarboxylic acid [1-(3H-3,4,5,6-tetraaza-cyclopenta[a]naphthalen-9-yl)-pyrrolidin-3-yl]-amide, N-[1-(3H-3,4,5,6-Tetraaza-cyclopenta[a]naphthalen-9-yl)-pyrrolidin-3-yl]-isobutyramide, 2-Cyano-N-[1-(3H-3,4,5,6-tetraaza-cyclopenta[a]naphthalen-9-yl)-pyrrolidin-3-yl]-acetamide, 2,2,2-Trifluoro-ethanesulfonic acid [1-(3H-3,4,5,6-tetraaza-cyclopenta[a]naphthalen-9-yl)-pyrrolidin-3-yl]-amide, 2-Nitrilo-ethanesulfonic acid [1-(3H-3,4,5,6-tetraaza-cyclopenta[a]naphthalen-9-yl)-pyrrolidin-3-yl]-amide, 1-(3H-3,4,5,6,8-Pentaaza-cyclopenta[a]naphthalen-9-yl)-piperidine-3-carboxylic acid (2,2,2-trifluoro-ethyl)-amide, 1-(3H-3,4,5,6,8-Pentaaza-cyclopenta[a]naphthalen-9-yl)-piperidine-3-carboxylic acid (3,3,3-trifluoro-propyl)-amide, 1-(3H-3,4,5,6,8-Pentaaza-cyclopenta[a]naphthalen-9-yl)-piperidine-3-carboxylic acid cyanomethyl-amide, 1-(3H-3,4,5,6,8-Pentaaza-cyclopenta[a]naphthalen-9-yl)-piperidine-3-carboxylic acid cyclopropylamide, 1-(3H-3,4,5,6,8-Pentaaza-cyclopenta[a]naphthalen-9-yl)-piperidine-3-carboxylic acid isopropylamide, 2-Cyano-N-[1-(3H-3,4,5,6,8-pentaaza-cyclopenta[a]naphthalen-9-yl)-piperidin-3-yl]-acetamide, 3,3,3-Trifluoro-N-[1-(3H-3,4,5,6,8-pentaaza-cyclopenta[a]naphthalen-9-yl)-piperidin-3-yl]-propionamide, 4,4,4-Trifluoro-N-[1-(3H-3,4,5,6,8-pentaaza-cyclopenta[a]naphthalen-9-yl)-piperidin-3-yl]-butyramide, 2,2,2-Trifluoro-ethanesulfonic acid [1-(3H-3,4,5,6,8-pentaaza-cyclopenta[a]naphthalen-9-yl)-piperidin-3-yl]-amide, 1-(3H-3,4,5,6,8-Pentaaza-cyclopenta[a]naphthalen-9-yl)-pyrrolidine-3-carboxylic acid cyanomethyl-amide, 1-(3H-3,4,5,6,8-Pentaaza-cyclopenta[a]naphthalen-9-yl)-pyrrolidine-3-carboxylic acid (2,2,2-trifluoro-ethyl)-amide, 1-(3H-3,4,5,6,8-Pentaaza-cyclopenta[a]naphthalen-9-yl)-pyrrolidine-3-carboxylic acid (3,3,3-trifluoro-propyl)-amide, 1-(3H-3,4,5,6,8-Pentaaza-cyclopenta[a]naphthalen-9-yl)-pyrrolidine-3-carboxylic acid cyclopropylamide, 1-(3H-3,4,5,6,8-Pentaaza-cyclopenta[a]naphthalen-9-yl)-pyrrolidine-3-carboxylic acid isopropylamide, 3,3,3-Trifluoro-N-[1-(3H-3,4,5,6,8-pentaaza-cyclopenta[a]naphthalen-9-yl)-pyrrolidin-3-yl]-propionamide, 4,4,4-Trifluoro-N-[1-(3H-3,4,5,6,8-pentaaza-cyclopenta[a]naphthalen-9-yl)-pyrrolidin-3-yl]-butyramide, Cyclopropanecarboxylic acid [1-(3H-3,4,5,6,8-pentaaza-cyclopenta[a]naphthalen-9-yl)-pyrrolidin-3-yl]-amide, N-[1-(3H-3,4,5,6,8-Pentaaza-cyclopenta[a]naphthalen-9-yl)-pyrrolidin-3-yl]-isobutyramide, 2-Cyano-N-[1-(3H-3,4,5,6,8-pentaaza-cyclopenta[a]naphthalen-9-yl)-pyrrolidin-3-yl]-acetamide, 2,2,2-Trifluoro-ethanesulfonic acid [1-(3H-3,4,5,6,8-pentaaza-cyclopenta[a]naphthalen-9-yl)-pyrrolidin-3-yl]-amide, 2-Nitrilo-ethanesulfonic acid [1-(3H-3,4,5,6,8-pentaaza-cyclopenta[a]naphthalen-9-yl)-pyrrolidin-3-yl]-amide, 1-(7-Methyl-3H-3,4,5,6,8-pentaaza-cyclopenta[a]naphthalen-9-yl)-piperidine-3-carboxylic acid (2,2,2-trifluoro-ethyl)-amide, 1-(7-Methyl-3H-3,4,5,6,8-pentaaza-cyclopenta[a]naphthalen-9-yl)-piperidine-3-carboxylic acid (3,3,3-trifluoro-propyl)-amide, 1-(7-Methyl-3H-3,4,5,6,8-pentaaza-cyclopenta[a]naphthalen-9-yl)-piperidine-3-carboxylic acid cyanomethyl-amide, 1-(7-Methyl-3H-3,4,5,6,8-pentaaza-cyclopenta[a]naphthalen-9-yl)-piperidine-3-carboxylic acid cyclopropylamide, 2-Cyano-N-[1-(7-methyl-3H-3,4,5,6,8-pentaaza-cyclopenta[a]naphthalen-9-yl)-piperidin-3-yl]-acetamide, 3,3,3-Trifluoro-N-[1-(7-methyl-3H-3,4,5,6,8-pentaaza-cyclopenta[a]naphthalen-9-yl)-piperidin-3-yl]-propionamide, 4,4,4-Trifluoro-N-[1-(7-methyl-3H-3,4,5,6,8-pentaaza-cyclopenta[a]naphthalen-9-yl)-piperidin-3-yl]-butyramide, 2,2,2-Trifluoro-ethanesulfonic acid [1-(7-ethyl-3H-3,4,5,6,8-pentaaza-cyclopenta[a]naphthalen-9-yl)-piperidin-3-yl]-amide, 1-(7-Methyl-3H-3,4,5,6,8-pentaaza-cyclopenta[a]naphthalen-9-yl)-pyrrolidine-3-carboxylic acid cyanomethyl-amide, 1-(7-Methyl-3H-3,4,5,6,8-pentaaza-cyclopenta[a]naphthalen-9-yl)-pyrrolidine-3-carboxylic acid (2,2,2-trifluoro-ethyl)-amide, 1-(7-Methyl-3H-3,4,5,6,8-pentaaza-cyclopenta[a]naphthalen-9-yl)-pyrrolidine-3-carboxylic acid (3,3,3-trifluoro-propyl)-amide, 1-(7-Methyl-3H-3,4,5,6,8-pentaaza-cyclopenta[a]naphthalen-9-yl)-pyrrolidine-3-carboxylic acid cyclopropylamide, 3,3,3-Trifluoro-N-[1-(7-methyl-3H-3,4,5,6,8-pentaaza-cyclopenta[a]naphthalen-9-yl)-pyrrolidin-3-yl]-propionamide, 4,4,4-Trifluoro-N-[1-(7-methyl-3H-3,4,5,6,8-pentaaza-cyclopenta[a]naphthalen-9-yl)-pyrrolidin-3-yl]-butyramide, 2-Cyano-N-[1-(7-methyl-3H-3,4,5,6,8-pentaaza-cyclopenta[a]naphthalen-9-yl)-pyrrolidin-3-yl]-acetamide, 2,2,2-Trifluoro-ethanesulfonic acid [1-(7-methyl-3H-3,4,5,6,8-pentaaza-cyclopenta[a]naphthalen-9-yl)-pyrrolidin-3-yl]-amide, 2-Nitrilo-ethanesulfonic acid [1-(7-methyl-3H-3,4,5,6,8-pentaaza-cyclopenta[a]naphthalen-9-yl)-pyrrolidin-3-yl]-amide, 1-(3H-3,4,5,6,7-Pentaaza-cyclopenta[a]naphthalen-9-yl)-piperidine-3-carboxylic acid (2,2,2-trifluoro-ethyl)-amide, 1-(3H-3,4,5,6,7-Pentaaza-cyclopenta[a]naphthalen-9-yl)-piperidine-3-carboxylic acid (3,3,3-trifluoro-propyl)-amide, 1-(3H-3,4,5,6,7-Pentaaza-cyclopenta[a]naphthalen-9-yl)-piperidine-3-carboxylic acid cyanomethyl-amide, 1-(3H-3,4,5,6,7-Pentaaza-cyclopenta[a]naphthalen-9-yl)-piperidine-3-carboxylic acid cyclopropylamide,
2-Cyano-N-[1-(3H-3,4,5,6,7-pentaaza-cyclopenta[a]naphthalen-9-yl)-piperidin-3-yl]-acetamide,
3,3,3-Trifluoro-N-[1-(3H-3,4,5,6,7-pentaaza-cyclopenta[a]naphthalen-9-yl)-piperidin-3-yl]-propionamide,
4,4,4-Trifluoro-N-[1-(3H-3,4,5,6,7-pentaaza-cyclopenta[a]naphthalen-9-yl)-piperidin-3-yl]-butyramide,
2,2,2-Trifluoro-ethanesulfonic acid [1-(3H-3,4,5,6,7-pentaaza-cyclopenta[a]naphthalen-9-yl)-piperidin-3-yl]-amide,
2-Nitrilo-ethanesulfinic acid [1-(3H-3,4,5,6,7-pentaaza-cyclopenta[a]naphthalen-9-yl)-piperidin-3-yl]-amide,
1-(3H-3,4,5,6,7-Pentaaza-cyclopenta[a]naphthalen-9-yl)-pyrrolidine-3-carboxylic acid (2,2,2-trifluoro-ethyl)-amide,
1-(3H-3,4,5,6,7-Pentaaza-cyclopenta[a]naphthalen-9-yl)-pyrrolidine-3-carboxylic acid (3,3,3-trifluoro-propyl)-amide,
1-(3H-3,4,5,6,7-Pentaaza-cyclopenta[a]naphthalen-9-yl)-pyrrolidine-3-carboxylic acid cyclopropylamide,
3,3,3-Trifluoro-N-[1-(3H-3,4,5,6,7-pentaaza-cyclopenta[a]naphthalen-9-yl)-pyrrolidin-3-yl]-propionamide,
4,4,4-Trifluoro-N-[1-(3H-3,4,5,6,7-pentaaza-cyclopenta[a]naphthalen-9-yl)-pyrrolidin-3-yl]-butyramide,
2-Cyano-N-[1-(3H-3,4,5,6,7-pentaaza-cyclopenta[a]naphthalen-9-yl)-pyrrolidin-3-yl]-acetamide,
2,2,2-Trifluoro-ethanesulfonic acid [1-(3H-3,4,5,6,7-pentaaza-cyclopenta[a]naphthalen-9-yl)-pyrrolidin-3-yl]-amide,
2-Nitrilo-ethanesulfonic acid [1-(3H-3,4,5,6,7-pentaaza-cyclopenta[a]naphthalen-9-yl)-pyrrolidin-3-yl]-amide,
1-(3H-3,4,5,7,8-Pentaaza-cyclopenta[a]naphthalen-9-yl)-piperidine-3-carboxylic acid (2,2,2-trifluoro-ethyl)-amide,
1-(3H-3,4,5,7,8-Pentaaza-cyclopenta[a]naphthalen-9-yl)-piperidine-3-carboxylic acid (3,3,3-trifluoro-propyl)-amide,
1-(3H-3,4,5,7,8-Pentaaza-cyclopenta[a]naphthalen-9-yl)-piperidine-3-carboxylic acid cyclopropylamide,
2-Cyano-N-[1-(3H-3,4,5,7,8-pentaaza-cyclopenta[a]naphthalen-9-yl)-piperidin-3-yl]-acetamide,
3,3,3-Trifluoro-N-[1-(3H-3,4,5,7,8-pentaaza-cyclopenta[a]naphthalen-9-yl)-piperidin-3-yl]-propionamide,
4,4,4-Trifluoro-N-[1-(3H-3,4,5,7,8-pentaaza-cyclopenta[a]naphthalen-9-yl)-piperidin-3-yl]-butyramide,
2,2,2-Trifluoro-ethanesulfonic acid [1-(3H-3,4,5,7,8-pentaaza-cyclopenta[a]naphthalen-9-yl)-piperidin-3-yl]-amide,
1-(3H-3,4,5,7,8-Pentaaza-cyclopenta[a]naphthalen-9-yl)-pyrrolidine-3-carboxylic acid (2,2,2-trifluoro-ethyl)-amide
1-(3H-3,4,5,7,8-Pentaaza-cyclopenta[a]naphthalen-9-yl)-pyrrolidine-3-carboxylic acid (3,3,3-trifluoro-propyl)-amide
3,3,3-Trifluoro-N-[1-(3H-3,4,5,7,8-pentaaza-cyclopenta[a]naphthalen-9-yl)-pyrrolidin-3-yl]-propionamide,
4,4,4-Trifluoro-N-[1-(3H-3,4,5,7,8-pentaaza-cyclopenta[a]naphthalen-9-yl)-pyrrolidin-3-yl]-butyramide,
2-Cyano-N-[1-(3H-3,4,5,7,8-pentaaza-cyclopenta[a]naphthalen-9-yl)-pyrrolidin-3-yl]-acetamide,
2,2,2-Trifluoro-ethanesulfonic acid [1-(3H-3,4,5,7,8-pentaaza-cyclopenta[a]naphthalen-9-yl)-pyrrolidin-3-yl]-amide,
2-Nitrilo-ethanesulfonic acid [1-(3H-3,4,5,7,8-pentaaza-cyclopenta[a]naphthalen-9-yl)-pyrrolidin-3-yl]-amide,
1-(3H-3,4,5,8-Tetraaza-cyclopenta[a]naphthalen-9-yl)-piperidine-3-carboxylic acid (2,2,2-trifluoro-ethyl)-amide,
1-(3H-3,4,5,8-Tetraaza-cyclopenta[a]naphthalen-9-yl)-piperidine-3-carboxylic acid (3,3,3-trifluoro-propyl)-amide,
1-(3H-3,4,5,8-Tetraaza-cyclopenta[a]naphthalen-9-yl)-piperidine-3-carboxylic acid cyclopropylamide,
2-Cyano-N-[1-(3H-3,4,5,8-tetraaza-cyclopenta[a]naphthalen-9-yl)-piperidin-3-yl]-acetamide,
3,3,3-Trifluoro-N-[1-(3H-3,4,5,8-tetraaza-cyclopenta[a]naphthalen-9-yl)-piperidin-3-yl]-propionamide,
4,4,4-Trifluoro-N-[1-(3H-3,4,5,8-tetraaza-cyclopenta[a]naphthalen-9-yl)-piperidin-3-yl]-butyramide,
2,2,2-Trifluoro-ethanesulfonic acid [1-(3H-3,4,5,8-tetraaza-cyclopenta[a]naphthalen-9-yl)-piperidin-3-yl]-amide,
1-(3H-3,4,5,8-Tetraaza-cyclopenta[a]naphthalen-9-yl)-pyrrolidine-3-carboxylic acid (2,2,2-trifluoro-ethyl)-amide,
1-(3H-3,4,5,8-Tetraaza-cyclopenta[a]naphthalen-9-yl)-pyrrolidine-3-carboxylic acid (3,3,3-trifluoro-propyl)-amide,
3,3,3-Trifluoro-N-[1-(3H-3,4,5,8-tetraaza-cyclopenta[a]naphthalen-9-yl)-pyrrolidin-3-yl]-propionamide,
4,4,4-Trifluoro-N-[1-(3H-3,4,5,8-tetraaza-cyclopenta[a]naphthalen-9-yl)-pyrrolidin-3-yl]-butyramide,
2-Cyano-N-[1-(3H-3,4,5,8-tetraaza-cyclopenta[a]naphthalen-9-yl)-pyrrolidin-3-yl]-acetamide,
2,2,2-Trifluoro-ethanesulfonic acid [1-(3H-3,4,5,8-tetraaza-cyclopenta[a]naphthalen-9-yl)-pyrrolidin-3-yl]-amide,
2-Nitrilo-ethanesulfonic acid [1-(3H-3,4,5,8-tetraaza-cyclopenta[a]naphthalen-9-yl)-pyrrolidin-3-yl]-amide,
1-(3H-3,4,5,7-Tetraaza-cyclopenta[a]naphthalen-9-yl)-piperidine-3-carboxylic acid (2,2,2-trifluoro-ethyl)-amide,
1-(3H-3,4,5,7-Tetraaza-cyclopenta[a]naphthalen-9-yl)-piperidine-3-carboxylic acid (3,3,3-trifluoro-propyl)-amide,
1-(3H-3,4,5,7-Tetraaza-cyclopenta[a]naphthalen-9-yl)-piperidine-3-carboxylic acid cyclopropylamide,
2-Cyano-N-[1-(3H-3,4,5,7-tetraaza-cyclopenta[a]naphthalen-9-yl)-piperidin-3-yl]-acetamide,
3,3,3-Trifluoro-N-[1-(3H-3,4,5,7-tetraaza-cyclopenta[a]naphthalen-9-yl)-piperidin-3-yl]-propionamide,
4,4,4-Trifluoro-N-[1-(3H-3,4,5,7-tetraaza-cyclopenta[a]naphthalen-9-yl)-piperidin-3-yl]-butyramide,
2,2,2-Trifluoro-ethanesulfonic acid [1-(3H-3,4,5,7-tetraaza-cyclopenta[a]naphthalen-9-yl)-piperidin-3-yl]-amide,
1-(3H-3,4,5,7-Tetraaza-cyclopenta[a]naphthalen-9-yl)-pyrrolidine-3-carboxylic acid (2,2,2-trifluoro-ethyl)-amide,
1-(3H-3,4,5,7-Tetraaza-cyclopenta[a]naphthalen-9-yl)-pyrrolidine-3-carboxylic acid (3,3,3-trifluoro-propyl)-amide,
3,3,3-Trifluoro-N-[1-(3H-3,4,5,7-tetraaza-cyclopenta[a]naphthalen-9-yl)-pyrrolidin-3-yl]-propionamide,
4,4,4-Trifluoro-N-[1-(3H-3,4,5,7-tetraaza-cyclopenta[a]naphthalen-9-yl)-pyrrolidin-3-yl]-butyramide,
2-Cyano-N-[1-(3H-3,4,5,7-tetraaza-cyclopenta[a]naphthalen-9-yl)-pyrrolidin-3-yl]-acetamide,
2,2,2-Trifluoro-ethanesulfonic acid [1-(3H-3,4,5,7-tetraaza-cyclopenta[a]naphthalen-9-yl)-pyrrolidin-3-yl]-amide,
2-Nitrilo-ethanesulfonic acid [1-(3H-3,4,5,7-tetraaza-cyclopenta[a]naphthalen-9-yl)-pyrrolidin-3-yl]-amide,
3-Oxo-3-[3-(3H-1,3,4,6-tetraaza-cyclopenta[a]naphthalen-9-yl)-piperidin-1-yl]-propionitrile,
3-Oxo-3-[3-(3-(3H-1,2,3,4,6-pentaaza-cyclopenta[a]naphthalen-9-yl)-piperidin-1-yl]-propionitrile,
3-Oxo-3-[3-(6H-2,4,5,6,8b-pentaaza-as-indacen-1-yl)-piperidin-1-yl]-propionitrile,
3-Oxo-3-[3-(3,4,6,9b-tetraaza-cyclopenta[a]naphthalen-9-yl)-piperidin-1-yl]-propionitrile,
3-Oxo-3-[3-(6H-2,3a,5,6-tetraaza-as-indacen-1-yl)-piperidin-1-yl]-propionitrile,
3-Oxo-3-[3-(2,5a,6,8b-tetraaza-as-indacen-1-yl)-piperidin-1-yl]-propionitrile, 3-Oxo-3-[3-(3,3a,6-triaza-cyclopenta[a]naphthalen-9-yl)-piperidin-1-yl]-propionitrile,
3-Oxo-3-[3-(3,3a,4,6-tetraaza-cyclopenta[a]naphthalen-9-yl)-piperidin-1-yl]-propionitrile,
3,3,3-Trifluoro-1-[3-(3H-1,3,4,6-tetraaza-cyclopenta[a]naphthalen-9-yl)-pyrrolidin-1-yl]-propan-1-one,
3,3,3-Trifluoro-1-[3-(3H-1,2,3,4,6-pentaaza-cyclopenta[a]naphthalen-9-yl)-pyrrolidin-1-yl]-propan-1-one,
3,3,3-Trifluoro-1-[3-(6H-2,4,5,6,8b-pentaaza-as-indacen-1-yl)-pyrrolidin-1-yl]-propan-1-one,
3,3,3-Trifluoro-1-[3-(3,4,6,9b-tetraaza-cyclopenta[a]naphthalen-9-yl)-pyrrolidin-1-yl]-propan-1-one,
3,3,3-Trifluoro-1-[3-(6H-2,3a,5,6-tetraaza-as-indacen-1-yl)-pyrrolidin-1-yl]-propan-1-one,
3,3,3-Trifluoro-1-[3-(2,5a,6,8b-tetraaza-as-indacen-1-yl)-pyrrolidin-1-yl]-propan-1-one,
3,3,3-Trifluoro-1-[3-(3,3a,6-triaza-cyclopenta[a]naphthalen-9-yl)-pyrrolidin-1-yl]-propan-1-one,
3,3,3-Trifluoro-1-[3-(3,3a,4,6-tetraaza-cyclopenta[a]naphthalen-9-yl)-pyrrolidin-1-yl]-propan-1-one,
3-Oxo-3-[3-(3H-1,3,4,5,6-pentaaza-cyclopenta[a]naphthalen-9-yl)-piperidin-1-yl]-propionitrile,
3-[3-(3H-1,2,3,4,5,6-Hexaaza-cyclopenta[a]naphthalen-9-yl)-piperidin-1-yl]-3-oxo-propionitrile,
3-[3-(3H-2,3,4,5,7,8a-Hexaaza-as-indacen-8-yl)-piperidin-1-yl]-3-oxo-propionitrile,
3-Oxo-3-[3-(3,4,5,6,9b-pentaaza-cyclopenta[a]napthalen-9-yl)-piperidin-1-yl]-propionitrile,
3-Oxo-3-[3-(6H-2,3a,4,5,6-pentaaza-as-indacen-1-yl)-piperidin-1-yl]-propionitrile,
3-Oxo-3-[3-(2,4,5a,6,8b-pentaaza-as-indacen-1-yl)-piperidin-1-yl]-propionitrile,
3-Oxo-3-[3-(3,3a,5,6-tetraaza-cyclopenta[a]naphthalen-9-yl)-piperidin-1-yl]-propionitrile,
3-Oxo-3-[3-(3,3a,4,5,6-pentaaza-cyclopenta[a]naphthalen-9-yl)-piperidin-1-yl]-propionitrile,
1-(3H-1,3,4,6-Tetraaza-cyclopenta[a]naphthalen-9-yl)-piperidine-3-carboxylic acid (2,2,2-trifluoro-ethyl)-amide,
1-(3H-1,2,3,4,6-Pentaaza-cyclopenta[a]naphthalen-9-yl)-piperidine-3-carboxylic acid (2,2,2-trifluoro-ethyl)-amide,
1-(6H-2,4,5,6,8b-Pentaaza-as-indacen-1-yl)-piperidine-3-carboxylic acid (2,2,2-trifluoro-ethyl)-amide,
1-(3,4,6,9b-Tetraaza-cyclopenta[a]naphthalen-9-yl)-piperidine-3-carboxylic acid (2,2,2-trifluoroethyl)-amide,
1-(6H-2,3a,5,6-Tetraaza-as-indacen-1-yl)-piperidine-3-carboxylic acid (2,2,2-trifluoro-ethyl)-amide,
1-(2,5a,6,8b-Tetraaza-as-indacen-1-yl)-piperidine-3-carboxylic acid (2,2,2-trifluoro-ethyl)-amide,
1-(3,3a,6-Triaza-cyclopenta[a]naphthalen-9-yl)-piperidine-3-carboxylic acid (2,2,2-trifluoro-ethyl)-amide and
1-(3,3a,4,6-Tetraaza-cyclopenta[a]naphthalen-9-yl)-piperidine-3-carboxylic acid (2,2,2-trifluoro-ethyl)-amide.

Biological Activity

Materials

Recombinant JAK1 (Amino acids 850-1154; NM_002227.2), JAK2 (Amino acids 808-1132; NM_004972.3) and JAK3 (Amino acids 781-1124; NM_000215.3) used in the studies were expressed using Invitrogen's Bac-to-Bac baculovirus expression system according to manufacturer's instructions. Adenosine 5'-triphosphate was obtained from Sigma Aldrich chemicals (Cat # A7699). Poly Glu-Tyr (4:1) sodium salt was obtained from Sigma Aldrich (Cat # P0275), Kinase Glo® Luminescent Kinase assay kit was obtained from Promega (Cat # V6713)

Methods

Kinase activity was assessed by Promega Kinase-Glo® Luminescent Kinase Assay kit using 200 μg/ml Poly Glu-Tyr (4:1) as substrate and ATP at 1 uM concentration. The reactions were carried out in 384 well plates in total reaction volume of 20 uL. Reaction mixtures contained 50 mM HEPES pH 7.4, 5 mM MgCl2, 1 mM DTT, 0.01% BSA, 0.01% Tween 20. Kinase was pre-incubated with compounds or 1% DMSO for 5 min before addition of substrate and ATP to check for inhibition. Kinase reactions were carried out at room temperature for 90 min. The reactions were stopped by adding 5 μl of Kinase Glo® reagent & 10 μl of reaction mixture followed by measuring luminescence. The luminescent signal is correlated with the amount of ATP present at the end of kinase reaction and is inversely correlated with the amount of kinase activity.

For each data point, % inhibition is calculated based on uninhibited reaction (without compound) which is considered as 100% activity over no enzyme or substrate controls. Dose response data is then fit using a four parameter logistic equation using Graph-pad Prism 5 software to determine inhibition constant 50 ($IC_{50}$).

We claim:

1. A compound of formula (I)

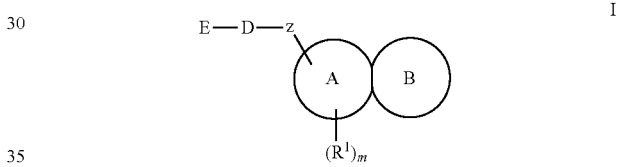

or their tautomers, stereoisomers, pharmaceutically acceptable salts, wherein,

A represents a five membered aromatic ring having upto two heteroatoms selected from O, N or S; or a six membered aromatic ring optionally having upto three heteroatoms selected from N;

B represents a fused heterocycle selected from:

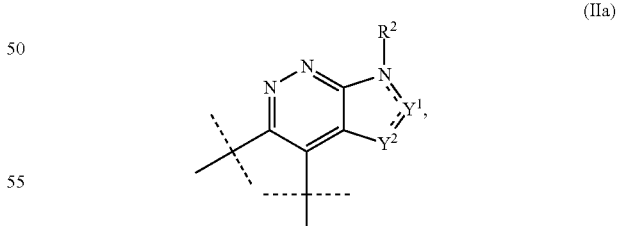

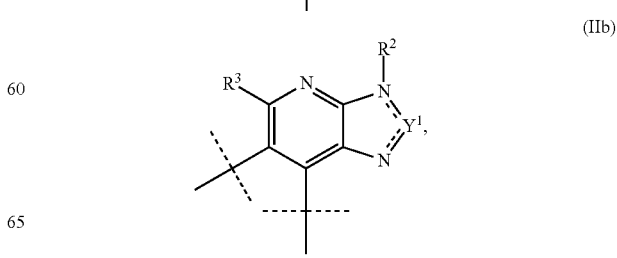

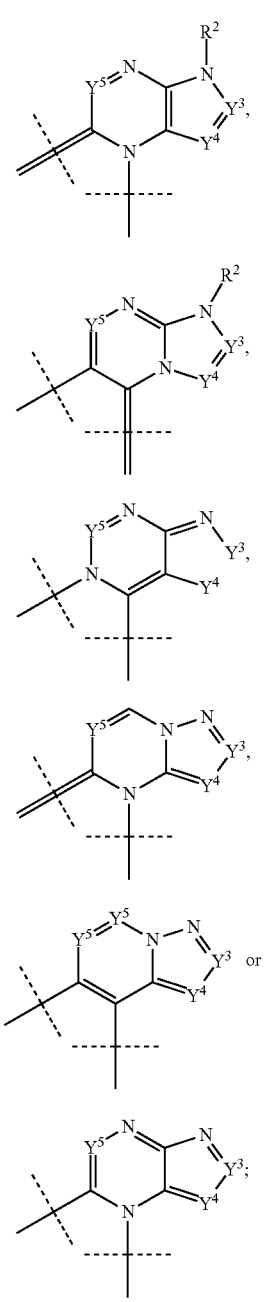

---- represents a single bond or a double bond provided that R² is absent when the bond between N to which it is attached and Y¹ represents a double bond;

Y¹, Y³, Y⁴ and Y⁵ independently represents N or CR⁴;

Y² represents NR⁴' or CR⁴R⁴' provided that R⁴' is absent when the bond between Y¹ and Y² represents a double bond;

R¹ is selected from hydrogen, alkyl, alkenyl, alkynyl, alkoxy, acyl, acylamino, acyloxy, —(CR$^a$R$^b$)$_n$C(O)R⁵, —(CR$^a$R$^b$)$_n$NR⁶R⁷, aminocarbonyl, alkoxycarbonylamino, alkylsulfonylamino, aminocarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —SO₃H, alkylthio, aminosulfonyl, alkylsulfonyl, or nitro;

R² is selected from hydrogen, alkyl, cycloalkyl, aryl, heterocyclyl or heteroaryl;

R³ is selected from the group consisting of hydrogen, hydroxyalkyl, amino, monoalkylamino, dialkylamino, halogen, perhaloalkyl, cyano, nitro, alkoxyalkyl, carboxy, carboxyalkyl, acyl, aminocarbonyl, alkyl, alkenyl, alkynyl, hydroxyalkyl, carboxyalkyl, haloalkyl and haloalkyloxy;

R⁴ and R⁴' are independently selected from the group consisting of hydrogen, halogen, hydroxyl, cyano, alkyl, alkenyl, alkynyl, haloalkyl, hydroxyalkyl, carboxyalkyl, cycloalkyl, cycloalkenyl, cycloalkylalkyl, aryl, arylalkyl, heterocyclyl, heterocyclylalkyl, heteroaryl and heteroarylalkyl;

wherein alkyl, alkenyl, alkynyl, cycloalkyl, cycloalkylalkyl, arylalkyl, aryl, heteroaryl, heteroarylalkyl, heterocyclyl, and heterocyclylalkyl are independently unsubstituted or substituted with upto four substituents independently selected from alkyl, alkenyl, alkynyl, alkoxy, acyl, acyloxy, acylamino, amino, halogen, hydroxy, hydroxyalkyl, keto, thiocarbonyl, carboxy, alkylcarboxy, carboxyalkyl, —SO₃H, aminocarbonyl, aminocarbonylamino, alkoxycarbonylamino, hydroxyamino, alkoxyamino, nitro, azido, cyano, cycloalkyl, cycloalkylalkyl, aryl, arylalkyl, heterocyclyl, heterocyclylalkyl, heteroaryl and heteroarylalkyl cycloalkenyl, cycloalkylamino, arylamino, heterocyclylamino, heteroarylamino, cycloalkyloxy, aryloxy, heterocyclyloxy or heteroaryloxy;

Z is a bond or is selected from cycloalkylene, cycloalkylenealkyl, cycloalkenylene, cycloalkyleneoxo, cycloalkyleneamino, arylene, arylenealkyl, arylenethio, aryleneoxy, aryleneamino, arylenealkoxycarbonylamino, arylenesulfonyl, arylenesulfonylamino, heterocyclylene, heterocyclylenealkyl, heterocyclyleneoxy, heterocyclylenealkyloxy, heterocyclyleneamino, heterocyclylenethio, heterocyclylenealkylamino heteroarylene, heteroarylenealkyl, heteroaryleneoxy, heteroaryleneamino, spirocyclyl, (C₁₋₆)alkylene, (C₁₋₆)alkenylene or (C₁₋₆)alkynylene wherein one or more than one methylene groups from alkylene, alkenylene or alkynylene are optionally replaced by hetero atoms or groups such as —O—, —S(O)p, —N(R⁵)—, or —C(O);

D is a bond or is selected from cycloalkylene, cycloalkenylene, cycloalkylenecarbonyl, cycloalkylenealkoxy, cycloalkyleneamino, arylene, arylenecarbonyl, arylenealkoxycarbonyl, arylenealkoxycarbonylamino, aryleneaminocarbonyl, heterocyclylene, heterocyclylene alkyl, heterocyclylenecarbonyl, heterocyclylenealkylamino, heteroarylene, heteroarylenecarbonyl, heteroarylenealkylamino, (C₁₋₆)alkylene, (C₁₋₆)alkenylene or (C₁₋₆)alkynylene wherein one or more than one methylene groups from alkylene, alkenylene or alkynylene are optionally replaced by hetero atoms or groups such as —O—, —S(O)p-, —N(R⁵)—, —C(O) or —C(=NR")— wherein R" is H, alkyl, cyano, hydroxy, hydroxyalkyl, haloalkyl or perhaloalkyl;

E is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —(CR$^a$R$^b$)$_n$OR⁵, —SR⁵, —(CR$^a$R$^b$)$_n$COOR⁵, —(CR$^a$R$^b$)$_n$NR⁶R⁷, —(CR$^a$R$^b$)$_n$C(O)NR⁶R⁷, —(CR$^a$R$^b$)$_n$NR⁵C(O)NR⁶R⁷, thiocarbonyl, S(O)₂NR⁶R⁷, —NR⁵S(O)₂R⁵, —S(O)$_p$R⁵, —SO₃H, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocycyloxy, heterocycloalkylamino, heteroaryl, heteroarylalkyl, heteroaryloxy, or heteroarylamino;

$R^5$ is selected from the group consisting of hydrogen, —$(CR^aR^b)_nOR^8$, halogen, haloalkyl, —$(CR^aR^b)_nC(O)R^8$, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, $OR^8$, —$OC(O)R^8$, —$(CR^aR^b)_nC(O)NR^6R^7$, —$NR^8C(O)R^8$, —$SR^8$, —$S(O)_pR^8$, —$S(O)_2NR^6R^7$ or —$NR^8S(O)_2R^8$;

$R^6$ and $R^7$ are independently selected from the group consisting of hydrogen, —$(CR^aR^b)_nOR^5$, haloalkyl, —$(CR^aR^b)_nC(O)R^5$, alkyl, alkenyl, alkynyl, aryl, arylalkyl, heteroaryl, heteroarylalkyl, cycloalkyl, cycloalkylalkyl, heterocyclyl and heterocyclylalkyl, or $R^6$ and $R^7$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —$(CR^aR^b)_nOR^5$, —$SR^5$, —$(CR^aR^b)_nNR^6R^7$, oxo, alkylsulfonyl, —$(CR^aR^b)_nCOOR^5$, —$(CR^aR^b)_nC(O)NR^6R^7$, cycloalkyl, cycloalkylalkyl, aryl, arylalkyl, heterocyclyl, heterocyclylalkyl, heteroaryl, or heteroarylalkyl;

Z, D and E may be optionally substituted with one or more substituents independently selected from cyano, nitro, keto, oxo, halogen, haloalkyl, perhaloalkyl, hydroxyamino, —$(CR^aR^b)_nOR^5$, —$(CR^aR^b)_nC(O)R^5$, —$OC(O)R^5$, —$SR^5$, —$(CR^aR^b)_nCOOR^5$, —$(CR^aR^b)_nNR^6R^7$, —$(CR^aR^b)_nC(O)NR^6R^7$, —$(CR^aR^b)_nNR^5C(O)NR^6R^7$, —$NR^5C(O)R^5$, thiocarbonyl, —$S(O)_2NR^6R^7$, —$NR^5S(O)_2R^5$, —$S(O)_pR^5$, —$SO_3H$, —$OP(O)(R^9)_q$, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —$OC(O)R^5$, —$(CR^aR^b)_nC(O)NR^6R^7$, —$NR^5C(O)R^5$, —$SR^5$, —$S(O)_pR^5$, —$S(O)_2NR^6R^7$ or —$NR^5S(O)_2R^5$;

$R^8$ is selected from the group consisting of hydrogen, alkyl, alkoxy, haloalkyl, aryl, arylalkyl, heteroaryl, heteroarylalkyl, cycloalkyl, cycloalkylalkyl, heterocyclyl and heterocyclylalkyl;

wherein alkyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy or carboxyalkyl;

$R^9$ is selected from the group consisting of hydroxy and alkoxy;

$R^a$ and $R^b$ are independently selected from the group consisting of hydrogen, —$OR^5$, halogen, haloalkyl, perhaloalkyl and alkyl;

n is 0-6;

m is 0, 1 or 2;

p is 0, 1 or 2; and q is 1 or 2;

with the proviso that in (IIc) when $Y^5$ is $CR^4$, then $Y^3$ and $Y^4$ cannot be $CR^4$.

2. A compound of formula (I) as claimed in claim 1 or its tautomers, stereoisomers, or pharmaceutically acceptable salts thereof, which is selected from a group consisting of:

1-(3H-3,4,5,6-Tetraaza-cyclopenta[a]naphthalen-9-yl)-piperidine-3-carboxylic acid (2,2,2-trifluoro-ethyl)-amide, 2,2,2-Trifluoro-ethanesulfonic acid[1-(3H-3,4,5,6-tetraaza-cyclopenta[a]naphthalen-9-yl)-piperidin-3-yl]-amide, 3,3,3-Trifluoro-1-[3-(3H-3,4,5,6-tetraaza-cyclopenta[a]naphthalen-9-yl)-piperidin-1-yl]-propan-1-one, 3-Oxo-3-[3-(3H-3,4,5,6-tetraaza-cyclopenta[a]naphthalen-9-yl)-piperidin-1-yl]-propionitrile, 4,4,4-Trifluoro-1-[3-(3H-3,4,5,6-tetraaza-cyclopenta[a]naphthalen-9-yl)-piperidin-1-yl]-butan-1-one,

[3-(3H-3,4,5,6-Tetraaza-cyclopenta[a]naphthalen-9-yl)-piperidine-1-sulfonyl]-acetonitrile, 9-[1-(2,2,2-Trifluoro-ethanesulfonyl)-piperidin-3-yl]-3H-3,4,5,6-tetraaza-cyclopenta[a]naphthalene, 3-[4-Methyl-3-(3H-3,4,5,6-tetraaza-cyclopenta[a]naphthalen-9-yl)-piperidin-1-yl]-3-oxo-propionitrile, 3-Oxo-3-[3-(3H-3,4,5,6-tetraaza-cyclopenta[a]naphthalen-9-yl)-pyrrolidin-1-yl]-propionitrile, 3,3,3-Trifluoro-1-[3-(3H-3,4,5,6-tetraaza-cyclopenta[a]naphthalen-9-yl)-pyrrolidin-1-yl]-propan-1-one, 4,4,4-Trifluoro-1-[3-(3H-3,4,5,6-tetraaza-cyclopenta[a]naphthalen-9-yl)-pyrrolidin-1-yl]-butan-1-one,

[3-(3H-3,4,5,6-Tetraaza-cyclopenta[a]naphthalen-9-yl)-pyrrolidine-1-sulfonyl]-acetonitrile, 9-[1-(2,2,2-Trifluoro-ethanesulfonyl)-pyrrolidin-3-yl]-3H-3,4,5,6-tetraaza-cyclopenta[a]naphthalene, 9-(1-Methanesulfonyl-pyrrolidin-3-yl)-3H-3,4,5,6-tetraaza-cyclopenta[a]naphthalene, 3,3,3-Trifluoro-1-[3-(3H-3,4,5,6,8-pentaaza-cyclopenta[a]naphthalen-9-yl)-piperidin-1-yl]-propan-1-one, 3-Oxo-3-[3-(3H-3,4,5,6,8-pentaaza-cyclopenta[a]naphthalen-9-yl)-piperidin-1-yl]-propionitrile, 4,4,4-Trifluoro-1-[3-(3H-3,4,5,6,8-pentaaza-cyclopenta[a]naphthalen-9-yl)-piperidin-1-yl]-butan-1-one,

[3-(3H-3,4,5,6,8-Pentaaza-cyclopenta[a]naphthalen-9-yl)-piperidine-1-sulfonyl]-acetonitrile, 9-[1-(2,2,2-Trifluoro-ethanesulfonyl)-piperidin-3-yl]-3H-3,4,5,6,8-pentaaza-cyclopenta[a]naphthalene, 9-(1-Methanesulfonyl-piperidin-3-yl)-3H-3,4,5,6,8-pentaaza-cyclopenta[a]naphthalene, 3-Oxo-3-[3-(3H-3,4,5,6,8-pentaaza-cyclopenta[a]naphthalen-9-yl)-pyrrolidin-1-yl]-propionitrile, 3,3,3-Trifluoro-1-[3-(3H-3,4,5,6,8-pentaaza-cyclopenta[a]naphthalen-9-yl)-pyrrolidin-1-yl]-propan-1-one, 4,4,4-Trifluoro-1-[3-(3H-3,4,5,6,8-pentaaza-cyclopenta[a]naphthalen-9-yl)-pyrrolidin-1-yl]-butan-1-one,

[3-(3H-3,4,5,6,8-Pentaaza-cyclopenta[a]naphthalen-9-yl)-pyrrolidine-1-sulfonyl]-acetonitrile, 9-[1-(2,2,2-Trifluoro-ethanesulfonyl)-pyrrolidin-3-yl]-3H-3,4,5,6,8-pentaaza-cyclopenta[a]naphthalene, 9-(1-Methanesulfonyl-pyrrolidin-3-yl)-3H-3,4,5,6,8-pentaaza-cyclopenta[a]naphthalene, 3,3,3-Trifluoro-1-[3-(7-methyl-3H-3,4,5,6,8-pentaaza-cyclopenta[a]naphthalen-9-yl)-piperidin-1-yl]-propan-1-one,
3-[3-(7-Methyl-3H-3,4,5,6,8-pentaaza-cyclopenta[a]naphthalen-9-yl)-piperidin-1-yl]-3-oxo-propionitrile,
4,4,4-Trifluoro-1-[3-(7-methyl-3H-3,4,5,6,8-pentaaza-cyclopenta[a]naphthalen-9-yl)-piperidin-1-yl]-butan-1-one,
[3-(7-Methyl-3H-3,4,5,6,8-pentaaza-cyclopenta[a]naphthalen-9-yl)-piperidine-1-sulfonyl]-acetonitrile,
7-Methyl-9-[1-(2,2,2-trifluoro-ethanesulfonyl)-piperidin-3-yl]-3H-,4,5,6,8-pentaaza-cyclopenta[a]naphthalene,
3-[3-(7-Methyl-3H-3,4,5,6,8-pentaaza-cyclopenta[a]naphthalen-9-yl)-pyrrolidin-1-yl]-3-oxo-propionitrile,
3,3,3-Trifluoro-1-[3-(7-methyl-3H-3,4,5,6,8-pentaaza-cyclopenta[a]naphthalen-9-yl)-pyrrolidin-1-yl]-propan-1-one,
4,4,4-Trifluoro-1-[3-(7-methyl-3H-3,4,5,6,8-pentaaza-cyclopenta[a]naphthalen-9-yl)-pyrrolidin-1-yl]-butan-1-one,
[3-(7-Methyl-3H-3,4,5,6,8-pentaaza-cyclopenta[a]naphthalen-9-yl)-pyrrolidine-1-sulfonyl]-acetonitrile,
7-Methyl-9-[1-(2,2,2-trifluoro-ethanesulfonyl)-pyrrolidin-3-yl]-3H-,4,5,6,8-pentaaza-cyclopenta[a]naphthalene,
3,3,3-Trifluoro-1-[3-(3H-3,4,5,7,8-pentaaza-cyclopenta[a]naphthalen-9-yl)-piperidin-1-yl]-propan-1-one,
3-Oxo-3-[3-(3H-3,4,5,7,8-pentaaza-cyclopenta[a]naphthalen-9-yl)-piperidin-1-yl]-propionitrile,
4,4,4-Trifluoro-1-[3-(3H-3,4,5,7,8-pentaaza-cyclopenta[a]naphthalen-9-yl)-piperidin-1-yl]-butan-1-one,
[3-(3H-3,4,5,7,8-Pentaaza-cyclopenta[a]naphthalen-9-yl)-piperidine-1-sulfonyl]-acetonitrile,
9-[1-(2,2,2-Trifluoro-ethanesulfonyl)-piperidin-3-yl]-3H-3,4,5,7,8-pentaaza-cyclopenta[a]naphthalene,
9-(1-Methanesulfonyl-piperidin-3-yl)-3H-3,4,5,7,8-pentaaza-cyclopenta[a]naphthalene,
3,3,3-Trifluoro-1-[3-(3H-3,4,5,7,8-pentaaza-cyclopenta[a]naphthalen-9-yl)-pyrrolidin-1-yl]-propan-1-one,
3-Oxo-3-[3-(3H-3,4,5,7,8-pentaaza-cyclopenta[a]naphthalen-9-yl)-pyrrolidin-1-yl]-propionitrile,
4,4,4-Trifluoro-1-[3-(3H-3,4,5,7,8-pentaaza-cyclopenta[a]naphthalen-9-yl)-pyrrolidin-1-yl]-butan-1-one,
[3-(3H-3,4,5,7,8-Pentaaza-cyclopenta[a]naphthalen-9-yl)-pyrrolidine-1-sulfonyl]-acetonitrile,
9-[1-(2,2,2-Trifluoro-ethanesulfonyl)-pyrrolidin-3-yl]-3H-3,4,5,7,8-pentaaza-cyclopenta[a]naphthalene,
9-(1-Methanesulfonyl-pyrrolidin-3-yl)-3H-3,4,5,7,8-pentaaza-cyclopenta[a]naphthalene,
3-Oxo-3-[3-(3H-3,4,5,6,7-pentaaza-cyclopenta[a]naphthalen-9-yl)-piperidin-1-yl]-propionitrile,
3,3,3-Trifluoro-1-[3-(3H-3,4,5,6,7-pentaaza-cyclopenta[a]naphthalen-9-yl)-piperidin-1-yl]-propan-1-one,
4,4,4-Trifluoro-1-[3-(3H-3,4,5,6,7-pentaaza-cyclopenta[a]naphthalen-9-yl)-piperidin-1-yl]-butan-1-one,
[3-(3H-3,4,5,6,7-Pentaaza-cyclopenta[a]naphthalen-9-yl)-piperidine-1-sulfonyl]-acetonitrile,
9-[1-(2,2,2-Trifluoro-ethanesulfonyl)-piperidin-3-yl]-3H-3,4,5,6,7-pentaaza-cyclopenta[a]naphthalene,
9-(1-Methanesulfonyl-piperidin-3-yl)-3H-3,4,5,6,7-pentaaza-cyclopenta[a]naphthalene,
3,3,3-Trifluoro-1-[3-(3H-3,4,5,6,7-pentaaza-cyclopenta[a]naphthalen-9-yl)-pyrrolidin-1-yl]-propan-1-one,
3-Oxo-3-[3-(3H-3,4,5,6,7-pentaaza-cyclopenta[a]naphthalen-9-yl)-pyrrolidin-1-yl]-propionitrile,
4,4,4-Trifluoro-1-[3-(3H-3,4,5,6,7-pentaaza-cyclopenta[a]naphthalen-9-yl)-pyrrolidin-1-yl]-butan-1-one,
[3-(3H-3,4,5,6,7-Pentaaza-cyclopenta[a]naphthalen-9-yl)-pyrrolidine-1-sulfonyl]-acetonitrile,
9-[1-(2,2,2-Trifluoro-ethanesulfonyl)-pyrrolidin-3-yl]-3H-3,4,5,6,7-pentaaza-cyclopenta[a]naphthalene,
9-(1-Methanesulfonyl-pyrrolidin-3-yl)-3H-3,4,5,6,7-pentaaza-cyclopenta[a]naphthalene,
3,3,3-Trifluoro-1-[3-(3H-3,4,5,7-tetraaza-cyclopenta[a]naphthalen-9-yl)-piperidin-1-yl]-propan-1-one,
4,4,4-Trifluoro-1-[3-(3H-3,4,5,7-tetraaza-cyclopenta[a]naphthalen-9-yl)-piperidin-1-yl]-butan-1-one,
[3-(3H-3,4,5,7-Tetraaza-cyclopenta[a]naphthalen-9-yl)-piperidine-1-sulfonyl]-acetonitrile,
9-[1-(2,2,2-Trifluoro-ethanesulfonyl)-piperidin-3-yl]-3H-3,4,5,7-tetraaza-cyclopenta[a]naphthalene,
9-(1-Methanesulfonyl-piperidin-3-yl)-3H-3,4,5,7-tetraaza-cyclopenta[a]naphthalene,
3,3,3-Trifluoro-1-[3-(3H-3,4,5,8-tetraaza-cyclopenta[a]naphthalen-9-yl)-piperidin-1-yl]-propan-1-one,
3-Oxo-3-[3-(3H-3,4,5,8-tetraaza-cyclopenta[a]naphthalen-9-yl)-piperidin-1-yl]-propionitrile,
4,4,4-Trifluoro-1-[3-(3H-3,4,5,8-tetraaza-cyclopenta[a]naphthalen-9-yl)-piperidin-1-yl]-butan-1-one,
9-[1-(2,2,2-Trifluoro-ethanesulfonyl)-piperidin-3-yl]-3H-3,4,5,8-tetraaza-cyclopenta[a]naphthalene,
[3-(3H-3,4,5,8-Tetraaza-cyclopenta[a]naphthalen-9-yl)-piperidine-1-sulfonyl]-acetonitrile,
9-(1-Methanesulfonyl-piperidin-3-yl)-3H-3,4,5,8-tetraaza-cyclopenta[a]naphthalene,
3-Oxo-3-[3-(3H-3,4,5,7-tetraaza-cyclopenta[a]naphthalen-9-yl)-pyrrolidin-1-yl]-propionitrile,
3,3,3-Trifluoro-1-[3-(3H-3,4,5,7-tetraaza-cyclopenta[a]naphthalen-9-yl)-pyrrolidin-1-yl]-propan-1-one,
4,4,4-Trifluoro-1-[3-(3H-3,4,5,7-tetraaza-cyclopenta[a]naphthalen-9-yl)-pyrrolidin-1-yl]-butan-1-one,
[3-(3H-3,4,5,7-Tetraaza-cyclopenta[a]naphthalen-9-yl)-pyrrolidine-1-sulfonyl]-acetonitrile,
9-[1-(2,2,2-Trifluoro-ethanesulfonyl)-pyrrolidin-3-yl]-3H-3,4,5,7-tetraaza-cyclopenta[a]naphthalene,
9-(1-Methanesulfonyl-pyrrolidin-3-yl)-3H-3,4,5,7-tetraaza-cyclopenta[a]naphthalene,
3,3,3-Trifluoro-1-[3-(3H-3,4,5,8-tetraaza-cyclopenta[a]naphthalen-9-yl)-pyrrolidin-1-yl]-propan-1-one,
3-Oxo-3-[3-(3H-3,4,5,8-tetraaza-cyclopenta[a]naphthalen-9-yl)-pyrrolidin-1-yl]-propionitrile,
4,4,4-Trifluoro-1-[3-(3H-3,4,5,8-tetraaza-cyclopenta[a]naphthalen-9-yl)-pyrrolidin-1-yl]-butan-1-one,
9-[1-(2,2,2-Trifluoro-ethanesulfonyl)-pyrrolidin-3-yl]-3H-3,4,5,8-tetraaza-cyclopenta[a]naphthalene,
[3-(3H-3,4,5,8-Tetraaza-cyclopenta[a]naphthalen-9-yl)-pyrrolidine-1-sulfonyl]-acetonitrile,
9-(1-Methanesulfonyl-pyrrolidin-3-yl)-3H-3,4,5,8-tetraaza-cyclopenta[a]naphthalene,
1-(3H-3,4,5,6-Tetraaza-cyclopenta[a]naphthalen-9-yl)-piperidine-3-carboxylic acid cyanomethyl-amide,
1-(3H-3,4,5,6-Tetraaza-cyclopenta[a]naphthalen-9-yl)-piperidine-3-carboxylic acid (3,3,3-trifluoro-propyl)-amide,
1-(3H-3,4,5,6-Tetraaza-cyclopenta[a]naphthalen-9-yl)-piperidine-3-carboxylic acid cyclopropylamide,
6-Methyl-1-(3H-3,4,5,6-tetraaza-cyclopenta[a]naphthalen-9-yl)-piperidine-3-carboxylic acid cyclopropylamide,
1-(3H-3,4,5,6-Tetraaza-cyclopenta[a]naphthalen-9-yl)-piperidine-3-carboxylic acid isopropylamide,
2-Cyano-N-[1-(3H-3,4,5,6-tetraaza-cyclopenta[a]naphthalen-9-yl)-piperidin-3-yl]-acetamide, 3,3,3-Trifluoro-N-[1-(3H-3,4,5,6-tetraaza-cyclopenta[a] naphthalen-9-yl)-piperidin-3-yl]-propionamide, 4,4,4-Trifluoro-N-[1-(3H-3,4,5,6-tetraaza-cyclopenta[a] naphthalen-9-yl)-piperidin-3-yl]-butyramide, 2-Nitrilo-ethanesulfonic acid [1-(3H-3,4,5,6-tetraaza-cyclopenta[a]naphthalen-9-yl)-piperidin-3-yl]-amide, 1-(3H-3,4,5,6-Tetraaza-cyclopenta[a]naphthalen-9-yl)-pyrrolidine-3-carboxylic acid cyanomethyl-amide, 1-(3H-3,4,5,6-Tetraaza-cyclopenta[a]naphthalen-9-yl)-pyrrolidine-3-carboxylic acid (2,2,2-trifluoro-ethyl)-amide, 1-(3H-3,4,5,6-Tetraaza-cyclopenta[a]naphthalen-9-yl)-pyrrolidine-3-carboxylic acid (3,3,3-trifluoro-propyl)-amide, 1-(3H-3,4,5,6-Tetraaza-cyclopenta[a]naphthalen-9-yl)-pyrrolidine-3-carboxylic acid cyclopropylamide, 1-(3H-3,4,5,6-Tetraaza-cyclopenta[a]naphthalen-9-yl)-pyrrolidine-3-carboxylic acid isopropylamide, 3,3,3-Trifluoro-N-[1-(3H-3,4,5,6-tetraaza-cyclopenta[a] naphthalen-9-yl)-pyrrolidin-3-yl]-propionamide, 4,4,4-Trifluoro-N-[1-(3H-3,4,5,6-tetraaza-cyclopenta[a] naphthalen-9-yl)-pyrrolidin-3-yl]-butyramide, Cyclopropanecarboxylic acid [1-(3H-3,4,5,6-tetraaza-cyclopenta[a]naphthalen-9-yl)-pyrrolidin-3-yl]-amide, N-[1-(3H-3,4,5, 6-Tetraaza-cyclopenta[a]naphthalen-9-yl)-pyrrolidin-3-yl]-isobutyramide, 2-Cyano-N-[1-(3H-3,4,5,6-tetraaza-cyclopenta[a]naphthalen-9-yl)-pyrrolidin-3-yl]-acetamide, 2,2,2-Trifluoro-ethanesulfonic acid [1-(3H-3,4,5,6-tetraaza-cyclopenta[a]naphthalen-9-yl)-pyrrolidin-3-yl]-amide, 2-Nitrilo-ethanesulfonic acid [1-(3H-3,4,5,6-tetraaza-cyclopenta[a]naphthalen-9-yl)-pyrrolidin-3-yl]-amide, 1-(3H-3,4,5,6,8-Pentaaza-cyclopenta[a]naphthalen-9-yl)-piperidine-3-carboxylic acid (2,2,2-trifluoro-ethyl)-amide, 1-(3H-3,4,5,6,8-Pentaaza-cyclopenta[a]naphthalen-9-yl)-piperidine-3-carboxylic acid (3,3,3-trifluoro-propyl)-amide, 1-(3H-3,4,5,6,8-Pentaaza-cyclopenta[a]naphthalen-9-yl)-piperidine-3-carboxylic acid cyanomethyl-amide, 1-(3H-3,4,5,6,8-Pentaaza-cyclopenta[a]naphthalen-9-yl)-piperidine-3-carboxylic acid cyclopropylamide, 1-(3H-3,4,5,6,8-Pentaaza-cyclopenta[a]naphthalen-9-yl)-piperidine-3-carboxylic acid isopropylamide, 2-Cyano-N-[1-(3H-3,4,5,6,8-pentaaza-cyclopenta[a] naphthalen-9-yl)-piperidin-3-yl]-acetamide, 3,3,3-Trifluoro-N-[1-(3H-3,4,5,6,8-pentaaza-cyclopenta [a]naphthalen-9-yl)-piperidin-3-yl]-propionamide, 4,4,4-Trifluoro-N-[1-(3H-3,4,5,6,8-pentaaza-cyclopenta [a]naphthalen-9-yl)-piperidin-3-yl]-butyramide, 2,2,2-Trifluoro-ethanesulfonic acid [1-(3H-3,4,5,6,8-pentaaza-cyclopenta[a]naphthalen-9-yl)-piperidin-3-yl]-amide, 1-(3H-3,4,5,6,8-Pentaaza-cyclopenta[a]naphthalen-9-yl)-pyrrolidine-3-carboxylic acid cyanomethyl-amide, 1-(3H-3,4,5,6,8-Pentaaza-cyclopenta[a]naphthalen-9-yl)-pyrrolidine-3-carboxylic acid (2,2,2-trifluoro-ethyl)-amide, 1-(3H-3,4,5,6,8-Pentaaza-cyclopenta[a]naphthalen-9-yl)-pyrrolidine-3-carboxylic acid (3,3,3-trifluoro-propyl)-amide, 1-(3H-3,4,5,6,8-Pentaaza-cyclopenta[a]naphthalen-9-yl)-pyrrolidine-3-carboxylic acid cyclopropylamide, 1-(3H-3,4,5,6,8-Pentaaza-cyclopenta[a]naphthalen-9-yl)-pyrrolidine-3-carboxylic acid isopropylamide, 3,3,3-Trifluoro-N-[1-(3H-3,4,5,6,8-pentaaza-cyclopenta [a]naphthalen-9-yl)-pyrrolidin-3-yl]-propionamide, 4,4,4-Trifluoro-N-[1-(3H-3,4,5,6,8-pentaaza-cyclopenta [a]naphthalen-9-yl)-pyrrolidin-3-yl]-butyramide, Cyclopropanecarboxylic acid [1-(3H-3,4,5,6,8-pentaaza-cyclopenta[a]naphthalen-9-yl)-pyrrolidin-3-yl]-amide, N-[1-(3H-3,4,5,6,8-Pentaaza-cyclopenta[a]naphthalen-9-yl)-pyrrolidin-3-yl]-isobutyramide, 2-Cyano-N-[1-(3H-3,4,5,6,8-pentaaza-cyclopenta[a] naphthalen-9-yl)-pyrrolidin-3-yl]-acetamide, 2,2,2-Trifluoro-ethanesulfonic acid [1-(3H-3,4,5,6,8-pentaaza-cyclopenta[a]naphthalen-9-yl)-pyrrolidin-3-yl]-amide, 2-Nitrilo-ethanesulfonic acid [1-(3H-3,4,5,6,8-pentaaza-cyclopenta[a]naphthalen-9-yl)-pyrrolidin-3-yl]-amide, 1-(7-Methyl-3H-3,4,5,6,8-pentaaza-cyclopenta[a]naphthalen-9-yl)-piperidine-3-carboxylic acid (2,2,2-trifluoro-ethyl)-amide, 1-(7-Methyl-3H-3,4,5,6,8-pentaaza-cyclopenta[a]naphthalen-9-yl)-piperidine-3-carboxylic acid (3,3,3-trifluoro-propyl)-amide, 1-(7-Methyl-3H-3,4,5,6,8-pentaaza-cyclopenta[a]naphthalen-9-yl)-piperidine-3-carboxylic acid cyanomethyl-amide, 1-(7-Methyl-3H-3,4,5,6,8-pentaaza-cyclopenta[a]naphthalen-9-yl)-piperidine-3-carboxylic acid cyclopropylamide, 2-Cyano-N-[1-(7-methyl-3H-3,4,5,6,8-pentaaza-cyclopenta[a]naphthalen-9-yl)-piperidin-3-yl]-acetamide, 3,3,3-Trifluoro-N-[1-(7-methyl-3H-3,4,5,6,8-pentaaza-cyclopenta[a]naphthalen-9-yl)-piperidin-3-yl]-propionamide, 4,4,4-Trifluoro-N-[1-(7-methyl-3H-3,4,5,6,8-pentaaza-cyclopenta[a]naphthalen-9-yl)-piperidin-3-yl]-butyramide, 2,2,2-Trifluoro-ethanesulfonic acid [1-(7-ethyl-3H-3,4,5,6,8-pentaaza-cyclopenta[a]naphthalen-9-yl)-piperidin-3-yl]-amide, 1-(7-Methyl-3H-3,4,5,6,8-pentaaza-cyclopenta[a]naphthalen-9-yl)-pyrrolidine-3-carboxylic acid cyanomethyl-amide, 1-(7-Methyl-3H-3,4,5,6,8-pentaaza-cyclopenta[a]naphthalen-9-yl)-pyrrolidine-3-carboxylic acid (2,2,2-trifluoro-ethyl)-amide, 1-(7-Methyl-3H-3,4,5,6,8-pentaaza-cyclopenta[a]naphthalen-9-yl)-pyrrolidine-3-carboxylic acid (3,3,3-trifluoro-propyl)-amide, 1-(7-Methyl-3H-3,4,5,6,8-pentaaza-cyclopenta[a]naphthalen-9-yl)-pyrrolidine-3-carboxylic acid cyclopropylamide, 3,3,3-Trifluoro-N-[1-(7-methyl-3H-3,4,5,6,8-pentaaza-cyclopenta[a]naphthalen-9-yl)-pyrrolidin-3-yl]-propionamide, 4,4,4-Trifluoro-N-[1-(7-methyl-3H-3,4,5,6,8-pentaaza-cyclopenta[a]naphthalen-9-yl)-pyrrolidin-3-yl]-butyramide, 2-Cyano-N-[1-(7-methyl-3H-3,4,5,6,8-pentaaza-cyclopenta[a]naphthalen-9-yl)-pyrrolidin-3-yl]-acetamide, 2,2,2-Trifluoro-ethanesulfonic acid [1-(7-methyl-3H-3,4,5,6,8-pentaaza-cyclopenta[a]naphthalen-9-yl)-pyrrolidin-3-yl]-amide, 2-Nitrilo-ethanesulfonic acid [1-(7-methyl-3H-3,4,5,6,8-pentaaza-cyclopenta[a]naphthalen-9-yl)-pyrrolidin-3-yl]-amide, 1-(3H-3,4,5,6,7-Pentaaza-cyclopenta[a]naphthalen-9-yl)-piperidine-3-carboxylic acid (2,2,2-trifluoro-ethyl)-amide, 1-(3H-3,4,5,6,7-Pentaaza-cyclopenta[a]naphthalen-9-yl)-piperidine-3-carboxylic acid (3,3,3-trifluoro-propyl)-amide, 1-(3H-3,4,5,6,7-Pentaaza-cyclopenta[a]naphthalen-9-yl)-piperidine-3-carboxylic acid cyanomethyl-amide, 1-(3H-3,4,5,6,7-Pentaaza-cyclopenta[a]naphthalen-9-yl)-piperidine-3-carboxylic acid cyclopropylamide, 2-Cyano-N-[1-(3H-3,4,5,6,7-pentaaza-cyclopenta[a]naphthalen-9-yl)-piperidin-3-yl]-acetamide, 3,3,3-Trifluoro-N-[1-(3H-3,4,5,6,7-pentaaza-cyclopenta[a]naphthalen-9-yl)-piperidin-3-yl]-propionamide, 4,4,4-Trifluoro-N-[1-(3H-3,4,5,6,7-pentaaza-cyclopenta[a]naphthalen-9-yl)-piperidin-3-yl]-butyramide, 2,2,2-Trifluoro-ethanesulfonic acid [1-(3H-3,4,5,6,7-pentaaza-cyclopenta[a]naphthalen-9-yl)-piperidin-3-yl]-amide, 2-Nitrilo-ethanesulfonic acid [1-(3H-3,4,5,6,7-pentaaza-cyclopenta[a]naphthalen-9-yl)-piperidin-3-yl]-amide, 1-(3H-3,4,5,6,7-Pentaaza-cyclopenta[a]naphthalen-9-yl)-pyrrolidine-3-carboxylic acid (2,2,2-trifluoro-ethyl)-amide, 1-(3H-3,4,5,6,7-Pentaaza-cyclopenta[a]naphthalen-9-yl)-pyrrolidine-3-carboxylic acid (3,3,3-trifluoro-propyl)-amide, 1-(3H-3,4,5,6,7-Pentaaza-cyclopenta[a]naphthalen-9-yl)-pyrrolidine-3-carboxylic acid cyclopropylamide, 3,3,3-Trifluoro-N-[1-(3H-3,4,5,6,7-pentaaza-cyclopenta[a]naphthalen-9-yl)-pyrrolidin-3-yl]-propionamide, 4,4,4-Trifluoro-N-[1-(3H-3,4,5,6,7-pentaaza-cyclopenta[a]naphthalen-9-yl)-pyrrolidin-3-yl]-butyramide, 2-Cyano-N-[1-(3H-3,4,5,6,7-pentaaza-cyclopenta[a]naphthalen-9-yl)-pyrrolidin-3-yl]-acetamide, 2,2,2-Trifluoro-ethanesulfonic acid [1-(3H-3,4,5,6,7-pentaaza-cyclopenta[a]naphthalen-9-yl)-pyrrolidin-3-yl]-amide, 2-Nitrilo-ethanesulfonic acid [1-(3H-3,4,5,6,7-pentaaza-cyclopenta[a]naphthalen-9-yl)-pyrrolidin-3-yl]-amide, 1-(3H-3,4,5,7,8-Pentaaza-cyclopenta[a]naphthalen-9-yl)-piperidine-3-carboxylic acid (2,2,2-trifluoro-ethyl)-amide, 1-(3H-3,4,5,7,8-Pentaaza-cyclopenta[a]naphthalen-9-yl)-piperidine-3-carboxylic acid (3,3,3-trifluoro-propyl)-amide, 1-(3H-3,4,5,7,8-Pentaaza-cyclopenta[a]naphthalen-9-yl)-piperidine-3-carboxylic acid cyclopropylamide, 2-Cyano-N-[1-(3H-3,4,5,7,8-pentaaza-cyclopenta[a]naphthalen-9-yl)-piperidin-3-yl]-acetamide, 3,3,3-Trifluoro-N-[1-(3H-3,4,5,7,8-pentaaza-cyclopenta[a]naphthalen-9-yl)-piperidin-3-yl]-propionamide, 4,4,4-Trifluoro-N-[1-(3H-3,4,5,7,8-pentaaza-cyclopenta[a]naphthalen-9-yl)-piperidin-3-yl]-butyramide, 2,2,2-Trifluoro-ethanesulfonic acid [1-(3H-3,4,5,7,8-pentaaza-cyclopenta[a]naphthalen-9-yl)-piperidin-3-yl]-amide, 1-(3H-3,4,5,7,8-Pentaaza-cyclopenta[a]naphthalen-9-yl)-pyrrolidine-3-carboxylic acid (2,2,2-trifluoro-ethyl)-amide 1-(3H-3,4,5,7,8-Pentaaza-cyclopenta[a]naphthalen-9-yl)-pyrrolidine-3-carboxylic acid (3,3,3-trifluoro-propyl)-amide 3,3,3-Trifluoro-N-[1-(3H-3,4,5,7,8-pentaaza-cyclopenta[a]naphthalen-9-yl)-pyrrolidin-3-yl]-propionamide, 4,4,4-Trifluoro-N-[1-(3H-3,4,5,7,8-pentaaza-cyclopenta[a]naphthalen-9-yl)-pyrrolidin-3-yl]-butyramide, 2-Cyano-N-[1-(3H-3,4,5,7,8-pentaaza-cyclopenta[a]naphthalen-9-yl)-pyrrolidin-3-yl]-acetamide, 2,2,2-Trifluoro-ethanesulfonic acid [1-(3H-3,4,5,7,8-pentaaza-cyclopenta[a]naphthalen-9-yl)-pyrrolidin-3-yl]-amide, 2-Nitrilo-ethanesulfonic acid [1-(3H-3,4,5,7,8-pentaaza-cyclopenta[a]naphthalen-9-yl)-pyrrolidin-3-yl]-amide, 1-(3H-3,4,5,8-Tetraaza-cyclopenta[a]naphthalen-9-yl)-piperidine-3-carboxylic acid (2,2,2-trifluoro-ethyl)-amide, 1-(3H-3,4,5,8-Tetraaza-cyclopenta[a]naphthalen-9-yl)-piperidine-3-carboxylic acid (3,3,3-trifluoro-propyl)-amide, 1-(3H-3,4,5,8-Tetraaza-cyclopenta[a]naphthalen-9-yl)-piperidine-3-carboxylic acid cyclopropylamide, 2-Cyano-N-[1-(3H-3,4,5,8-tetraaza-cyclopenta[a]naphthalen-9-yl)-piperidin-3-yl]-acetamide, 3,3,3-Trifluoro-N-[1-(3H-3,4,5,8-tetraaza-cyclopenta[a]naphthalen-9-yl)-piperidin-3-yl]-propionamide, 4,4,4-Trifluoro-N-[1-(3H-3,4,5,8-tetraaza-cyclopenta[a]naphthalen-9-yl)-piperidin-3-yl]-butyramide, 2,2,2-Trifluoro-ethanesulfonic acid [1-(3H-3,4,5,8-tetraaza-cyclopenta[a]naphthalen-9-yl)-piperidin-3-yl]-amide, 1-(3H-3,4,5,8-Tetraaza-cyclopenta[a]naphthalen-9-yl)-pyrrolidine-3-carboxylic acid (2,2,2-trifluoro-ethyl)-amide, 1-(3H-3,4,5,8-Tetraaza-cyclopenta[a]naphthalen-9-yl)-pyrrolidine-3-carboxylic acid (3,3,3-trifluoro-propyl)-amide, 3,3,3-Trifluoro-N-[1-(3H-3,4,5,8-tetraaza-cyclopenta[a]naphthalen-9-yl)-pyrrolidin-3-yl]-propionamide, 4,4,4-Trifluoro-N-[1-(3H-3,4,5,8-tetraaza-cyclopenta[a]naphthalen-9-yl)-pyrrolidin-3-yl]-butyramide, 2-Cyano-N-[1-(3H-3,4,5,8-tetraaza-cyclopenta[a]naphthalen-9-yl)-pyrrolidin-3-yl]-acetamide, 2,2,2-Trifluoro-ethanesulfonic acid [1-(3H-3,4,5,8-tetraaza-cyclopenta[a]naphthalen-9-yl)-pyrrolidin-3-yl]-amide, 2-Nitrilo-ethanesulfonic acid [1-(3H-3,4,5,8-tetraaza-cyclopenta[a]naphthalen-9-yl)-pyrrolidin-3-yl]-amide, 1-(3H-3,4,5,7-Tetraaza-cyclopenta[a]naphthalen-9-yl)-piperidine-3-carboxylic acid (2,2,2-trifluoro-ethyl)-amide, 1-(3H-3,4,5,7-Tetraaza-cyclopenta[a]naphthalen-9-yl)-piperidine-3-carboxylic acid (3,3,3-trifluoro-propyl)-amide, 1-(3H-3,4,5,7-Tetraaza-cyclopenta[a]naphthalen-9-yl)-piperidine-3-carboxylic acid cyclopropylamide, 2-Cyano-N-[1-(3H-3,4,5,7-tetraaza-cyclopenta[a]naphthalen-9-yl)-piperidin-3-yl]-acetamide, 3,3,3-Trifluoro-N-[1-(3H-3,4,5,7-tetraaza-cyclopenta[a]naphthalen-9-yl)-piperidin-3-yl]-propionamide, 4,4,4-Trifluoro-N-[1-(3H-3,4,5,7-tetraaza-cyclopenta[a]naphthalen-9-yl)-piperidin-3-yl]-butyramide, 2,2,2-Trifluoro-ethanesulfonic acid [1-(3H-3,4,5,7-tetraaza-cyclopenta[a]naphthalen-9-yl)-piperidin-3-yl]-amide, 1-(3H-3,4,5,7-Tetraaza-cyclopenta[a]naphthalen-9-yl)-pyrrolidine-3-carboxylic acid (2,2,2-trifluoro-ethyl)-amide, 1-(3H-3,4,5,7-Tetraaza-cyclopenta[a]naphthalen-9-yl)-pyrrolidine-3-carboxylic acid (3,3,3-trifluoro-propyl)-amide, 3,3,3-Trifluoro-N-[1-(3H-3,4,5,7-tetraaza-cyclopenta[a]naphthalen-9-yl)-pyrrolidin-3-yl]-propionamide, 4,4,4-Trifluoro-N-[1-(3H-3,4,5,7-tetraaza-cyclopenta[a]naphthalen-9-yl)-pyrrolidin-3-yl]-butyramide, 2-Cyano-N-[1-(3H-3,4,5,7-tetraaza-cyclopenta[a]naphthalen-9-yl)-pyrrolidin-3-yl]-acetamide,
2,2,2-Trifluoro-ethanesulfonic acid [1-(3H-3,4,5,7-tetraaza-cyclopenta[a]naphthalen-9-yl)-pyrrolidin-3-yl]-amide,
2-Nitrilo-ethanesulfonic acid [1-(3H-3,4,5,7-tetraaza-cyclopenta[a]naphthalen-9-yl)-pyrrolidin-3-yl]-amide,
3-Oxo-3-[3-(3H-1,3,4,6-tetraaza-cyclopenta[a]naphthalen-9-yl)-piperidin-1-yl]-propionitrile,
3-Oxo-3-[3-(3H-1,2,3,4,6-pentaaza-cyclopenta[a]naphthalen-9-yl)-piperidin-1-yl]-propionitrile,
3-Oxo-3-[3-(6H-2,4,5,6,8b-pentaaza-as-indacen-1-yl)-piperidin-1-yl]-propionitrile,
3-Oxo-3-[3-(3,4,6,9b-tetraaza-cyclopenta[a]naphthalen-9-yl)-piperidin-1-yl]-propionitrile,
3-Oxo-3-[3-(6H-2,3a,5,6-tetraaza-as-indacen-1-yl)-piperidin-1-yl]-propionitrile,
3-Oxo-3-[3-(2,5a,6,8b-tetraaza-as-indacen-1-yl)-piperidin-1-yl]-propionitrile,
3-Oxo-3-[3-(3,3a,6-triaza-cyclopenta[a]naphthalen-9-yl)-piperidin-1-yl]-propionitrile,
3-Oxo-3-[3-(3,3a,4,6-tetraaza-cyclopenta[a]naphthalen-9-yl)-piperidin-1-yl]-propionitrile,
3,3,3-Trifluoro-1-[3-(3H-1,3,4,6-tetraaza-cyclopenta[a]naphthalen-9-yl)-pyrrolidin-1-yl]-propan-1-one,
3,3,3-Trifluoro-1-[3-(3H-1,2,3,4,6-pentaaza-cyclopenta[a]naphthalen-9-yl)-pyrrolidin-1-yl]-propan-1-one,
3,3,3-Trifluoro-1-[3-(6H-2,4,5,6,8b-pentaaza-as-indacen-1-yl)-pyrrolidin-1-yl]-propan-1-one,
3,3,3-Trifluoro-1-[3-(3,4,6,9b-tetraaza-cyclopenta[a]naphthalen-9-yl)-pyrrolidin-1-yl]-propan-1-one,
3,3,3-Trifluoro-1-[3-(6H-2,3a,5,6-tetraaza-as-indacen-1-yl)-pyrrolidin-1-yl]-propan-1-one,
3,3,3-Trifluoro-1-[3-(2,5a,6,8b-tetraaza-as-indacen-1-yl)-pyrrolidin-1-yl]-propan-1-one,
3,3,3-Trifluoro-1-[3-(3,3a,6-triaza-cyclopenta[a]naphthalen-9-yl)-pyrrolidin-1-yl]-propan-1-one,
3,3,3-Trifluoro-1-[3-(3,3a,4,6-tetraaza-cyclopenta[a]naphthalen-9-yl)-pyrrolidin-1-yl]-propan-1-one,
3-Oxo-3-[3-(3H-1,3,4,5,6-pentaaza-cyclopenta[a]naphthalen-9-yl)-piperidin-1-yl]-propionitrile,
3-[3-(3H-1,2,3,4,5,6-Hexaaza-cyclopenta[a]naphthalen-9-yl)-piperidin-1-yl]-3-oxo-propionitrile,
3-[3-(3H-2,3,4,5,7,8a-Hexaaza-as-indacen-8-yl)-piperidin-1-yl]-3-oxo-propionitrile,
3-Oxo-3-[3-(3,4,5,6,9b-pentaaza-cyclopenta[a]naphthalen-9-yl)-piperidin-1-yl]-propionitrile,
3-Oxo-3-[3-(6H-2,3a,4,5,6-pentaaza-as-indacen-1-yl)-piperidin-1-yl]-propionitrile,
3-Oxo-3-[3-(2,4,5a,6,8b-pentaaza-as-indacen-1-yl)-piperidin-1-yl]-propionitrile,
3-Oxo-3-[3-(3,3a,5,6-tetraaza-cyclopenta[a]naphthalen-9-yl)-piperidin-1-yl]-propionitrile,
3-Oxo-3-[3-(3,3a,4,5,6-pentaaza-cyclopenta[a]naphthalen-9-yl)-piperidin-1-yl]-propionitrile,
1-(3H-1,3,4,6-Tetraaza-cyclopenta[a]naphthalen-9-yl)-piperidine-3-carboxylic acid (2,2,2-trifluoro-ethyl)-amide,
1-(3H-1,2,3,4,6-Pentaaza-cyclopenta[a]naphthalen-9-yl)-piperidine-3-carboxylic acid (2,2,2-trifluoro-ethyl)-amide,
1-(6H-2,4,5,6,8b-Pentaaza-as-indacen-1-yl)-piperidine-3-carboxylic acid (2,2,2-trifluoro-ethyl)-amide,
1-(3,4,6,9b-Tetraaza-cyclopenta[a]naphthalen-9-yl)-piperidine-3-carboxylic acid (2,2,2-trifluoroethyl)-amide,
1-(6H-2,3a,5,6-Tetraaza-as-indacen-1-yl)-piperidine-3-carboxylic acid (2,2,2-trifluoro-ethyl)-amide,
1-(2,5a,6,8b-Tetraaza-as-indacen-1-yl)-piperidine-3-carboxylic acid (2,2,2-trifluoro-ethyl)-amide,
1-(3,3a,6-Triaza-cyclopenta[a]naphthalen-9-yl)-piperidine-3-carboxylic acid (2,2,2-trifluoro-ethyl)-amide and
1-(3,3a,4,6-Tetraaza-cyclopenta[a]naphthalen-9-yl)-piperidine-3-carboxylic acid (2,2,2-trifluoro-ethyl)-amide.

3. A pharmaceutical composition comprising at least one compound of formula (I) or a pharmaceutically acceptable salt thereof according to claim 1 and one or more pharmaceutically acceptable carriers.

4. A method of inhibiting Janus family kinases (JAK) activity in a cell comprising contacting the cell with the compound according to claim 1 or a pharmaceutically acceptable salt thereof in an amount effective to inhibit the JAK activity of the cell.

5. The method of claim 4, wherein the contacting is in vitro.

6. The method of claim 4, wherein the contacting is in vivo.

* * * * *